US009695275B2

(12) United States Patent
Cheng

(10) Patent No.: US 9,695,275 B2
(45) Date of Patent: Jul. 4, 2017

(54) INTEGRATED ZWITTERIONIC CONJUGATED POLYMERS FOR BIOELECTRONICS, BIOSENSING, REGENERATIVE MEDICINE, AND ENERGY APPLICATIONS

(71) Applicant: THE UNIVERSITY OF AKRON, Akron, OH (US)

(72) Inventor: Gang Cheng, Fairlawn, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 15/028,040

(22) PCT Filed: Oct. 9, 2014

(86) PCT No.: PCT/US2014/059885
§ 371 (c)(1),
(2) Date: Apr. 8, 2016

(87) PCT Pub. No.: WO2015/054484
PCT Pub. Date: Apr. 16, 2015

(65) Prior Publication Data
US 2016/0244554 A1      Aug. 25, 2016

Related U.S. Application Data

(60) Provisional application No. 61/888,682, filed on Oct. 9, 2013.

(51) Int. Cl.
C08G 75/00      (2006.01)
C08G 61/12      (2006.01)
(Continued)

(52) U.S. Cl.
CPC ............ C08G 61/126 (2013.01); A61K 47/34 (2013.01); A61L 31/06 (2013.01);
(Continued)

(58) Field of Classification Search
CPC .. C08G 61/123; C08G 61/124; C08G 61/125; C08G 61/126; C08G 2261/143; C08G 2261/3223; C08G 2261/94
See application file for complete search history.

(56) References Cited

U.S. PATENT DOCUMENTS

2003/0219533 A1    11/2003  Chabrecek et al.
2006/0175193 A1     8/2006  Inganas et al.
(Continued)

OTHER PUBLICATIONS

Page, Zachariah Al., et al., Conjugated thiophene-containing polymer zwitterions; direct synthesis and thin film electronic properties; Macromolecules 46.2 (2012); 344-351.
(Continued)

*Primary Examiner* — Shane Fang
(74) *Attorney, Agent, or Firm* — Renner, Kenner, Greive, Bobak, Taylor & Weber Co. LPA

(57) ABSTRACT

The present invention is directed to a versatile and high performance zwitterionic CP platform, which integrates all desired functions into one material. This zwitterionic CP consists of the conducting backbone and multifunctional zwitterionic side chains. Non-conducting zwitterionic materials gain electronic conductivity through the conducting backbone and CPs obtain excellent biocompatibility, sensitivity to environmental stimuli and controllable antifouling properties via multifunctional zwitterionic side chains. Unique properties from two distinct materials (conducting materials and zwitterionic materials) are integrated into one material without sacrificing any properties. This platform can potentially be adapted for a range of applications (e.g. bioelectronics, tissue engineering, wound healing, robotic prostheses, biofuel cell, etc.), which all require high performance conducting materials with excellent antifouling/biocompatibility at complex biointerfaces. This conducting (Continued)

material platform will significantly advance the development of conducting polymers in the field of biomedicine and biotechnology.

28 Claims, 19 Drawing Sheets

(51) Int. Cl.
*A61K 47/34* (2017.01)
*A61L 31/06* (2006.01)

(52) U.S. Cl.
CPC .......... *C08G 2261/143* (2013.01); *C08G 2261/1644* (2013.01); *C08G 2261/3223* (2013.01); *C08G 2261/43* (2013.01); *C08G 2261/514* (2013.01); *C08G 2261/94* (2013.01)

(56) References Cited

U.S. PATENT DOCUMENTS

| | | | |
|---|---|---|---|
| 2010/0310462 A1 | 12/2010 | Asberg et al. | |
| 2011/0305881 A1 | 12/2011 | Schultz et al. | |
| 2012/0322939 A1 | 12/2012 | Jiang et al. | |
| 2013/0330386 A1* | 12/2013 | Whitten | C08F 230/08 424/409 |
| 2015/0218001 A1* | 8/2015 | Wang | C09K 11/65 424/9.6 |

OTHER PUBLICATIONS

Cao, Bin, et al. The impact of structure on elasticity, switchability, stability and functionality of an all-in-one carboxynetaine elastomer; Biomaterials 34.31 (Jul. 16, 2013); 7592-7600.

Gang Cheng, et al., Functionalizable and ultrastable zwitterionic nanogels; Langmuir 26.10 (2010); 6883-6886.

* cited by examiner

Fig. 6. pCBEDOT with quaternary ammonium (A) and tertiary amine (B) as the cation.

Fig. 13. Illustration of pCBEDOT glucose sensor.

INTEGRATED ZWITTERIONIC CONJUGATED POLYMERS FOR BIOELECTRONICS, BIOSENSING, REGENERATIVE MEDICINE, AND ENERGY APPLICATIONS

CROSS REFERENCE TO RELATED APPLICATIONS

This application claims the benefit of International application serial number PCT/US14/59885 entitled "Integrated Zwitterionic Conjugated Polymers for Bioelectronics, Biosensing, Regenerative Medicine, and Energy Applications" filed Oct. 9, 2014 and U.S. provisional patent application Ser. No. 61/888,682 entitled "Integrated Zwitterionic Conducting Polymers for Biosensing, Regenerative Medicine, and Energy Applications," filed Oct. 9, 2013 both of which are incorporated herein by reference in its entirety.

REFERENCE TO GOVERNMENT SUPPORT

The invention was made with government support under grant number NSF ECCS-1200032 awarded by National Science Foundation. The government has certain rights in the invention.

FIELD OF THE INVENTION

One or more embodiments of the present invention relate to zwitterionic conjugated polymers. In certain embodiments, the present invention relates to conjugated polymers and hydrogels comprising a conjugated polymer backbone and multifunctional zwitterionic side chains.

BACKGROUND OF THE INVENTION

Due to their unique properties of interacting with ions and solvents, polyelectrolytes have been used as key components for a wide range of biomedical, energy and environmental applications. Zwitterionic polyelectrolytes have balanced positive and negative charges and have been studied for use in drug delivery, biosensing and antimicrobial coatings and zwitterionic polymers having outstanding antifouling, antimicrobial, mechanical, optical and stability properties have been developed. Various zwitterionic polyelectrolytes have been found to have outstanding antifouling properties in resisting proteins, mammalian cells, and microbes, excellent in vivo biocompatibility, as well as the capability of further functionalization for applications in biosensing and drug delivery. However, existing zwitterionic polymers lack conductivity, optical properties, elasticity and quick response to physical stimuli, which limit their utility to address a broader range of challenges.

As a group of emerging biomaterials, conjugated polymers (CPs) have attracted significant interests for diagnosis, imaging, and therapy. In particular, CPs have attracted significant interests for numerous biomedical and biotech purposes, including bioelectronics and biosensing tissue engineering, wound healing, robotic prostheses, biofuel cell, etc., due to their great design flexibility, tunable conductivity, mechanical properties compatible with soft tissues and ease of fabrication over inorganic conducting or semiconducting materials. As core components in these devices, CPs improve communications between electrochemical devices and biological systems by allowing the delivery of smaller charges or the detection of very low electrical signals, so devices can perform more efficiently. However, biomacromolecules, such as proteins and lipids, tend to adsorb to hydrophobic CPs surfaces that are originally designed for non-biological and non-aqueous systems. The nonspecific adsorption of biomacromolecules on electrochemical device surfaces reduces the sensitivity and performance of the device and triggers foreign body response that eventually leads to the failure of implanted devices. In vivo studies have shown that the improved electrochemical performance of devices by CP coatings could not be sustained after implantation due to the formation of non-conductive scar tissues around devices.

Moreover, traditional conducting hydrogels are typically synthesized through either blending or physical crosslinking CPs with non-conducting polymeric hydrogel networks. Although these synthesis approaches are very easy and do not require long reaction time to achieve reasonable yields, non-conducting components can diminish electrochemical properties of conducting hydrogels. Secondly, physically crosslinked hydrogels are generally less stable and excessive crosslinking or doping metal ions reduce their biocompatibility. Thirdly, multiple components of a conducting hydrogel increase the difficulty of processing and micropatterning, which are important for fabricating hydrogel-based electronic devices. Furthermore, non-conducting components of current conducting hydrogels are not effective enough to prevent biofouling in the complex medium and foreign body response.

Accordingly, what is needed in the art is materials with high electrical conductivity, good biocompatibility, good stability, good non-fouling properties, and multi-functionality for allowing specific cell adhesion and proliferation.

SUMMARY OF THE INVENTION

The present invention is directed to a zwitterionic CP biomaterial platform that addresses challenges associated with existing CPs. The zwitterionic side chains in some embodiments of the present invention endow superior antifouling properties, enhance the electrical conductivity and improve the biocompatibility of CPs for bioelectronics devices, biosensors, tissue engineering scaffolds, wound healing dressings and robotic prostheses. In some embodiments, the zwitterionic CPs may be poly(carboxybetaine thiophene) (pCBTh), pCBTh-co-ThSH or pCBTh-co-ThMAA. The pCBTh-co-ThSH coated surface highly resists protein adsorption and cell attachment. The conductive pCBTh-co-ThMAA hydrogel exhibits good electrical conductivity, excellent antifouling property to resist nonspecific cell attachment and a functionality to incorporate cell adhesion molecules to allow the attachment of specific cells. This versatile CP platform can be directly used to improve the service life and performance of bioelectronic devices for a wide range of applications, including bioelectronics and biosensing, tissue engineering, wound healing, robotic prostheses, etc., which all demand high performance and biocompatible CPs at complex biointerfaces. (See FIG. 1).

In a first aspect, the present invention provides a conjugated polymer platform comprising a conjugated polymer backbone having one or more zwitterionic side chains. In one or more embodiments, the conjugated polymer platform also comprises one or more crosslinking side chains. In one or more embodiments, the conjugated polymer platform may include any one or more of the above referenced embodiments of the first aspect of the present invention further comprising one or more side chains for securing said conjugated polymer platform to a surface. In one or more embodiments, the conjugated polymer platform may include any one or more of the above referenced embodiments of the first aspect of the present invention further comprising one or more side chains for securing said conjugated polymer platform to a surface. In one or more embodiments, the conjugated polymer platform may include any one or more of the above referenced embodiments of the first aspect of the present invention further comprising one or more redox sensitive side chains for forming a redox sensitive hydrogel. In one or more embodiments, the conjugated polymer platform may include any one or more of the above referenced embodiments of the first aspect of the present invention further comprising positively and negatively charged side chains.

In one or more embodiments, the conjugated polymer platform may include any one or more of the above referenced embodiments of the first aspect of the present invention wherein said conjugated polymer backbone is selected from the group consisting of poly(thiophene)s, poly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide)s, poly(acetylene)s, poly(p-phenylene vinylene)s, and combinations thereof. In one or more embodiments, the conjugated polymer platform may include any one or more of the above referenced embodiments of the first aspect of the present invention wherein said conjugated polymer backbone is poly(thiophene).

In one or more embodiments, the conjugated polymer platform may include any one or more of the above referenced embodiments of the first aspect of the present invention wherein said zwitterionic side chains further comprise a carboxybetaine group, a sulfobetaine group or a phosphobetaine group. In one or more embodiments, the conjugated polymer platform may include any one or more of the above referenced embodiments of the first aspect of the present invention wherein said zwitterionic side chains further comprise a carboxybetaine group having at least one ethanol, propanol, butanol or pentanol group bonded to the nitrogen atom of said carboxybetaine group.

In one or more embodiments, the conjugated polymer platform may include any one or more of the above referenced embodiments of the first aspect of the present invention wherein said one or more crosslinking side chains further comprises a crosslinking moiety selected from the group comprising acrylates, or acrylamides, and combinations thereof. In one or more embodiments, the conjugated polymer platform may include any one or more of the above referenced embodiments of the first aspect of the present invention wherein said one or more crosslinking side chains comprises an acrylate, methacrylate, ethylacrylate, acrylamide, methacrylamide, ethacrylamide, alkene, azide or alkyne.

In one or more embodiments, the conjugated polymer platform may include any one or more of the above referenced embodiments of the first aspect of the present invention wherein said conjugated polymer platform is a hydrogel. In one or more embodiments, the conjugated polymer platform may include any one or more of the above referenced embodiments of the first aspect of the present invention wherein said one or more crosslinking side chains bond with each other or said conjugated polymer backbone to form a crosslinked polymer network.

In one or more embodiments, the conjugated polymer platform may include any one or more of the above referenced embodiments of the first aspect of the present invention wherein said one or more zwitterionic side chains has a corresponding cationic ring form.

In one or more embodiments, the conjugated polymer platform may include any one or more of the above referenced embodiments of the first aspect of the present invention wherein said one or more side chains for securing said conjugated polymer platform to a surface comprises an attachment moiety selected from the group consisting of thiols, ethoxysilanes, methoxysilanes, chlorosilanes, alkyl phosphates, 3,4-dihydroxyphenylalanine, and combinations thereof. In one or more embodiments, the conjugated polymer platform may include any one or more of the above referenced embodiments of the first aspect of the present invention wherein said one or more side chains for securing said conjugated polymer platform to a surface comprises an attachment moiety selected from the group consisting of cystamine, cysteine, 1-ethanol-2-thiol, (3-aminopropyl)triethoxysilane, (3-aminopropyl)trimethoxysilane, 3,4-dihydroxyphenethylamine, 12-hydroxy dodecyl phosphate, 2-aminoethylphosphonic acid, 3-aminopropylphosphonic acid, 4-aminobutylphosphonic acid, 2-hydrxylethylphosphonic acid, 3-hydrxylpropylphosphonic acid, 4-hydrxylbutylphosphonic acid, and combinations thereof.

In a second aspect, the present invention provides a redox sensitive hydrogel comprising a conjugated polymer backbone having one or more zwitterionic side chains and one or more crosslinking side chains having a thiol or other redox sensitive functional group, wherein said one or more crosslinking side chains form disulfide bonds with each other or with said conjugated polymer backbone to form a crosslinked polymer network. In one or more embodiments, the conjugated polymer backbone is selected from the group consisting of poly(thiophene)s, poly(fluorene)s, poly(phenylene)s, poly(pyrene)s, poly(azulene)s, poly(naphthalene)s, poly(pyrrole)s, polycarbazoles, poly(indole)s, poly(azepine)s, poly(aniline)s, poly(3,4-ethylenedioxythiophene), poly(p-phenylene sulfide)s, poly(acetylene)s, poly(p-phenylene vinylene)s, and combinations thereof. In one or more embodiments, the conjugated polymer backbone is poly(thiophene).

In one or more embodiments, the redox sensitive hydrogel may include any one or more of the above referenced embodiments of the first or second aspects of the present invention wherein said zwitterionic side chains further comprise a carboxybetaine group, a sulfobetaine group or a phosphobetaine group. In one or more embodiments, the redox sensitive hydrogel may include any one or more of the above referenced embodiments of the first or second aspects of the present invention wherein said zwitterionic side chains further comprise a carboxybetaine group. In one or more embodiments, the redox sensitive hydrogel may include any one or more of the above referenced embodiments of the first or second aspects of the present invention wherein said zwitterionic side chains further comprise a carboxybetaine group having at least one ethanol, propanol, butanol or pentanol group bonded to the nitrogen atom of said carboxybetaine group.

In a third aspect, the present invention provides a zwitterionic monomer for use in forming a conjugated polymer platform discussed above comprising a polymerizable thiophene or 3,4-ethylenedioxythiophene group and a zwitterionic carboxybetaine, sulfobetaine or phosphobetaine group. In one or more embodiments, the zwitterionic carboxybetaine group further comprises at least one ethanol, propanol, butanol or pentanol group bonded to the nitrogen atom of said carboxybetaine group.

In a fourth aspect, the present invention provides a conjugated polymer platform comprising a conjugated polymer backbone having mixed positively and negatively charged side chains. In one or more embodiments, the conjugated polymer backbone is selected from the group consisting of poly(thiophene)s, Poly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide)s, Poly(acetylene)s, Poly(p-phenylene vinylene)s, and combinations thereof.

In one or more embodiments, the conjugated polymer platform may include any one or more of the above referenced embodiments of the present invention wherein said side chains have a formula selected from:

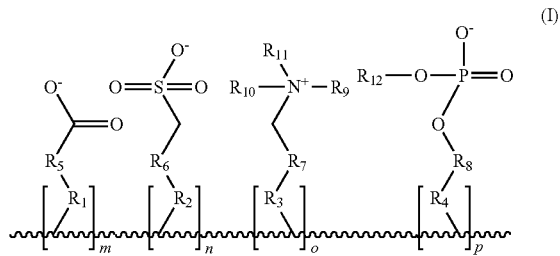
(I)

wherein $R_1$, $R_2$, $R_3$ and $R_4$ are —O—, —NH—, —C(O)NH—, —CH$_2$C(O)NH—, —CH$_2$CH$_2$C(O)NH—, —(CH$_2$)$_x$C(O)NH—, —NHC(O)—, —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$NHC(O)O(CH$_2$)$_y$—, —(CH$_2$)$_x$OC(O)NH(CH$_2$)$_y$—, —(CH$_2$)$_x$C(O)NH(CH$_2$)$_y$—, —NHC(O)(CH$_2$)$_x$C(O)NH—, —OC(O)(CH$_2$)$_x$C(O)NH—, —O(CH$_2$)$_x$C(O)NH—, —NHC(O)(CH$_2$)$_x$O—, —NHC(O)(CH$_2$)$_x$C(O)O—, —C(O)O—, —CH$_2$C(O)O—, —CH$_2$CH$_2$C(O)O—, —(CH$_2$)$_x$C(O)O—, —OC(O)—, —OC(O)CH$_2$—, —OC(O)CH$_2$CH$_2$—, —OC(O)(CH$_2$)$_x$—, —OC(O)(CH$_2$)$_x$C(O)O—, —OC(O)(CH$_2$)$_x$O—, —O(CH$_2$)$_x$C(O)O—, —(CH$_2$)$_x$OC(O)(CH$_2$)$_y$—, —(CH$_2$)$_m$C(O)O(CH$_2$)$_x$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_x$O—, —O(CH$_2$)$_x$—, —(CH$_2$)$_x$—, —O(CH$_2$CH$_2$O)$_x$—, —(OCH$_2$CH$_2$)$_x$— or —(CH$_2$CH$_2$O)$_x$—; $R_5$, $R_6$, $R_7$ and $R_8$ are —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_{z-1}$—, —NHC(O)—, —NHC(O)CH$_2$—, —NHC(O)CH$_2$CH$_2$—, —NHC(O)(CH$_2$)$_z$—, —OC(O)—, —OC(O)CH$_2$—, —OC(O)CH$_2$CH$_2$— or —OC(O)(CH$_2$)$_z$—; $R_9$, $R_{10}$ and $R_{11}$ are —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_{12}$ is —H, —CH$_3$, —CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; x, y and z are each an integer from 1 to 20; ⌇⌇⌇ is the conjugated polymer backbone; m, n and p are each an integer from 0 to 10,000,000; and o is an integer from 1 to 10,000,000.

In one or more embodiments, the conjugated polymer platform may include any one or more of the above referenced embodiments of the present invention wherein said side chains have a formula selected from the group consisting of:

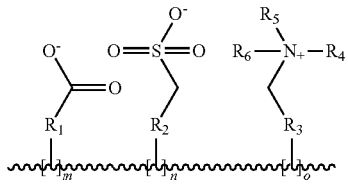
(II)

wherein $R_1$ is —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$NHC(O)O(CH$_2$)$_y$—, —(CH$_2$)$_x$OC(O)NH(CH$_2$)$_y$—, —(CH$_2$)$_x$C(O)NH(CH$_2$)$_y$—, —OC(O)CH$_2$—, —OC(O)CH$_2$CH$_2$—, —OC(O)(CH$_2$)$_x$—, —(CH$_2$)$_x$OC(O)(CH$_2$)$_y$—, —(CH$_2$)$_m$C(O)O(CH$_2$)$_x$—, —O(CH$_2$)$_x$—, —(CH$_2$)$_x$— or —(OCH$_2$CH$_2$)$_x$—; $R_2$, and $R_3$ are —C(O)NH—, —CH$_2$C(O)NH—, —CH$_2$CH$_2$C(O)NH—, —(CH$_2$)$_z$C(O)NH—, —NHC(O)—, —NHC(O)CH$_2$—, —NHC(O)CH$_2$CH$_2$—, —NHC(O)(CH$_2$)$_v$—, —(CH$_2$)$_z$NHC(O)(CH$_2$)$_v$—, —(CH$_2$)$_z$NHC(O)O(CH$_2$)$_v$—, —(CH$_2$)$_z$OC(O)NH(CH$_2$)$_v$—, —(CH$_2$)$_z$C(O)NH(CH$_2$)$_v$—, —NHC(O)(CH$_2$)$_z$C(O)NH—, —OC(O)(CH$_2$)$_z$C(O)NH—, —O(CH$_2$)$_z$C(O)NH—, —NHC(O)(CH$_2$)$_z$O—, —NHC(O)(CH$_2$)$_z$C(O)O—, —C(O)O—, —CH$_2$C(O)O—, —CH$_2$CH$_2$C(O)O—, —(CH$_2$)$_z$C(O)O—, OC(O)—, —OC(O)CH$_2$—, —OC(O)CH$_2$CH$_2$—, —OC(O)(CH$_2$)$_z$—, —OC(O)(CH$_2$)$_z$C(O)O—, —OC(O)(CH$_2$)$_z$O—, —O(CH$_2$)$_z$C(O)O—, —(CH$_2$)$_z$OC(O)(CH$_2$)$_v$—, —(CH$_2$)$_z$C(O)O(CH$_2$)$_v$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_z$O—, —O(CH$_2$)$_z$O—, —O(CH$_2$)$_z$—, —(CH$_2$)$_z$—, —O(CH$_2$CH$_2$O)$_z$—, —(OCH$_2$CH$_2$)$_z$— or —(CH$_2$CH$_2$O)$_x$—; $R_4$, $R_5$, and $R_6$ are —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m, n, x, y and z are each an integer from 0 to 10,000,000 and o is an integer from 1 to 10,000,000. In a fifth aspect, the present invention provides a method of making the conjugated polymer platform of described above comprising forming a zwitterionic monomer having a polymerizable thiophene or 3,4-ethylenedioxythiophene (EDOT) group and a zwitterionic betaine group; dissolving said zwitterionic monomer in a suitable solvent; and polymerizing said polymerizable thiophene or 3,4-ethylenedioxythiophene (EDOT) group of said zwitterionic monomer to form the conjugated polymer.

In one or more embodiments, the method of this aspect of the invention further comprising forming a crosslinking monomer having a polymerizable thiophene or 3,4-ethylenedioxythiophene (EDOT) group and a crosslinking group and dissolving said crosslinking monomer in a suitable solvent; combining the crosslinking monomer solution with the zwitterionic monomer solution; and polymerizing the polymerizable thiophene or 3,4-ethylenedioxythiophene (EDOT) groups of said zwitterionic monomer and said crosslinking monomer to form the conjugated polymer platform.

In some embodiments, the method may further comprise forming a securing monomer having a polymerizable thiophene or 3,4-ethylenedioxythiophene (EDOT) group and a securing moiety selected from the group consisting of a thiol cystamine, cysteine, 1-ethanol-2-thiol, (3-aminopropyl)triethoxysilane, (3-aminopropyl)trimethoxysilane, 3,4-dihydroxyphenethylamine, 12-hydroxy dodecyl phosphate, 2-aminoethylphosphonic acid, 3-aminopropylphosphonic acid, 4-aminobutylphosphonic acid, 2-hydrxylethylphosphonic acid, 3-hydrxylpropylphosphonic acid, 4-hydrxylbutylphosphonic acid, and combinations thereof group and dissolving said securing monomer in a suitable solvent; combining the securing monomer solution with the zwitterionic monomer solution and polymerizing the polymerizable thiophene or 3,4-ethylenedioxythiophene (EDOT) groups of said zwitterionic monomer, and said securing monomer to form the conjugated polymer platform described above. In one or more embodiments, the method may include any one or more of the above referenced embodiments of the fifth aspect of the present invention further comprising: combining the crosslinking monomer solution, the securing monomer solution and the zwitterionic monomer solution and polymerizing said polymerizable thiophene or 3,4-ethylenedioxythiophene (EDOT) groups of said zwitterionic monomer, said crosslinking monomer, and said securing monomer to form the conjugated polymer platform. In one or more embodiments, the method may include any one or more of the above referenced embodiments of the fifth aspect of the present invention further wherein the zwitterionic betaine group is added to said zwitterionic monomer after the polymerization step. In one or more embodiments, the method may include any one or more of the above referenced embodiments of the fifth aspect of the present invention wherein said zwitterionic monomer is the zwitterionic monomer described above. In one or more embodiments, the method may include any one or more of the above referenced embodiments of the fifth aspect of the present invention wherein the polymerizable thiophene or 3,4-ethylenedioxythiophene (EDOT) groups of said zwitterionic monomer are polymerized by using a suitable radical initiator.

In a sixth aspect, the present invention provides a method of making the zwitterionic monomer of described above comprising: dissolving 3-thiopheneacetic acid in a suitable solvent; adding 1,1'-carbonyldiimidazole (CDI) to the solution and reducing the temperature; adding N,N'-dimethylethylenediamine diluted with anhydrous THF to the resulting product to form N-(2-(dimethylamino)ethyl)-2-(thiophen-3-yl)acetamide; dissolving the resulting polymer in a suitable solvent and reacting it with ethyl bromoacetate to form 2-ethoxy-N,N-dimethyl-2-oxo-N-(2-(2-(thiophen-3-yl)acetamido)ethyl)ethan-1-aminium bromide; dissolving the resulting polymer in deionized water and passing it through an ion exchange resin filled column to hydrolyze the ethyl ester into a zwitterionic form to produce a zwitterionic monomer as described above.

In one or more embodiments, the method may comprise: dissolving 3-thiopheneacetic acid in a suitable solvent; adding 1,1'-carbonyldiimidazole (CDI) to the solution and reducing the temperature; adding N,N'-dimethylethylenediamine diluted with anhydrous THF to form N-(2-(dimethylamino)ethyl)-2-(thiophen-3-yl)acetamide; dissolving the N-(2-(dimethylamino)ethyl)-2-(thiophen-3-yl)acetamide in a suitable solvent and reacting it with ethyl bromoacetate to form 2-ethoxy-N,N-dimethyl-2-oxo-N-(2-(2-(thiophen-3-yl)acetamido)ethyl)ethan-1-aminium bromide; dissolving the resulting polymer in deionized water and passing it through an ion exchange resin filled column to hydrolyze the ethyl ester into a zwitterionic form to produce a zwitterionic monomer as described above. In one or more embodiments, the method may comprise: dissolving polymerizable component of a conjugated polymer in a suitable solvent; adding a bifunctional linker to the solution at the presence of suitable catalyst(s); and adding betaine or its derivatives or the combination thereof to the resulting product in a suitable solvent to produce the zwitterionic monomer.

In one or more embodiments, the method may comprise: dissolving (2,3-dihydrothieno[3,4-b][1,4]dioxin-2-yl)methanol and sodium hydride in a suitable solvent; adding 1-bromo-3-chloropropane to the solution; adding dimethylglycinate ester in a suitable solvent to form 2-((3-((2,3-dihydrothieno[3,4-b][1,4]dioxin-2-yl)oxy)propyl)dimethylammonio)acetate ester; and dissolving the resulting product in a suitable solvent containing the suitable chemical reagent(s) to remove ester to produce a zwitterionic monomer as described above.

In a seventh aspect, the present invention provides a method of making the redox sensitive hydrogel described above comprising: preparing an solution comprising a conjugated polymer platform having a conjugated polymer backbone, one or more zwitterionic side chains, and one or more crosslinking side chains, said crosslinking side chains having a thiol or other redox sensitive functional group; add oxidizer to form disulfide bonds between the crosslinking side chains or between the crosslinking side chains and the conjugated polymer backbone to form a crosslinked polymer network.

In another aspect, the present invention provides a zwitterionic biomaterial platform comprising the zwitterionic conjugated polymer platform described above. In another aspect, the present invention provides an implantable medical device comprising the zwitterionic conjugated polymer platform described above. In another aspect, the present invention provides a solar cell comprising the zwitterionic conjugated polymer platform described above. In another aspect, the present invention provides a biosensor comprising the zwitterionic conjugated polymer platform described above.

In some embodiments, the zwitterionic conjugated polymers can be used to fabricate electrodes that deliver or detect electrical signal in medical devices. In some embodiments, the zwitterionic conjugated polymers can be used to fabricate bio or chemical sensors in medical devices. In some embodiments, the zwitterionic conjugated polymers can be used to fabricate the tissue engineering scaffold for tissue regeneration. In some embodiments, the zwitterionic conjugated polymers can be used to fabricate optical sensors in medical devices. In some embodiments, the zwitterionic conjugated polymers can be used to fabricate transistor, transducer or supercapacitor in medical devices. In some embodiments, the zwitterionic conjugated polymers can be used as electron or ion collectors in bioelectronic devices. In some embodiments, the zwitterionic conjugated polymers can be used as a semiconductor to fabricate bioelectronic devices. In some embodiments, the zwitterionic conjugated polymers can be used as antifouling coating of medical devices to prevent biofouling and infection. In some embodiments, the zwitterionic conjugated polymers can be used as antimicrobial coating of medical devices to prevent biofouling and infection.

In yet another aspect, embodiments of the present invention are directed to a solar cell comprising the zwitterionic conjugated polymer described above. In some of these embodiments, the zwitterionic conjugated polymers may be used as electron donor and electron acceptor materials in fabricating the solar cell. In some of these embodiments, the zwitterionic conjugated polymers can be used as electron or ion collectors for the solar cell. In yet another aspect, embodiments of the present invention are directed to a battery comprising the zwitterionic conjugated polymer described above. In some of these embodiments, the zwitterionic conjugated polymers can be used as electron donor and electron acceptor materials in fabrication of the battery. In some of these embodiments, the zwitterionic conjugated polymers can be used as electron or ion collectors in the battery. In yet another aspect, embodiments of the present invention are directed to a supercapacitor comprising the zwitterionic conjugated polymer described above. In some of these embodiments, the zwitterionic conjugated polymers can be used as electron donor and electron acceptor materials in fabricating the supercapacitor. In some of these embodiments, the zwitterionic conjugated polymers can be used as electron or ion collectors in the supercapacitor.

BRIEF DESCRIPTION OF THE DRAWINGS

For a more complete understanding of the features and advantages of the present invention, reference is now made to the detailed description of the invention along with the accompanying figures in which.

FIG. His a graph showing quantitative cell density on the pCBTh-co-ThMAA hydrogel, pCBTh-co-ThRGD hydrogel, pCBMA hydrogel, pThAA hydrogel, and TCPS surfaces shown in FIGS. 10A-E above.

Figure 12:
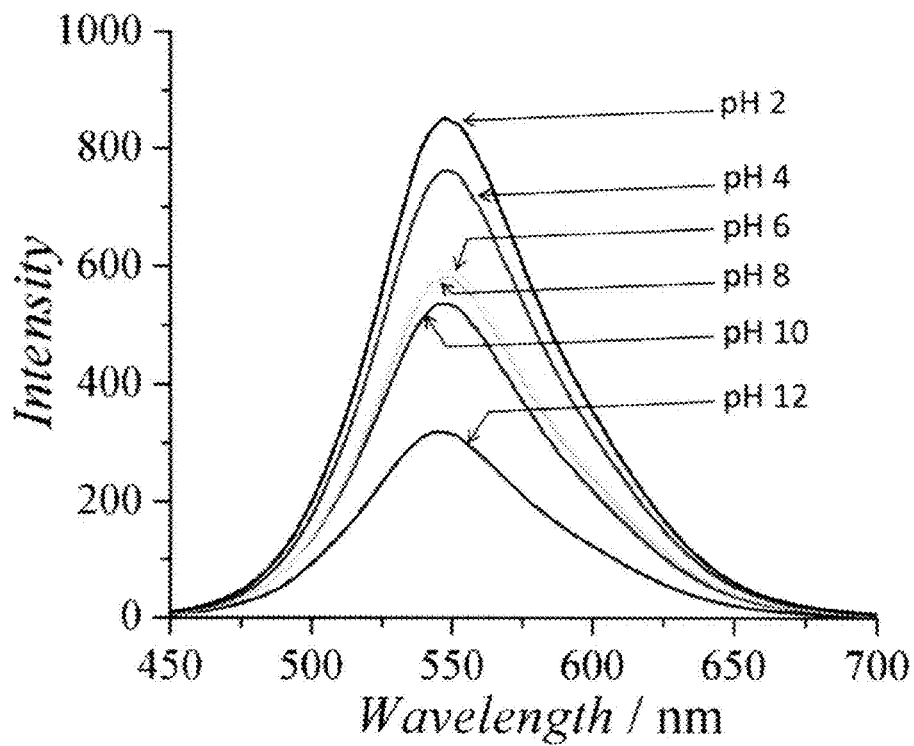

FIG. 12 is a graph showing fluorescence spectra of pCBTh in 20 mM phosphate solution at pH 2 (the bottom line), 4 (second to the bottom line), 6 (third to the bottom line), 8 (third to the top line), 10 (second to the top line) and 12 (the top line).

Figure 13:
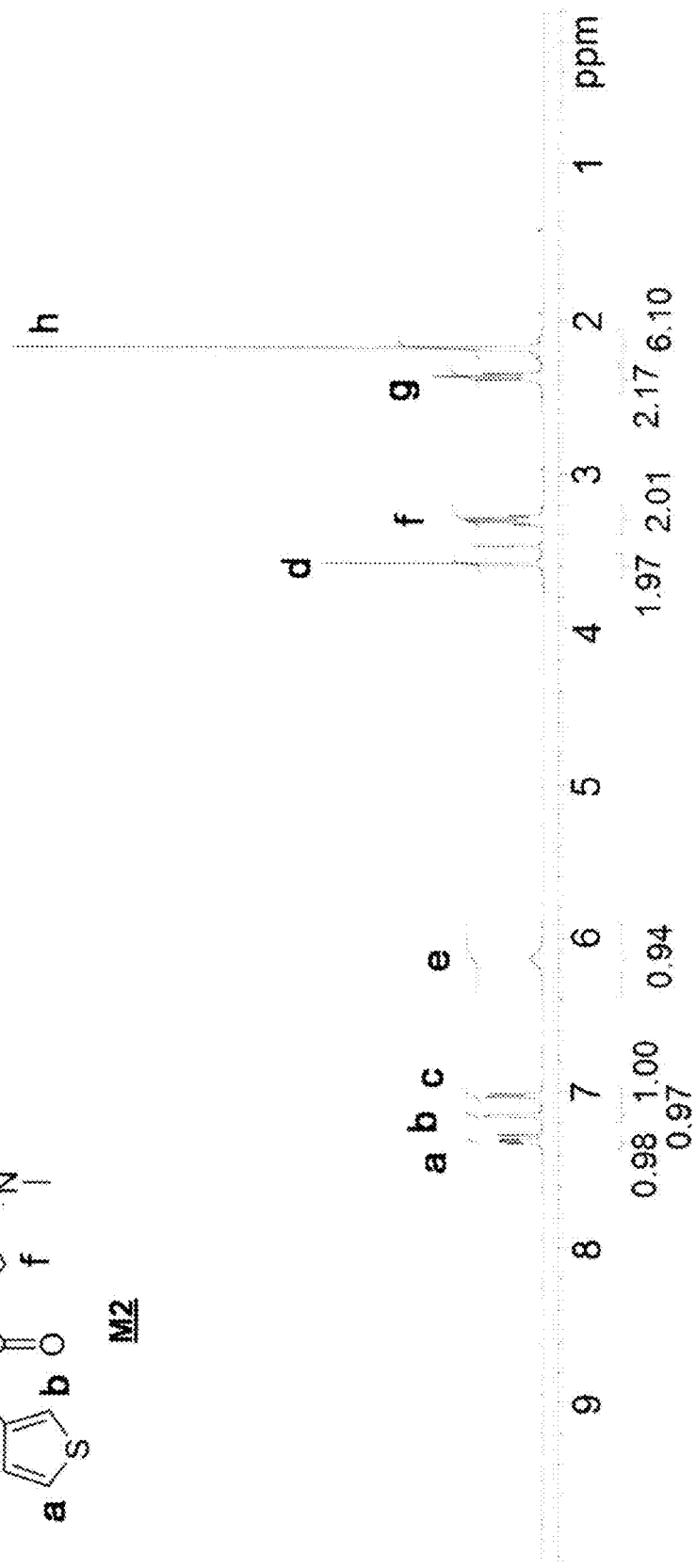

FIG. 13 is a $^1$H NMR spectrum of monomer LXXXIII (M2).

Figure 14:
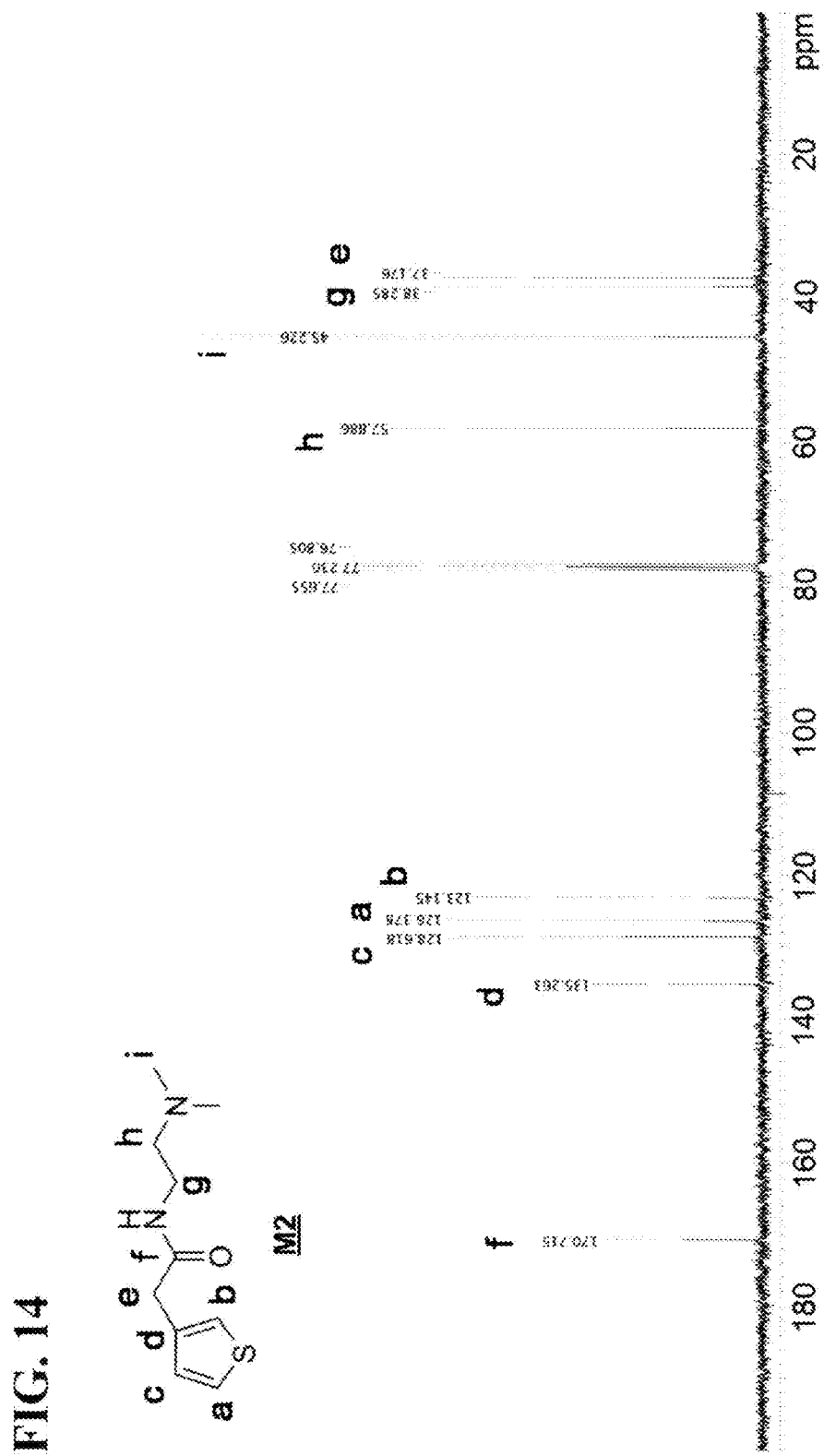

FIG. 14 is a $^{13}$C NMR spectrum of monomer LXXXIII (M2).

Figure 15:
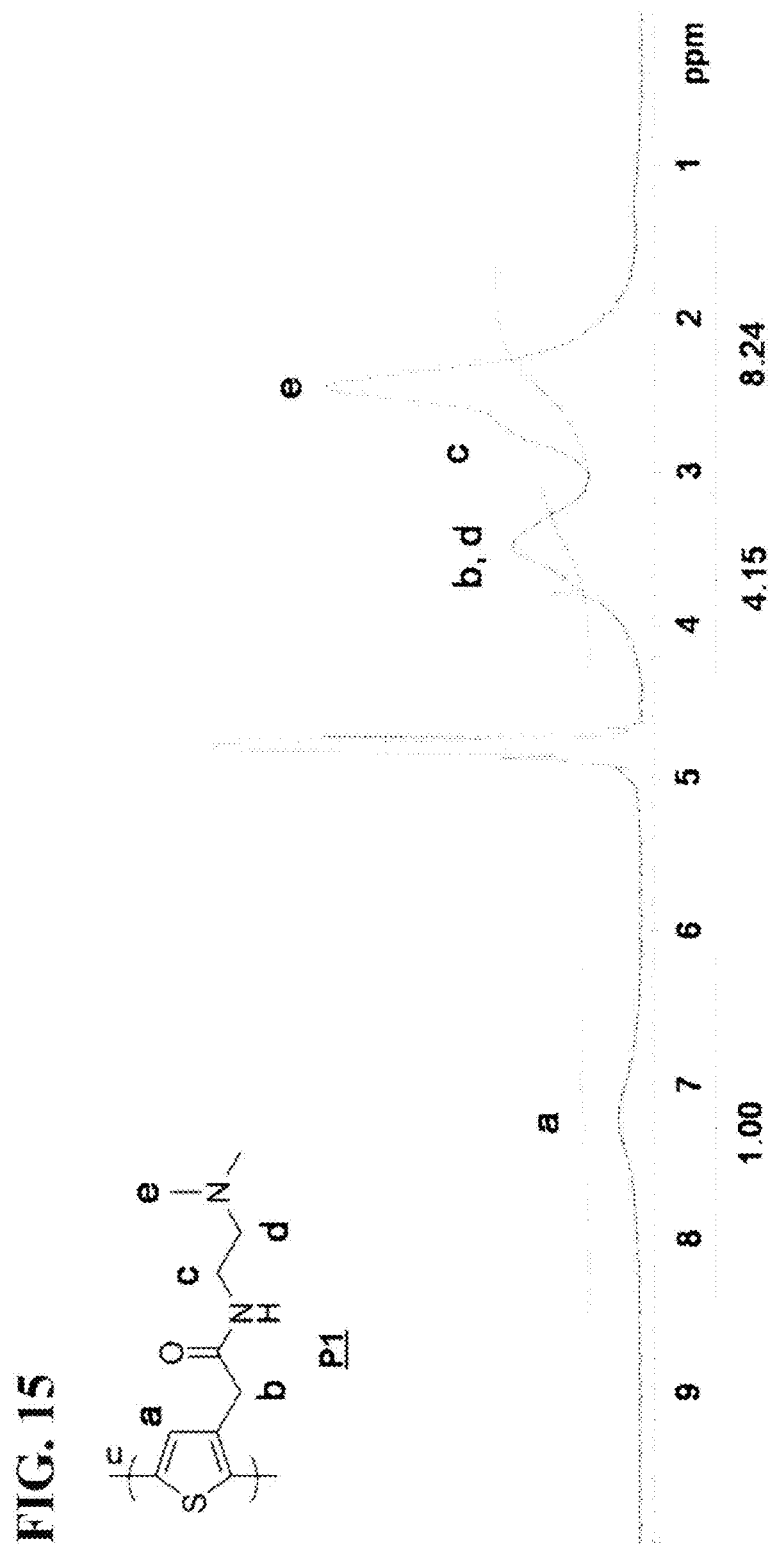

FIG. 15 is a $^1$H NMR spectrum of homo-polymer LXXXIV (P1).

Figure 16:
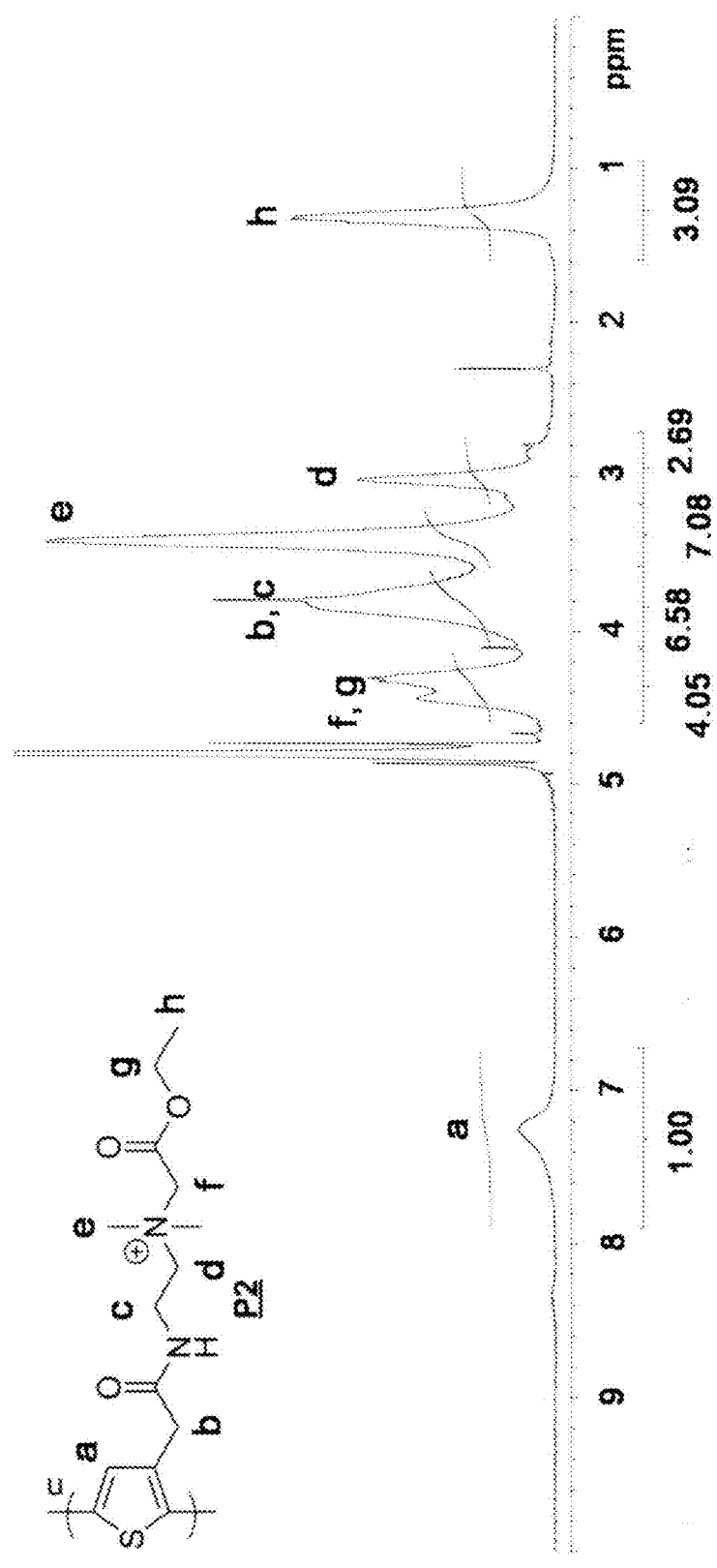

FIG. 16 is a $^1$H NMR spectrum of homo-polymer LXXXV (P2).

Figure 17:
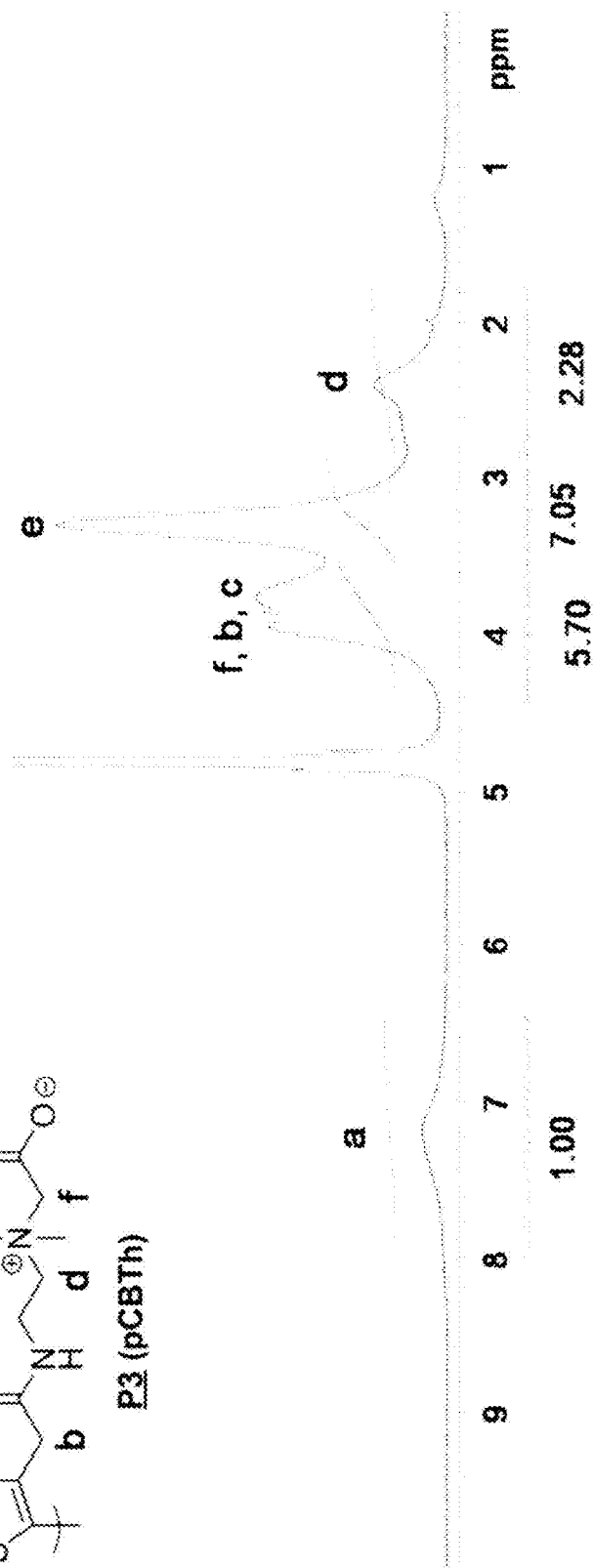

FIG. 17 is a $^1$H NMR spectrum of homo-polymer LIX (P3).

Figure 18:
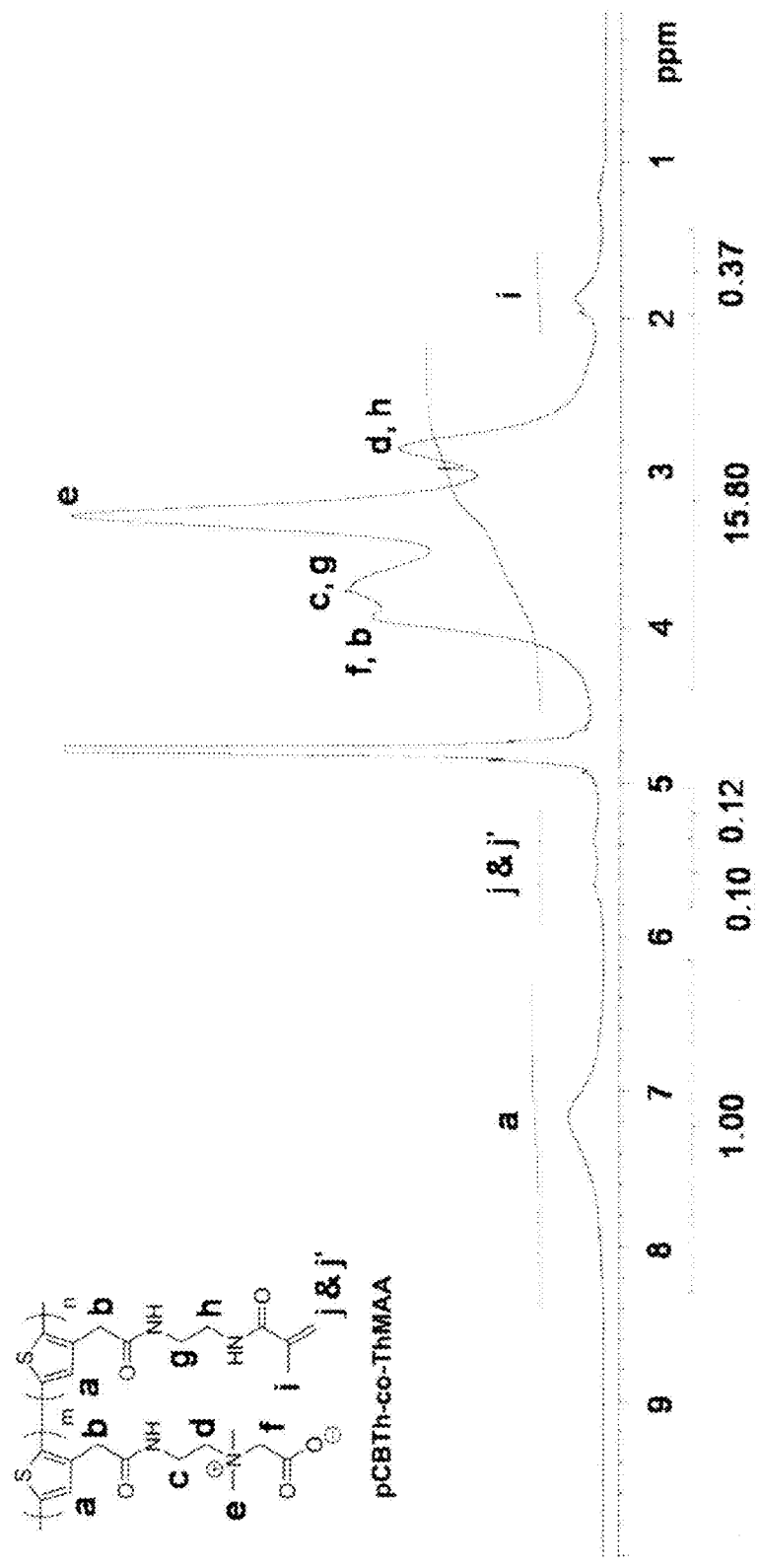

FIG. 18 is a $^1$H NMR spectrum of co-polymer LXI (P7) (pCBTh-co-ThMAA).

Figure 19:
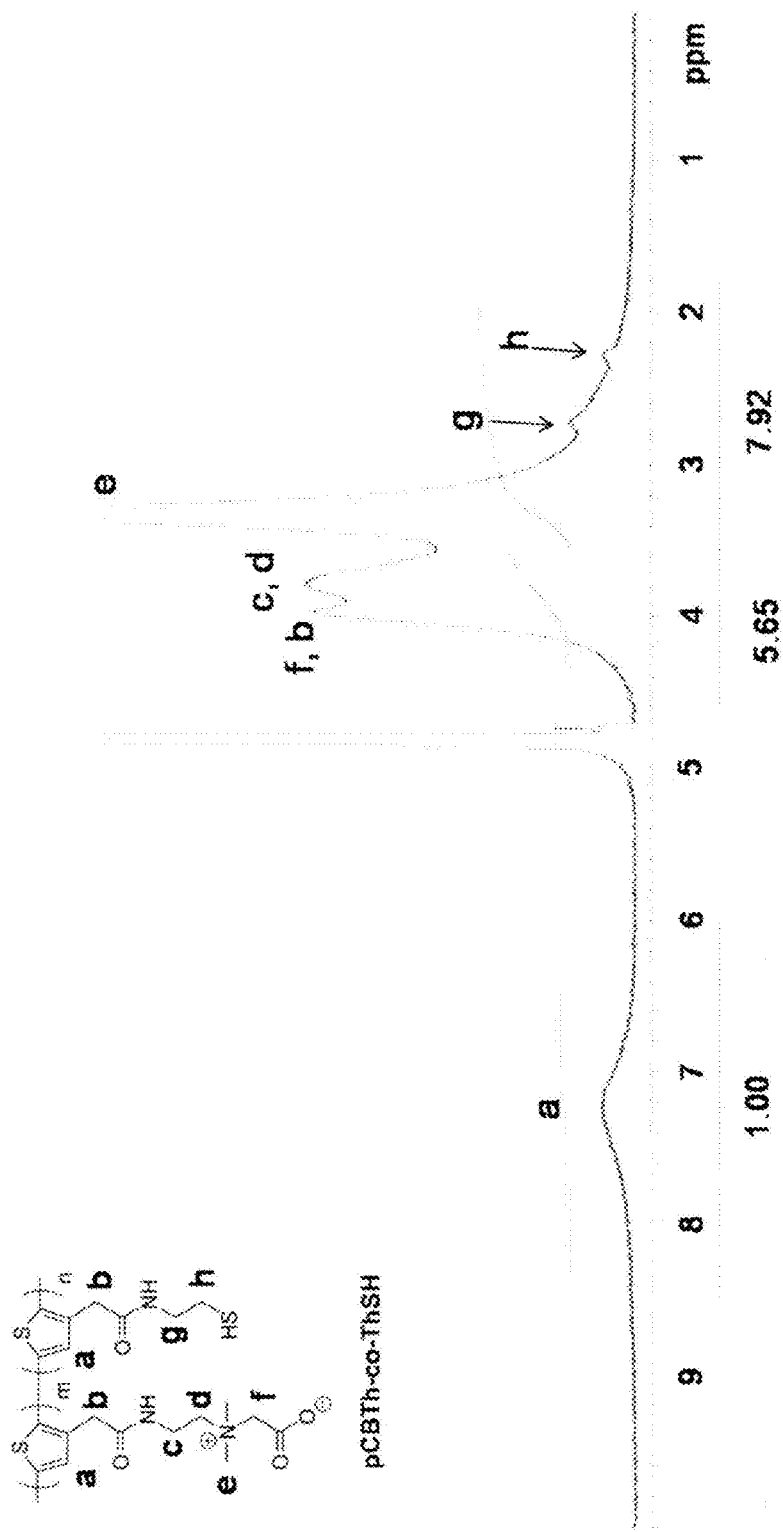

FIG. 19 is a $^1$H NMR of co-polymer LX (P8).

Figure 20:
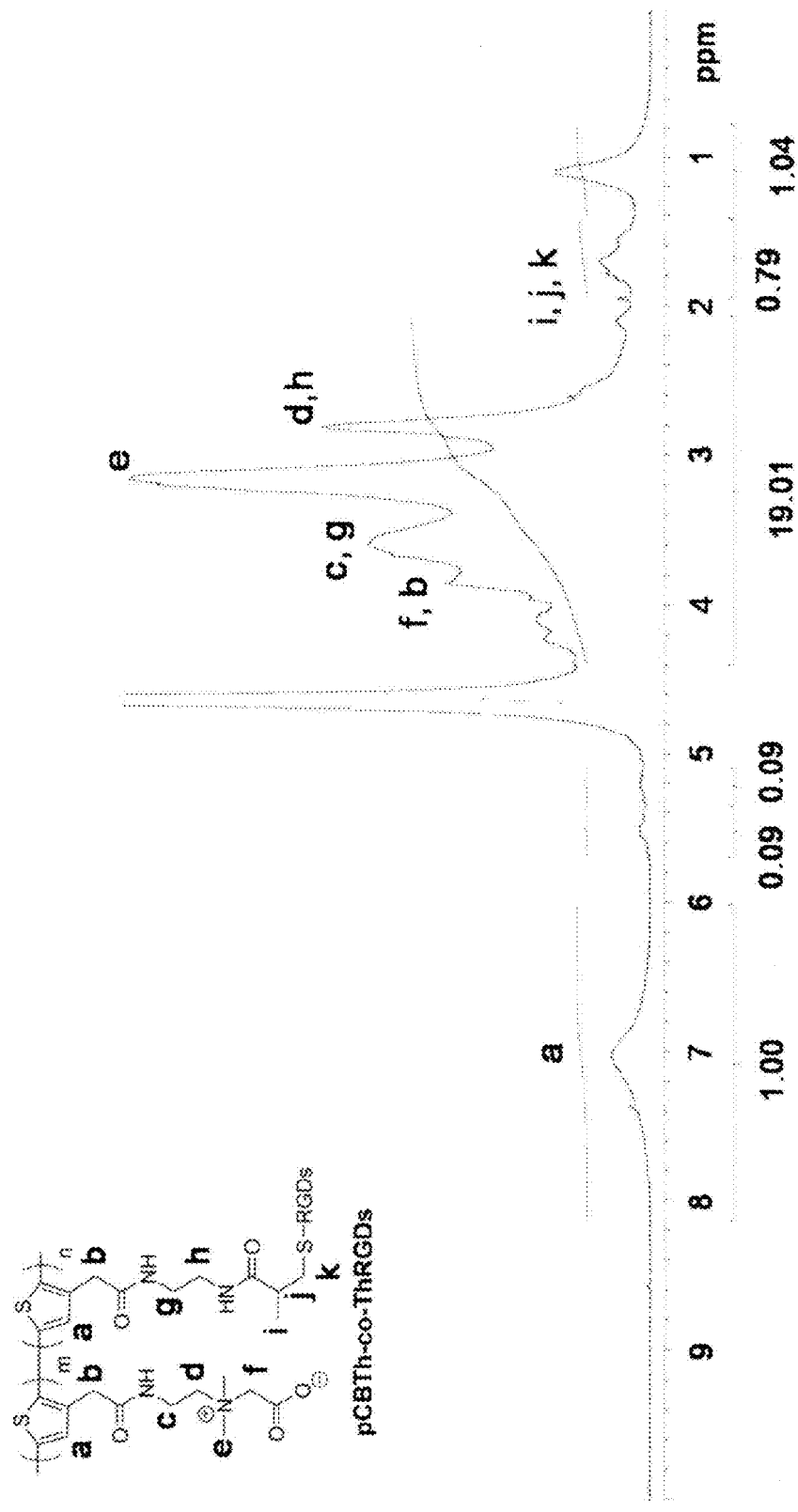

FIG. 20 is a $^1$H NMR of co-polymer pCBTh-co-RGDs.

Figure 21:
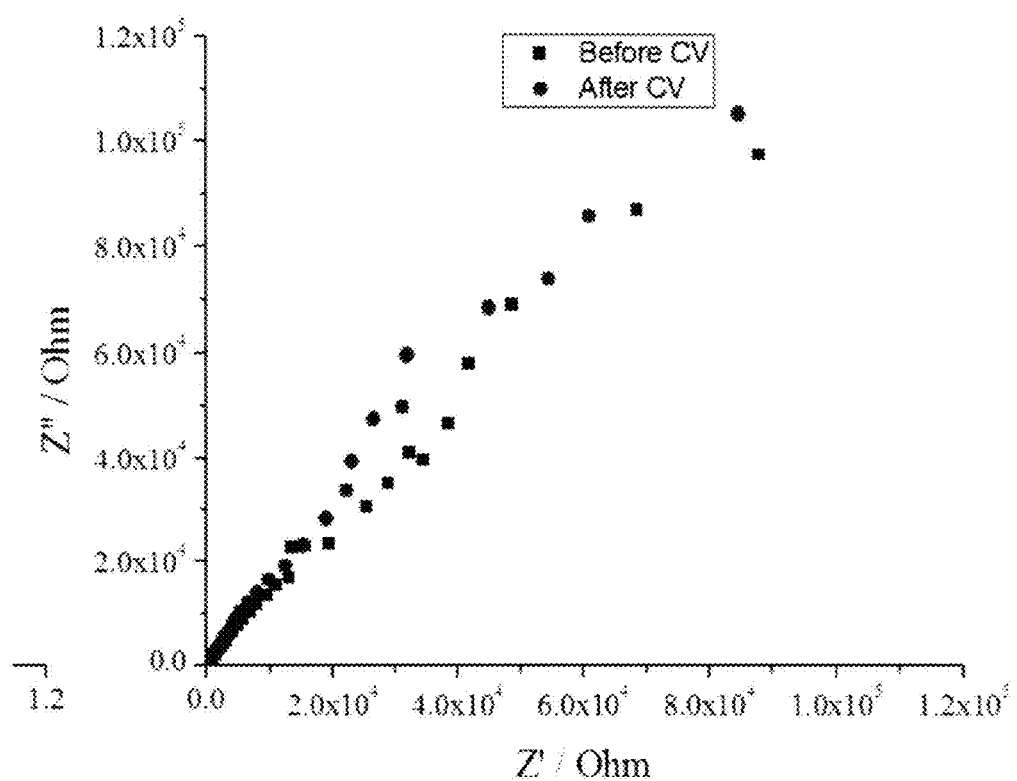

FIG. 21 is a graph an impedance curve of a pCBTh hydrogel electrode before (squares) and after (circles) cyclic voltammetry (CV).

Figure 22:
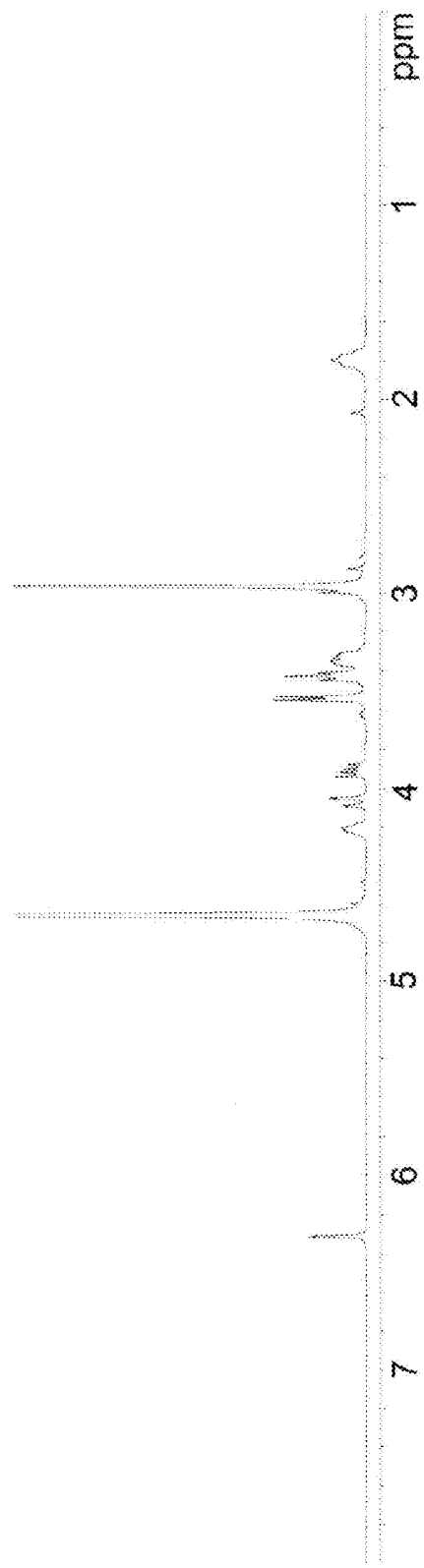

FIG. 22 is a $^1$H NMR of a CB EDOT according to one or more embodiments of the present invention.

DETAILED DESCRIPTION OF THE ILLUSTRATIVE EMBODIMENTS

Embodiments of the present invention are directed to a versatile and high performance zwitterionic CP platform, which integrates many desired functions into one material. Non-conducting zwitterionic materials will gain electronic conductivity through the conducting backbone, and non-biocompatible CPs will obtain excellent biocompatibility, enhanced electrical conductivity, sensitivity to environmental stimuli, functional groups of bioconjugation and tunable mechanical properties via the multifunctional zwitterionic side chains.

Figure 1:
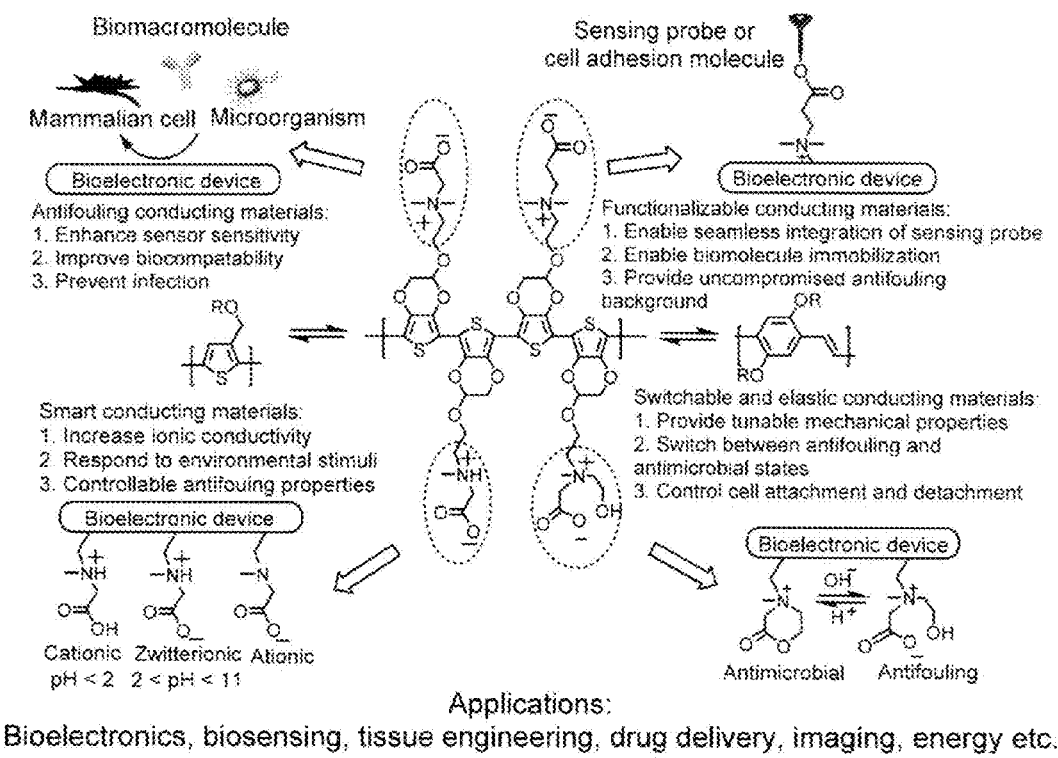
FIG. 1 is a chart outling some of the uses and advantages of embodiments of the present invention.
Figure 2:
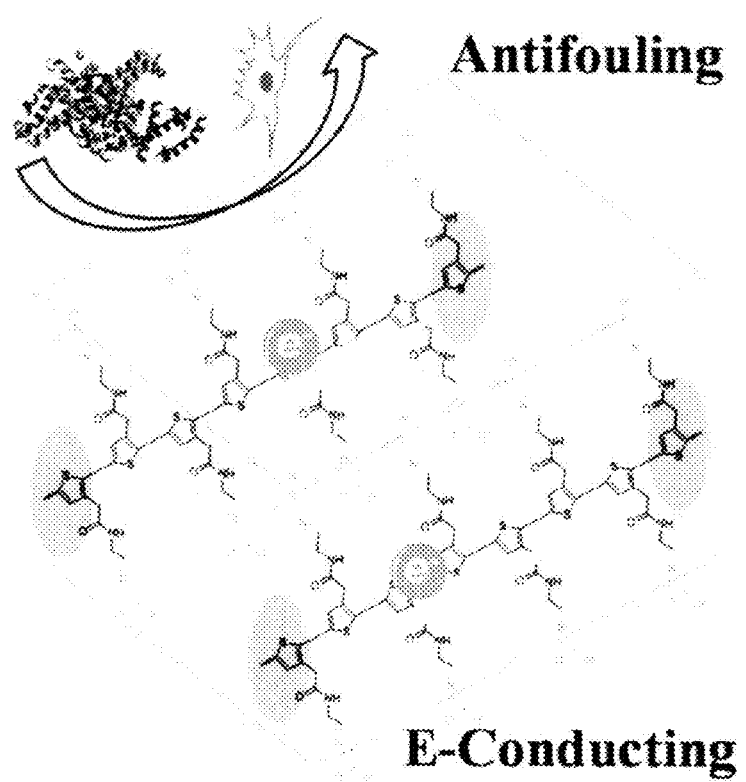
FIG. 2 is a schematic showing a conducting hydrogel according to one or more embodiments of the present invention having a conducting conjugated polymer backbone and multifunctional zwitterionic side chains.

In general outline, the zwitterionic CPs of the present invention have a the conducting polymer backbone and multifunctional zwitterionic side chains. In some embodiments, non-conducting zwitterionic materials gain electronic conductivity through the conducting backbone and CPs obtain excellent biocompatibility, sensitivity to environmental stimuli and controllable antifouling properties via multifunctional zwitterionic side chains. In some embodiments, unique properties from two distinct materials (conducting materials and zwitterionic materials) are integrated into one material without sacrificing any properties. This platform can potentially be adapted for a range of applications (e.g. bioelectronics, tissue engineering, wound healing, robotic prostheses, biofuel cell, etc.), which all require high performance conducting materials with excellent antifouling/biocompatibility at complex biointerfaces. (See FIGS. 1, 2). This conducting material platform will significantly advance the development of conducting polymers in the field of biomedicine and biotechnology.

As used herein, the term "betaine" refers to any neutral chemical compound with positively charged cationic functional group(s) and with negatively charged group(s). The term "carboxybetaine" refers to any neutral chemical compound with positively charged cationic functional group(s) and with negatively charged carboxylate group(s). The term "carboxybetaine-based" therefore refers to the compound containing carboxybetaine moieties. The term "sulfobetaine" refers to any neutral chemical compound with positively charged cationic functional group(s) and with negatively charged sulfonate group(s). The term "phosphobetaine" refers to any neutral chemical compound with positively charged cationic functional group(s) and with negatively charged phosphate group(s).

As used herein, the term "zwitterionic" refers to neutral in electrical charge, which is balanced by positive and negative electrical charges.

As used herein, the term "lactone ring form" "cationic ring form" are used interchangeably to refers to a cyclic structure that has an ester bond and one group is positively charged.

As used herein, the term "hydrogel" refers to a material is a network of polymer chains that are hydrophilic and contain water as the dispersion medium.

As used herein, the term "conjugated polymer" refers to organic macromolecules which consist at least of one backbone chain of alternating double- and single-bonds. As used herein, the term "conjugated polymer platform" refers to a series of conjugated polymers that have similar or related structures, functions and properties.

In a first aspect, embodiments of the present invention are directed to a conjugated polymer platform comprising a conjugated polymer backbone having one or more zwitterionic side chains. The conjugated polymer or polymers that may be used for the conjugated polymer backbone of the present invention are not particularly limited. Suitable conjugated polymer or polymers that may be used for the conjugated polymer backbone of the present invention include, but are not limited to, poly(thiophene)s, poly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide)s, poly(acetylene)s, poly(p-phenylene vinylene)s, and combinations thereof. In some embodiments, the conjugated polymer backbone comprises one or more poly(thiophene)s or poly(3,4-ethylenedioxythiophene)s (pEDOTs).

In some embodiments, polythiophene (pTh) was selected as the electrical conducting conjugated polymer backbone due to its good chemical stability, low redox potential, moderate band gap and optical transparency in its conducting state. In some embodiments, the conjugated polymer backbone comprises poly(3,4-ethylenedioxythiophene) (pEDOT). In some embodiments, pEDOT was selected as the electron conducting conjugated polymer backbone due to its high conductivity and its optical properties.

Chemically bonded to the conjugated polymer backbone are one or more zwitterionic side chains. The zwitterionic side chains of embodiments of the present invention are bonded at one end to the conjugated polymer backbone and contain a zwitterionic functional group. In some embodiments, the zwitterionic side chains are substituted at the 3-, or 3- and 4-positions of the pTh of the conjugated polymer backbone. In some embodiments, zwitterionic functional group may be a betaine group. In some embodiments, the zwitterionic side chains further comprise a carboxybetaine group, a sulfobetaine group and/or a phosphobetaine group. In some embodiments, the zwitterionic functional group may be a carboxybetaine group. In some embodiments, zwitterionic functional group may be a mixture of negatively charged and positive charged groups. In some embodiments, the zwitterionic side chains comprise a carboxybetaine group having at least one ethanol, propanol, butanol or pentanol group bonded to the nitrogen atom of said carboxybetaine group.

In some embodiments, the zwitterionic functional group may be separated from the conjugated polymer backbone by from 1 to 100 carbon, oxygen, nitrogen, or sulfur atoms. In some embodiments, the zwitterionic betaine group may be separated from the conjugated polymer backbone by from 2 to 6 carbon, oxygen, nitrogen or sulfur atoms. In some embodiments, the zwitterionic betaine group may be separated from the conjugated polymer backbone by from 6 to 20 carbon, oxygen, nitrogen, or sulfur atoms. In some embodiments, the zwitterionic betaine group may be separated from the conjugated polymer backbone by from 20 to 40 carbon, oxygen, nitrogen, or sulfur atoms. In some embodiments, the zwitterionic betaine group may be separated from the conjugated polymer backbone by from 40 to 60 carbon, oxygen, nitrogen, or sulfur atoms. In some embodiments, the zwitterionic betaine group may be separated from the conjugated polymer backbone by from 60 to 80 carbon, oxygen, nitrogen, or sulfur atoms. In some embodiments, the zwitterionic betaine group may be separated from the conjugated polymer backbone by from 80 to 100 carbon, oxygen, nitrogen, or sulfur atoms.

In some embodiments, the zwitterionic side chains have the formula:

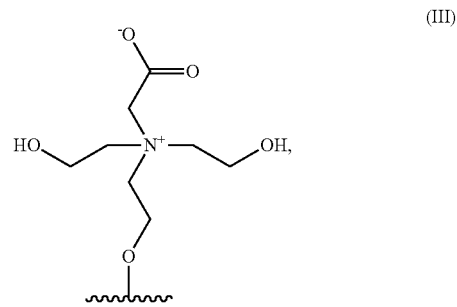

(III)

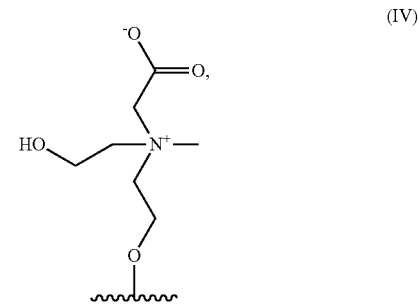

(IV)

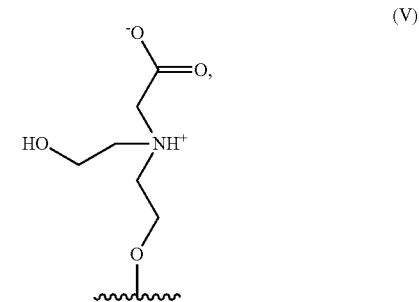

(V)

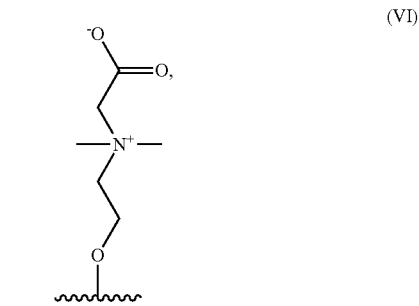

(VI)

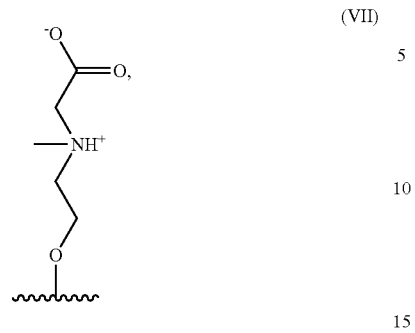
(VII)
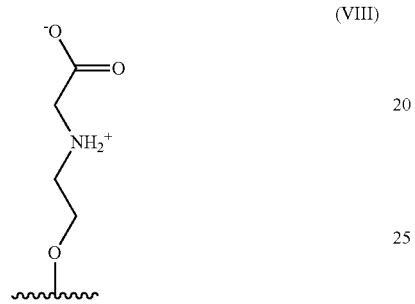
(VIII)
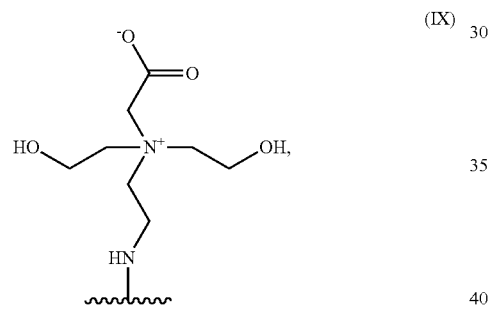
(IX)
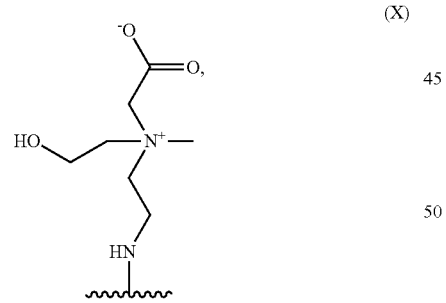
(X)
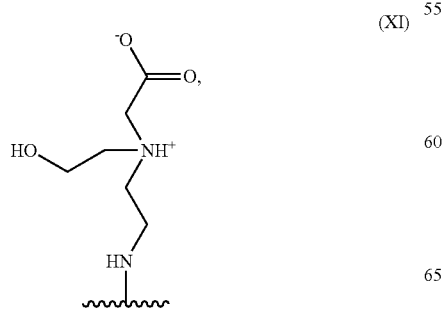
(XI)
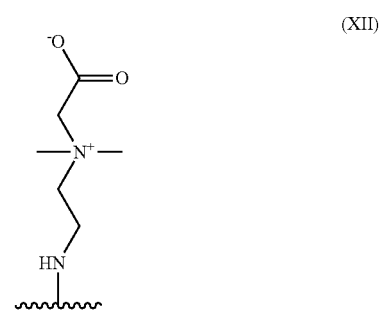
(XII)
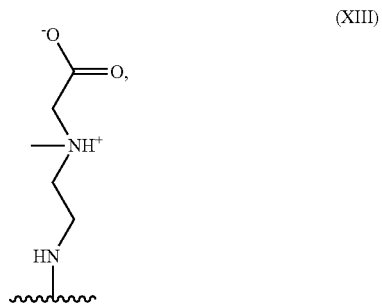
(XIII)
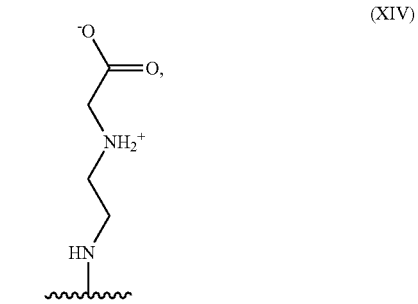
(XIV)
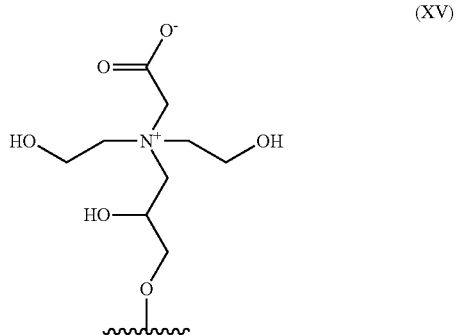
(XV)
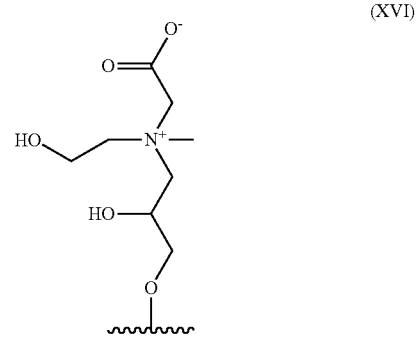
(XVI)

(XVII)

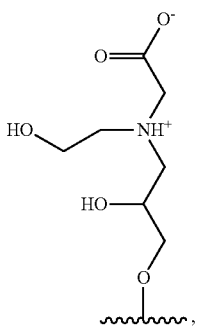

(XVIII)

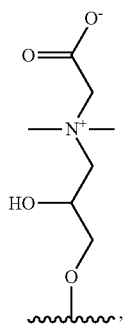

(XIX)

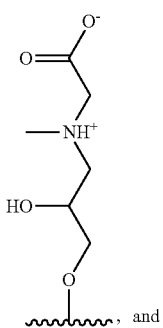

and (XX)

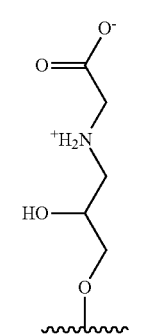

wherein ⌇⌇ the conjugated polymer backbone.

In some embodiments, the zwitterionic side chains have the formula:

(XXI)

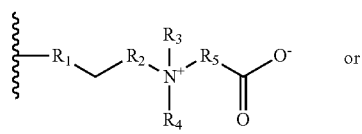 or (XXII)

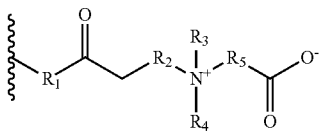

wherein $R_1$ is —O—, —NH—, —C(O)NH—, —$CH_2$C(O)NH—, —$CH_2CH_2$C(O)NH—, —$(CH_2)_m$C(O)NH—, —NHC(O)—, —NHC(O)$CH_2$—, —NHC(O)$CH_2CH_2$—, —NHC(O)$(CH_2)_m$—, —$(CH_2)_m$NHC(O)$(CH_2)_n$—, —$(CH_2)_m$NHC(O)O$(CH_2)_n$—, —$(CH_2)_m$OC(O)NH$(CH_2)_n$—, —$(CH_2)_m$C(O)NH$(CH_2)_n$—, —NHC(O)$(CH_2)_m$C(O)NH—, —OC(O)$(CH_2)_m$C(O)NH—, —O$(CH_2)_m$C(O)NH—, —NHC(O)$(CH_2)_m$O—, —NHC(O)$(CH_2)_m$C(O)O—, —C(O)O—, —$CH_2$C(O)O—, —$CH_2CH_2$C(O)O—, —$(CH_2)_m$C(O)O—, OC(O)—, —OC(O)$CH_2$—, —OC(O)$CH_2CH_2$—, —OC(O)$(CH_2)_m$—, —OC(O)$(CH_2)_m$C(O)O—, —OC(O)$(CH_2)_m$O—, —O$(CH_2)_m$C(O)O—, —$(CH_2)_m$ OC(O)$(CH_2)_n$—, —$(CH_2)_m$C(O)O$(CH_2)_n$—, —$CH_2$O—, —$CH_2CH_2$O—, —$CH_2CH_2CH_2$O—, —$CH_2CH_2CH_2CH_2$O—, —$CH_2CH_2CH_2CH_2CH_2$O—, —$CH_2CH_2CH_2CH_2CH_2CH_2$O—, —$(CH_2)_m$O—, —O$(CH_2)_m$O—, —O$(CH_2)_m$—, —$(CH_2)_m$—, —O$(CH_2CH_2O)_m$, —(O$CH_2CH_2)_m$— or —($CH_2CH_2O)_m$—; $R_2$ is —$CH_2$—, —$CH_2CH_2$—, —$CH_2CH_2CH_2$—, —$CH_2CH_2CH_2CH_2$—, —$CH_2CH_2CH_2CH_2CH_2$—, or —$(CH_2)_{x-1}$—; $R_3$ is H, —$CH_3$, $CH_2CH_3$, —$CH_2CH_2CH_3$, —$CH_2CH_2CH_2CH_3$, —$CH_2CH_2$OH, —$CH_2CH_2CH_2$OH, —$CH_2CH_2CH_2CH_2$OH, or —$CH_2CH_2CH_2CH_2CH_2$OH; $R_4$ is H, —$CH_3$, $CH_2CH_3$, —$CH_2CH_2CH_3$, —$CH_2CH_2CH_2CH_3$, —$CH_2CH_2$OH, —$CH_2CH_2CH_2$OH, —$CH_2CH_2CH_2CH_2$OH, or —$CH_2CH_2CH_2CH_2CH_2$OH; $R_5$ is —$CH_2$—, —$CH_2CH_2$—, —$CH_2CH_2CH_2$—, —$CH_2CH_2CH_2CH_2$—, —$CH_2CH_2CH_2CH_2CH_2$—, —$(CH_2)_y$, or —$(CH_2)_y$O$(CH_2)_z$—; m, n, x, y and z are each an integer from 1 to 20; and ⌇⌇ the conjugated polymer backbone.

In some embodiments, the zwitterionic side chains may have the formula:

(XXIII)

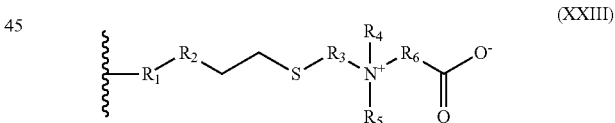

wherein $R_1$ is —O—, —NH—, —C(O)NH—, —$CH_2$C(O)NH—, —$CH_2CH_2$C(O)NH—, —$(CH_2)_m$C(O)NH—, —NHC(O)—, —NHC(O)$CH_2$—, —NHC(O)$CH_2CH_2$—, —NHC(O)$(CH_2)_m$—, —$(CH_2)_m$NHC(O)$(CH_2)_n$—, —$(CH_2)_m$NHC(O)O$(CH_2)_n$—, —$(CH_2)_m$OC(O)NH$(CH_2)_n$—, —$(CH_2)_m$C(O)NH$(CH_2)_n$—, —NHC(O)$(CH_2)_m$C(O)NH—, —OC(O)$(CH_2)_m$C(O)NH—, —O$(CH_2)_m$C(O)NH—, —NHC(O)$(CH_2)_m$O—, —NHC(O)$(CH_2)_m$C(O)O—, —C(O)O—, —$CH_2$C(O)O—, —$CH_2CH_2$C(O)O—, —$(CH_2)_m$C(O)O—, OC(O)—, —OC(O)$CH_2$—, —OC(O)$CH_2CH_2$—, —OC(O)$(CH_2)_m$—, —OC(O)$(CH_2)_m$C(O)O—, —OC(O)$(CH_2)_m$O—, —O$(CH_2)_m$C(O)O—, —$(CH_2)_m$ OC(O)$(CH_2)_n$—, —$(CH_2)_m$C(O)O$(CH_2)_n$—, —$CH_2$O—, —$CH_2CH_2$O—, —$CH_2CH_2CH_2$O—, —$CH_2CH_2CH_2CH_2$O—, —$CH_2CH_2CH_2CH_2CH_2$O—, —$CH_2CH_2CH_2CH_2CH_2CH_2$O—, —$(CH_2)_m$O—, —O$(CH_2)_m$O—, —O$(CH_2)_m$—, —$(CH_2)_m$—, —O(CH$_2$CH$_2$O)$_m$—(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_{x-1}$—, —NHC(O)—, —C(O)NH—, —NHC(O)O—, —NHC(O)CH$_2$—, —NHC(O)CH$_2$CH$_2$—, NHC(O)(CH$_2$)$_x$—, NHC(O)O(CH$_2$)$_x$—, OC(O)NH(CH$_2$)$_x$, OC(O)NH(CH$_2$)$_x$—, —OC(O)—, —OC(O)CH$_2$—, —OC(O)CH$_2$CH$_2$— or —OC(O)(CH$_2$)$_x$—; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_y$—; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_6$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—; —(CH$_2$)$_z$, or —(CH$_2$)$_z$O(CH$_2$)$_v$—; m, n, x, y, z and v are each an integer from 1 to 20; and ~~~ the conjugated polymer backbone.

In some embodiments, the zwitterionic side chains may have the formula:

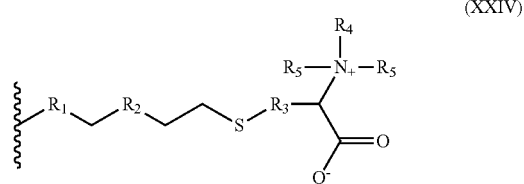

(XXIV)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_{x-1}$—, —NHC(O)—, —NHC(O)CH$_2$—, —NHC(O)CH$_2$CH$_2$—, NHC(O)(CH$_2$)$_x$—, —OC(O)—, —OC(O)CH$_2$—, —OC(O)CH$_2$CH$_2$— or —OC(O))(CH$_2$)$_x$—; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_y$—; R$_4$ is H, —CH$_3$, CH$_2$CH$_3$, —CH$_2$CH$_2$CH$_3$, CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or CH$_2$CH$_2$CH$_2$CH$_2$CH$_2$OH; R$_5$ is H, —CH$_3$, CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH; R$_6$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$CH$_2$OH, or —CH$_2$CH$_2$CH$_2$CH$_2$CH$_2$OH; m, n, x and y are each an integer from 1 to 20; and ~~~ is the conjugated polymer backbone.

In some embodiments, the zwitterionic side chains may have the formula:

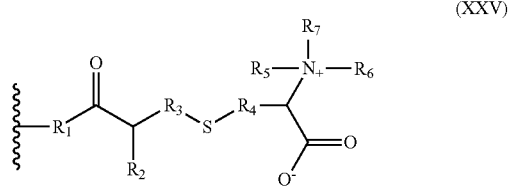

(XXV)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —C(O)NH(CH$_2$)$_n$—, —NHC(O)(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —CH$_2$C(O)O—, —OC(O)CH$_2$—, —OC(O)CH$_2$CH$_2$—, —OC(O)(CH$_2$)$_m$—, —OC(O)(CH$_2$)$_m$O—, —(CH$_2$)$_m$OC(O)(CH$_2$)$_n$—, —(CH$_2$)$_m$C(O)O(CH$_2$)$_n$—, —C(O)O(CH$_2$)$_n$—, —OC(O)(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$—CH$_2$CH$_3$, or —CH$_2$CH$_2$CH$_3$; —R$_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_x$—; R$_4$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_y$—; R$_5$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_6$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_7$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m, n, x and y are each an integer from 1 to 20; and ~~~ is the conjugated polymer backbone.

In some embodiments, the zwitterionic side chains may have the formula:

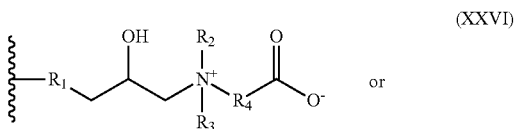

(XXVI)

or

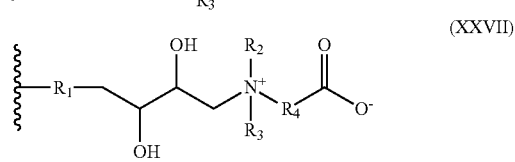

(XXVII)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_{m-1}$, —O(CH$_2$CH$_2$O)$_m$, —(OCH$_2$CH$_2$)$_m$— or —(CH$_2$CH$_2$O)$_m$—; R$_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH, R$_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$— or —(CH$_2$)$_x$O(CH$_2$)$_y$—; m, n, x and y are each an integer from 1 to 20; and ~~~ is the conjugated polymer backbone.

In some embodiments, the zwitterionic side chains have the formula:

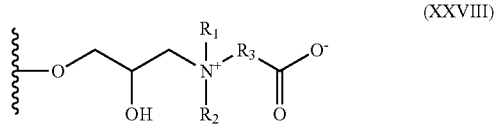

(XXVIII)

wherein R$_1$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, CH$_2$CH$_2$CH$_2$CH$_2$OH, or —CH$_2$CH$_2$CH$_2$CH$_2$CH$_2$OH; R$_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_n$—, or —(CH$_2$)$_m$O(CH$_2$)$_n$—; m and n are each an integer from 1 to 20; and ~~~ is the conjugated polymer backbone.

In some embodiments, the zwitterionic side chains have the formula:

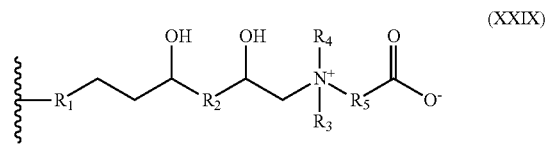

(XXIX)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O) NH—, —NHC(O)(CH$_2$)$_m$O—, —NHC(O)(CH$_2$)$_m$C(O) O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O) CH$_2$CH$_2$—, —OC(O)(CH$_2$)$_m$—; —OC(O)(CH$_2$)$_m$C(O) O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$, CH$_2$CH$_2$—, —CH$_2$CH$_2$CH$_2$—, —CH$_2$CH$_2$CH$_2$CH$_2$—, or —(CH$_2$)$_x$—, R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$—, or —(CH$_2$)$_y$O(CH$_2$)$_z$—; m, n, x, y and z are each an integer from 1 to 20; and ~~~ is the conjugated polymer backbone.

In some embodiments, the zwitterionic side chains have further comprises a zwitterionic moiety selected from the group consisting of 2-(di(methyl)(methylene)ammonio)acetate, 2-((methyl)(methylene)ammonio)acetate, 2-((methylene)ammonio)acetate, 2-(bis(2-hydroxyethyl)(methylene) ammonio)acetate, 2-((2-hydroxyethyl)(methylene)(methyl) ammonio)acetate, 2-((2-hydroxyethyl)(methylene) ammonio)acetate, 3-((methyl)(methylene)ammonio) propanoate, 3-(bi(methyl)(methylene)ammonio)propanoate, 3-(bis(2-hydroxyethyl)(methylene)ammonio)propanoate, 3-((2-hydroxyethyl)(methylene)(methyl)ammonio)propanoate, 3-((2-hydroxyethyl)(methylene)ammonio)propanoate, and/or combinations and analogs/derivatives thereof.

In some embodiments, the zwitterionic side chains have the formula:

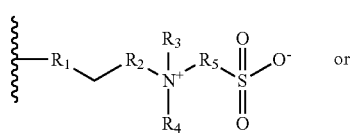

(XXX)

or

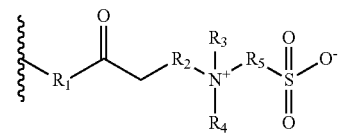

(XXXI)

wherein R$_1$ is —O—, —NH—, —C(O)NH—, —CH$_2$C(O) NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O) NH—, —NHC(O)(CH$_2$)$_m$O—, —NHC(O)(CH$_2$)$_m$C(O) O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O) CH$_2$CH$_2$—, —OC(O)(CH$_2$)$_m$—; —OC(O)(CH$_2$)$_m$C(O) O—, —OC(O)(CH$_2$)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_{x-1}$—; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$CH$_2$—, —CH$_2$CH$_2$CH$_2$—, —CH$_2$CH$_2$CH$_2$CH$_2$—, CH$_2$CH$_2$CH$_2$CH$_2$CH$_2$—, —(CH$_2$)$_y$—, or —(CH$_2$)$_y$O(CH$_2$)$_z$—; m, n, x, y and z are each an integer from 1 to 20; and ∿∿∿ is the conjugated polymer backbone.

In some embodiments, the zwitterionic side chains may have the formula:

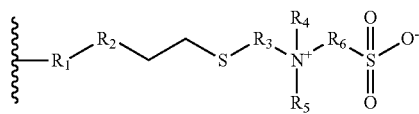

(XXXII)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_{m-1}$—, —O(CH$_2$CH$_2$O)$_m$, —(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—, —NHC(O)—, —NHC(O)CH$_2$—, —NHC(O)CH$_2$CH$_2$—, NHC(O)(CH$_2$)$_x$—, —OC(O)—, —OC(O)CH$_2$—, —OC(O)CH$_2$CH$_2$— or —OC(O))(CH$_2$)$_x$—; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$—; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_6$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_z$—, or (CH$_2$)$_z$O(CH$_2$)$_v$—; m, n, x, y, z and v are each an integer from 1 to 20; and ∿∿∿ is the conjugated polymer backbone.

In some embodiments, the zwitterionic side chains may have the formula:

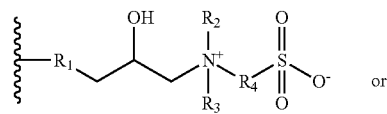

(XXXIII)

or

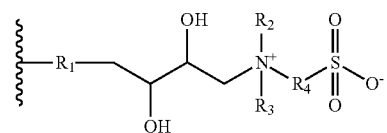

(XXXIV)

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH, R$_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—, or —(CH$_2$)$_y$O(CH$_2$)$_x$—; m, n, x and y are each an integer from 1 to 20; and ∿∿∿ is the conjugated polymer backbone.

In some embodiments, the zwitterionic side chains may have the formula:

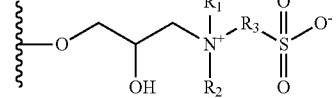

(XXXV)

wherein R$_1$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_n$—, or —(CH$_2$)$_n$O(CH$_2$)$_m$—; m and n are each an integer from 1 to 20; and ∿∿∿ is the conjugated polymer backbone.

In some embodiments, the zwitterionic side chains may have the formula:

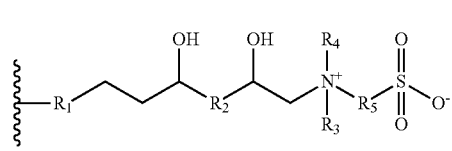

(XXXVI)

wherein $R_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; $R_2$ is —CH$_2$, CH$_2$CH$_2$—, —CH$_2$CH$_2$CH$_2$—, or —CH$_2$CH$_2$CH$_2$CH$_2$—, —(CH$_2$)$_x$—, $R_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$— or —(CH$_2$)$_y$O(CH$_2$)$_z$—; m, n, x, y and z are each an integer from 1 to 20; and ∼∼∼ is the conjugated polymer backbone.

In some embodiments, the zwitterionic side chains may have the formula:

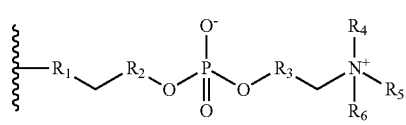

(XXXVII)

wherein —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; $R_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—; $R_3$ is —CH$_2$—, —CH$_2$CH$_2$—, —CH$_2$CH$_2$CH$_2$—, —CH$_2$CH$_2$CH$_2$CH$_2$—, —(CH$_2$)$_y$— or —(CH$_2$)$_y$O(CH$_2$)$_z$—; $R_4$, $R_5$ and $R_6$ are H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m, n, x, y and z are each an integer from 1 to 20, and ∼∼∼ is the conjugated polymer backbone.

Figure 3:
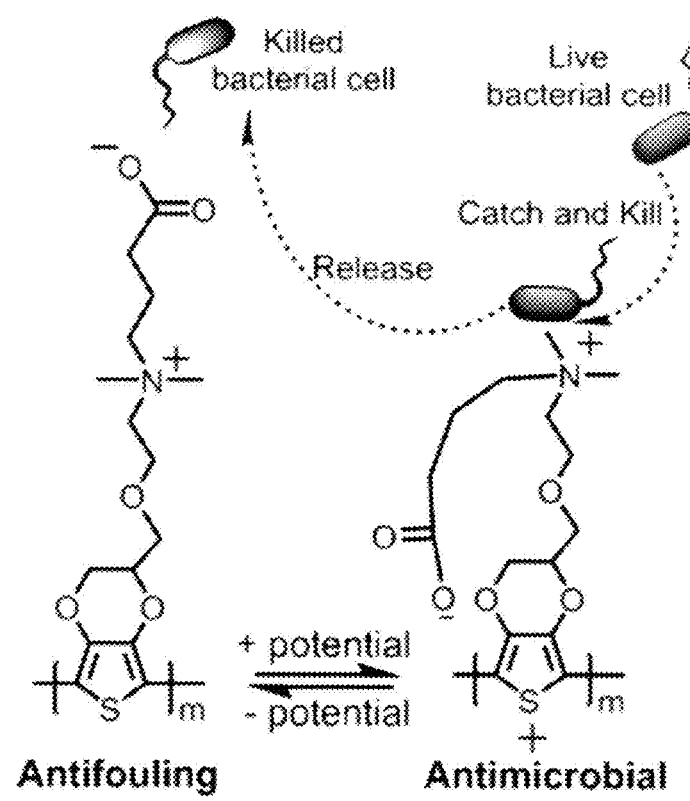
FIG. 3 is a schematic illustration of the switchable antimicrobial mechanism of pCBEDOT via an electro-sensitive pathway.
Figure 4:
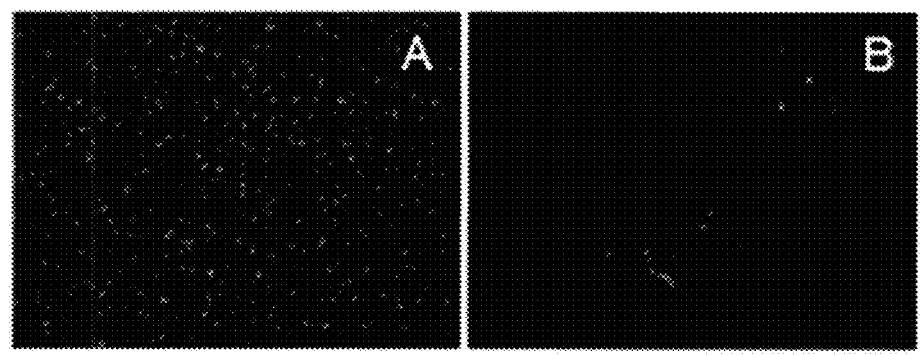
FIGS. 4 A and B are images of the showing the attachment E. Coli K12 cells to CBTh at (A) 0.5V and (B) 0 V.

It has been found that zwitterionic carboxybetaine side chains with hydroxyl group(s) can switch between the corresponding cationic lactone (ring) form (antimicrobial) and the zwitterionic form (antifouling) and the intramolecular hydrogen bonds will enhance the mechanical property of the zwitterionic hydrogel. (See below) Under neutral or basic condition, these materials are in zwitterionic forms with ultralow-fouling property; under acidic conditions, they will automatically convert into cationic charged forms, which have antimicrobial ability. Bacteria can be trapped and killed through contact, then released under neutral or basic environment. (See FIGS. 3, 4). This process is reversible (switchable) by simply changing the acidic/basic environment of the medium.

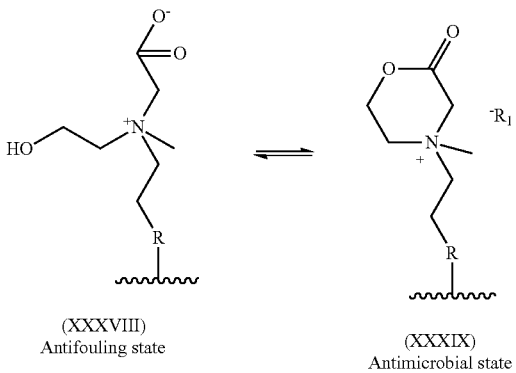

(XXXVIII)
Antifouling state (XXXIX)
Antimicrobial state

In some embodiments, the corresponding cationic lactone (ring) form of the zwitterionic side chains may have the formula:

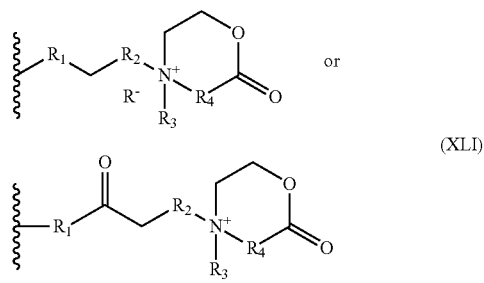

(XL)

or (XLI)

wherein $R_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O) NH—, —NHC(O)(CH$_2$)$_m$O—, —NHC(O)(CH$_2$)$_m$C(O) O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O) CH$_2$CH$_2$—, —OC(O)(CH$_2$)$_m$—, —OC(O)(CH$_2$)$_m$C(O) O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$, CH$_2$CH$_2$—, —CH$_2$CH$_2$CH$_2$—, or —CH$_2$CH$_2$CH$_2$CH$_2$—, —CH$_2$CH$_2$CH$_2$CH$_2$—, or —(CH$_2$)$_{x-1}$—; R$_3$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$— or —(CH$_2$)$_y$O (CH$_2$)$_z$—; R$^-$ is any organic or inorganic anion; m, n, x, y and z are each an integer from 1 to 2; and 〰️ is the conjugated polymer backbone.

In some embodiments, the corresponding cationic lactone (ring) form of the zwitterionic side chains may have the formula:

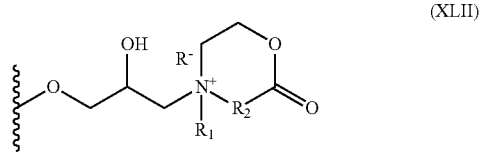

(XLII)

wherein R$_1$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$— or —(CH$_2$)$_y$O(CH$_2$)$_z$—; R$^-$ is any organic or inorganic anion; y and z are each an integer from 1 to 20; and 〰️ is the conjugated polymer backbone.

In some embodiments, the corresponding cationic lactone (ring) form of the zwitterionic side chains may have the formula:

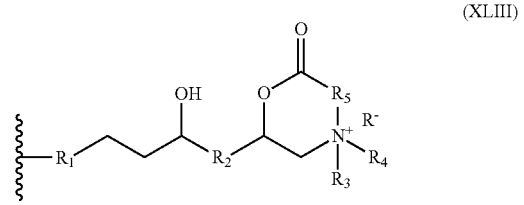

(XLIII)

wherein R$_1$ is —O—, —NH—, —C(O)NH—, —CH$_2$C(O) NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O) NH—, —NHC(O)(CH$_2$)$_m$O—, —NHC(O)(CH$_2$)$_m$C(O) O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O) CH$_2$CH$_2$—, —OC(O)(CH$_2$)$_m$—, —OC(O)(CH$_2$)$_m$C(O) O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$, CH$_2$CH$_2$—, —CH$_2$CH$_2$CH$_2$—, or —CH$_2$CH$_2$CH$_2$CH$_2$—; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—, —(CH$_2$)$_y$— or —(CH$_2$)$_y$O (CH$_2$)$_z$—; m, n, y and z are each an integer from 1 to 20; and 〰️ is the conjugated polymer backbone.

In some embodiments, the corresponding cationic lactone (ring) form of the zwitterionic side chains may have the formula:

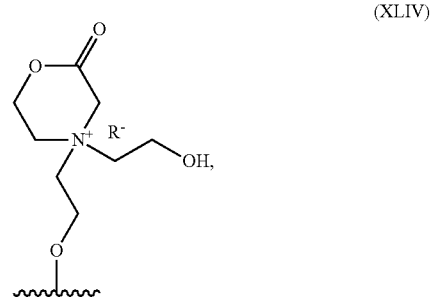

(XLIV)

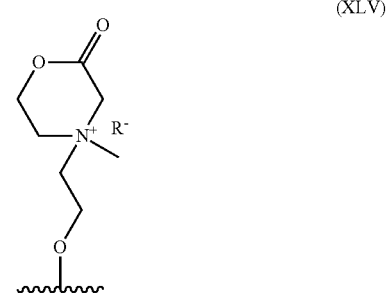

(XLV)

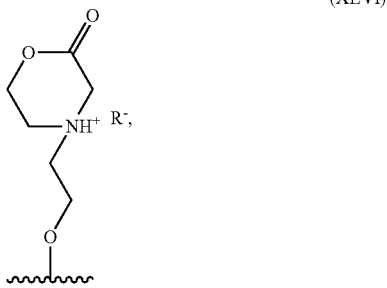

(XLVI)

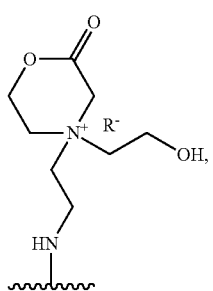
(XLVII)
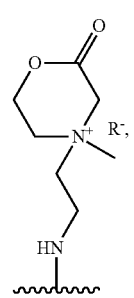
(XLVIII)
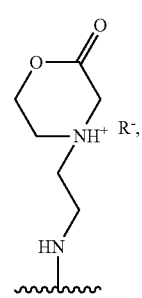
(XLIX)
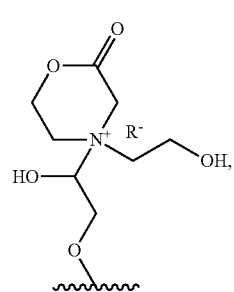
(L)
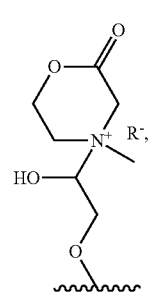
(LI)
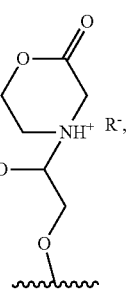
(LII)
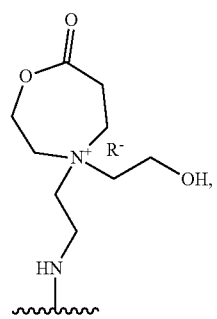
(LIII)
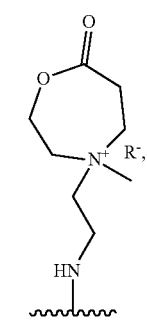
(LIV)
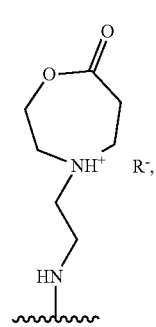
(LV)
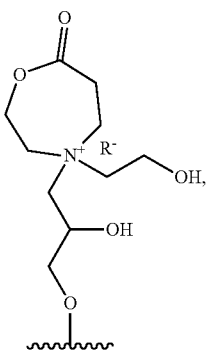
(LVI)

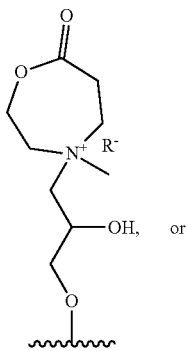

(LVII)

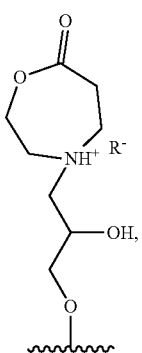

(LVIII)

wherein R is any organic or inorganic anion; and ~~~ is the conjugated polymer backbone.

In some embodiments, the conjugated polymer platform of the present invention may comprise one or more crosslinking side chains. Like the zwitterionic side chains discussed above, the crosslinking side chains in these embodiments are bound to the conjugated polymer backbone. These side groups have a crosslinking moiety capable of bonding either to another crosslinking side chain or to the conjugated polymer backbone to crosslink the polymer to form a polymer network. Suitable functional groups for use as part of the crosslinking side chains include, without limitation, acrylates, acrylamides, or combinations thereof. In some embodiments, the crosslinking moiety of the one or more crosslinking side chains may comprises an acrylate, methacrylate, ethylacrylate, acrylamide, methacrylamide, or ethylacrylamide group.

In some embodiments, crosslinkable moieties may be added to the existing side chains and then crosslinked to form a polymer network and/or hydrogel. Suitable crosslinkable moieties may include, without limitation, a multi-arm-thiols, acrylate, methacrylate, ethylacrylate, acrylamide, methacrylamide, ethylacrylamide, alkene, alkyne, epoxide, azide, aldehyde and/or combinations thereof.

In some embodiments, the conjugated polymer platform of the present invention may comprise a crosslinked polymer network. In some embodiments, the conjugated polymer platform of the present invention may comprise a hydrogel. It should be appreciated, moreover, that in one or more embodiments of the present invention, side chains with one or more free thiol groups (discussed below as a type of "attachment side chain" and as "redox sensitive side chains") may also function as reversible crosslinkers to form a redox sensitive hydrogel. In these embodiments, the free thiol groups on these side chains react with each other to form S—S bonds that crosslink the polymer to form a redox sensitive hydrogel, as discussed below.

Figure 5:
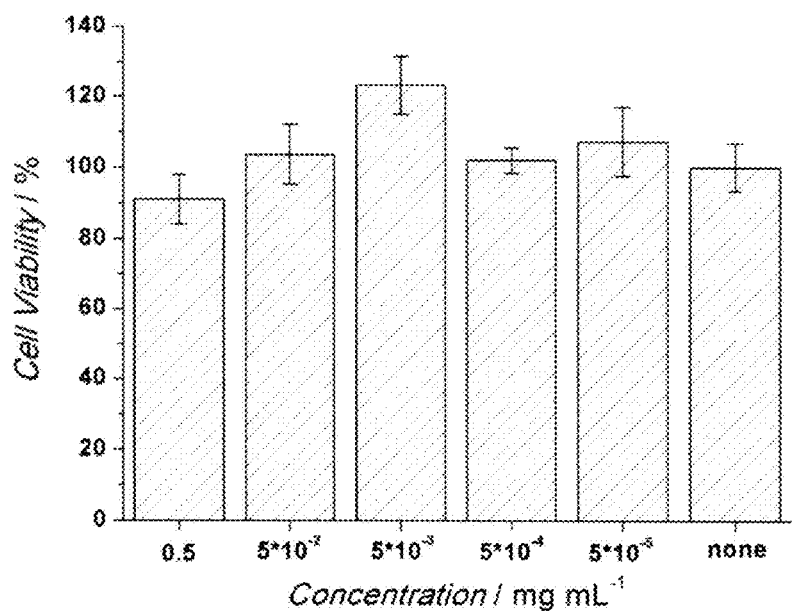
FIG. 5 is a representative cytotoxicity assay of BAECs treated with a series of dilutions of pCBTh polymer in culture media, expressed as a percentage of control untreated cells.

CP hydrogels according to one or more embodiments of the present invention are of great interest for biomedical and biotech applications, since they not only provide a favorable electrical conducting environments but also a high level of hydration and similarity to tissues. In some embodiments, pCBTh-co-ThMAA hydrogels have a much high water content (96.3%) than the control pThAA hydrogels (80.4%) and it is believed that zwitterionic carboxybetaine side chains dramatically increase the water solubility of the conjugated polymer backbone. The polymerizable macromonomers have distinct advantages over small monomers for hydrogel synthesis, since they are less toxic to cells compared to highly reactive small monomers and crosslinkers. It has been found that the soluble pCBTh polymer has low cytotoxicity at various concentrations (See FIG. 5).

In some embodiments, the conjugated polymer platform further comprises one or more side chains for securing said conjugated polymer platform to a surface. These side groups are bound at suitable position(s) on the conjugated polymer backbone like the zwitterionic side chains and crosslinking side chains discussed above, and have one or moieties capable of securing the conjugated polymer platform to a surface. Suitable moieties capable of securing the conjugated polymer platform to a surface may include, without limitation, thiols, ethoxysilanes, methoxysilanes, chlorosilanes, alkyl phosphates, 3,4-dihydroxyphenylalanine, and/or combinations thereof. In some embodiments, the attachment moiety may include, without limitation, cystamine, cysteine, 1-ethanol-2-thiol, (3-aminopropyl)triethoxysilane, (3-aminopropyl)trimethoxysilane, 3,4-dihydroxyphenethylamine, 12-hydroxy dodecyl phosphate, 2-aminoethylphosphonic acid, 3-aminopropylphosphonic acid, 4-aminobutylphosphonic acid, 2-hydrxylethylphosphonic acid, 3-hydrxylpropylphosphonic acid, 4-hydrxylbutylphosphonic acid, and combinations thereof.

In some embodiments, the conjugated polymer platform of the present invention may have the formula:

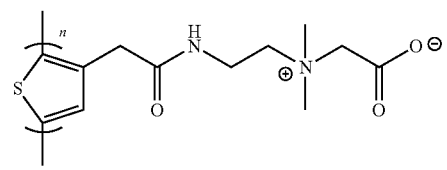

(LIX)

wherein n is an integer from 1 to 10,000,000.

In some embodiments, the conjugated polymer platform of the present invention may have the formula:

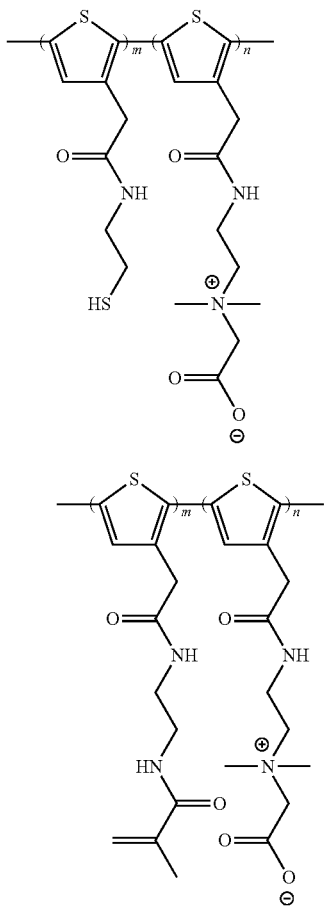

(LX)

(LXI)

wherein m is an integer from 1 to 10,000,000 and n is an integer from 1 to 10,000,000.

In a second aspect, embodiments of the present invention are directed to a redox sensitive hydrogel comprising a conjugated polymer backbone described above, having one or more redox sensitive side chains. As set forth above, these redox sensitive side chains may comprise one or more available (free) thiol groups, which function as reversible crosslinkers to form the redox sensitive hydrogel. In these embodiments, the free thiol groups on these side chains react with each other to form disulfide bonds that crosslink the polymer to form a hydrogel. These crosslinks are both reversible and redox sensitive. As will be appreciated by those of skill in the art, these cross links will form and break apart based upon the oxidation/reduction environment. That is, oxidation causes the SH (thiol) bond to break and the disulfide (S—S) crosslink bonds to form and, conversely, reduction causes the disulfide (S—S) crosslink bonds to break and the SH (thiol) bonds to reform.

Further, the redox sensitive hydrogel of embodiments of the present invention may also comprise zwitterionic side chains and crosslinking side chains as described above. In some embodiments, pendant methacrylamide (MAA) groups on the pCBTh-co-ThMAA-co-ThSH above may also bond with each other or said conjugated polymer backbone further crosslinking the redox sensitive hydrogel.

Moreover, in some embodiments, the redox sensitive hydrogels of the present invention avoid the crosslinking problems of prior systems described above. In these embodiments, all functional groups are integrated into the polymer chain to form a chemically crosslinked hydrogel network. It should also be appreciated that the porous structure of pCBTh-co-ThMAA or pCBTh-co-ThSH hydrogels of embodiments of the present invention have a high surface area that is highly favorable for electrochemical processes, which in many cases require both ionic and electronic transport. In some embodiments, the zwitterionic side chains discussed above may enhance the conductivity of materials, since they can affect the self-ionization of water and subsequently facilitate the ionic conductivity. The zwitterionic side chains of redox sensitive hydrogels according to embodiments of the present invention may also endow them with superior antifouling properties and can resist protein adsorption on their surfaces without compromising electrical conductivity.

The conjugated polymer backbone for these redox sensitive hydrogels may be the same as for the conjugated polymer platform described above. In some embodiments, the conjugated polymer backbone of the redox sensitive hydrogel may comprise poly(thiophene)s, oly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide)s, poly(acetylene)s, poly(p-phenylene vinylene)s, or any combinations thereof. In some embodiments, the conjugated polymer backbone of the redox sensitive hydrogel may comprise polythiophene or pEDOT.

The zwitterionic side chains of the redox sensitive hydrogels may include any of the zwitterionic side chains described above with respect to the conjugated polymer platform embodiments of the present invention. In some embodiments, the zwitterionic side chains of the redox sensitive hydrogel may comprise a carboxybetaine group, a sulfobetaine group or a phosphobetaine group. In some embodiments, the zwitterionic side chains of the redox sensitive hydrogel may comprise a carboxybetaine group. In some embodiments, the zwitterionic side chains of the redox sensitive hydrogel may comprise a carboxybetaine group having at least one ethanol, propanol, butanol or pentanol group bonded to the nitrogen atom of said carboxybetaine group.

In some embodiments, the redox sensitive hydrogels may include any of the crosslinking side chains described above with respect to the conjugated polymer platform embodiments of the present invention. As set forth above, with respect to the conjugated polymer platform embodiments of the present invention, the crosslinking side chains in these embodiments are bound to the conjugated polymer backbone and have a crosslinking moiety capable of bonding either to another crosslinking side chain or to the conjugated polymer backbone to crosslink the polymer. Suitable functional groups for use as part of the crosslinking side chains include, without limitation, acrylates, acrylamides, or combinations thereof. In some embodiments, the crosslinking moiety of the one or more crosslinking side chains may comprises an acrylate, methacrylate, ethylacrylate, acrylamide, methacrylamide, or ethacrylamide group.

In a third aspect, embodiments of the present invention are directed to a zwitterionic monomer for use in forming a conjugated polymer platforms and/or redox sensitive hydrogels described above. These zwitterionic monomers have a thiophene or 3,4-ethylenedioxythiophene (EDOT) group and a zwitterionic carboxybetaine, sulfobetaine or phosphobetaine group. In some embodiments, the zwitterionic carboxybetaine group comprises at least one ethanol, propanol, butanol or pentanol group bonded to the nitrogen atom of said carboxybetaine group.

It should be appreciated that when polymerized form the conjugated polymer platform and/or redox sensitive hydrogel described above, the thiophene or EDOT portion of the zwitterionic monomer will form the conjugated polymer backbone portion of the conjugated polymer platform and/or redox sensitive hydrogel and the remainder of the zwitterionic monomer will form the zwitterionic side chain portion of the conjugated polymer platform and/or redox sensitive hydrogel. Therefore, in some embodiments, the portion of the zwitterionic monomers of the present invention attached to the thiophene or EDOT group (and including the zwitterionic carboxybetaine, sulfobetaine, phosphobetaine or mixed charged groups) may be the same as any of the zwitterionic side chains described above.

In some embodiments, the zwitterionic carboxybetaine, sulfobetaine or phosphobetaine group may be separated from the thiophene or EDOT group by from 1 to 50 carbon, oxygen, nitrogen, or sulfur atoms. In some embodiments, the zwitterionic carboxybetaine, sulfobetaine or phosphobetaine group may be separated from the thiophene or EDOT group by from 2 to 30 carbon, oxygen, nitrogen, or sulfur atoms. In some embodiments, the zwitterionic carboxybetaine, sulfobetaine or phosphobetaine group may be separated from the bifunctional thiophene or EDOT group by from 2 to 20 carbon, oxygen, nitrogen, or sulfur atoms. In some embodiments, the zwitterionic carboxybetaine, sulfobetaine or phosphobetaine group may be separated from the bifunctional thiophene or EDOT group by from 3 to 15 carbon, oxygen, nitrogen, or sulfur atoms. In some embodiments, the zwitterionic carboxybetaine, sulfobetaine or phosphobetaine group may be separated from the bifunctional thiophene or EDOT group by from 5 to 10 carbon, oxygen, nitrogen, or sulfur atoms.

In some embodiments, the zwitterionic carboxybetaine groups of the zwitterionic polymers of the present invention may have one or more with hydroxyl group(s). As set forth above, in some embodiments these zwitterionic carboxybetaine groups can switch between the corresponding cationic lactone (ring) form (antimicrobial) and the zwitterionic form (antifouling) and the intramolecular hydrogen bonds will enhance the mechanical property of the conjugated polymer platforms and/or redox sensitive hydrogels described above. (See FIGS. 1-3)

In some embodiments, the zwitterionic monomer of the present invention may have the formula:

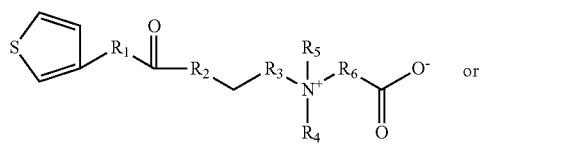

(LXII)

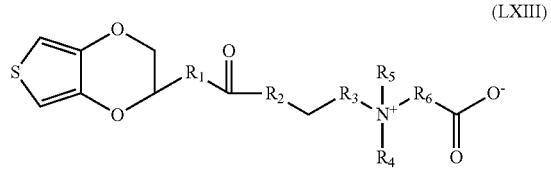

(LXIII)

wherein $R_1$ is —O—, —NH—, —CH$_2$NH—, —CH$_2$CH$_2$NH—, —(CH$_2$)$_m$NH—, —NHC(O)CH$_2$—, —NHC(O)CH$_2$CH$_2$—, —NHC(O)(CH$_2$)$_m$—, —(CH$_2$)$_m$NHC(O)(CH$_2$)$_{n+1}$—, —(CH$_2$)$_{m+1}$NHC(O)O(CH$_2$)$_n$—, —(CH$_2$)$_m$OC(O)NH(CH$_2$)$_n$—, —(CH$_2$)$_n$C(O)NH(CH$_2$)$_n$—, —NHC(O)(CH$_2$)$_m$O—, —OC(O)CH$_2$—, —OC(O)CH$_2$CH$_2$—, —OC(O)(CH$_2$)$_m$—, —OC(O)(CH$_2$)$_m$O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$—, —(OCH$_2$CH$_2$)$_m$— or —(CH$_2$CH$_2$O)$_m$—; $R_2$ is —O—, —NH, —CH$_2$C(O)NH—, —CH$_2$CH$_2$C(O)NH—, —(CH$_2$)$_x$C(O)NH—, —NHC(O)—, —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$NHC(O)O(CH$_2$)$_y$—, —(CH$_2$)$_x$OC(O)NH(CH$_2$)$_y$—, —(CH$_2$)$_x$C(O)NH(CH$_2$)$_y$—, NHC(O)(CH$_2$)$_x$C(O)NH—, —O(CH$_2$)$_x$C(O)NH—, —NHC(O)(CH$_2$)$_x$O—, —NHC(O)(CH$_2$)$_x$C(O)O—, —CH$_2$C(O)O—, —CH$_2$CH$_2$C(O)O—, —(CH$_2$)$_m$C(O)O—, —O(CH$_2$)$_x$C(O)O—, —(CH$_2$)$_x$OC(O)(CH$_2$)$_y$—, —(CH$_2$)$_x$C(O)O(CH$_2$)$_y$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —(CH$_2$)$_x$O—, —O(CH$_2$)$_x$O—, —O(CH$_2$)$_x$—, —(CH$_2$)$_x$—, —O(CH$_2$CH$_2$O)$_x$, —(OCH$_2$CH$_2$)$_x$— or —(CH$_2$CH$_2$O)$_x$—; $R_3$ is —CH$_2$—, —CH$_2$CH$_2$—, —CH$_2$CH$_2$CH$_2$—, —CH$_2$CH$_2$CH$_2$CH$_2$—, CH$_2$CH$_2$CH$_2$CH$_2$CH$_2$— or —(CH$_2$)$_{z-1}$—; $R_4$ is —H, —CH$_3$, —CH$_2$CH$_3$, —CH$_2$CH$_2$CH$_3$, —CH$_2$CH$_2$CH$_3$, —CH$_2$CH$_2$OH, —CH$_2$CH$_2$CH$_2$OH, —CH$_2$CH$_2$CH$_2$CH$_2$OH; $R_5$ is —H, —CH$_3$, —CH$_2$CH$_3$, —CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and $R_6$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_v$— or —(CH$_2$)$_v$O(CH$_2$)$_v$—; and m, n, x, y, z v and w are each an integer from 1 to 20.

In some embodiments, the zwitterionic monomer of the present invention may have the formula:

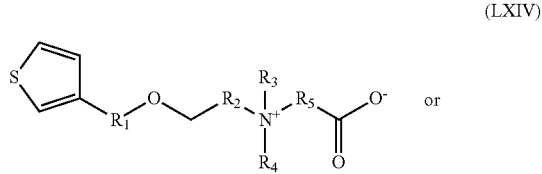

(LXIV)

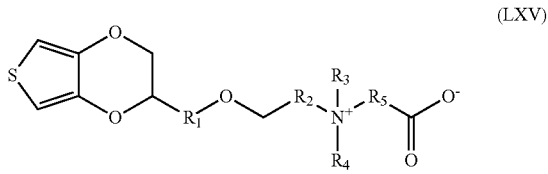

(LXV)

wherein $R_1$ is —C(O)—, —CH$_2$C(O)—, —CH$_2$CH$_2$C(O)—, —(CH$_2$)$_m$C(O)—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$—, —NHC(O)(CH$_2$)$_m$—, —C(O)O—, —OC(O)CH$_2$—, —OC(O)CH$_2$CH$_2$—, —OC(O)(CH$_2$)$_m$—, —OC(O)(CH$_2$)$_m$—, —OC(O)(CH$_2$)$_m$, —O(CH$_2$)$_m$—, —(CH$_2$)$_m$OC(O)(CH$_2$)$_n$—, —(CH$_2$)$_m$C(O)

$-O(CH_2)_n-$, $-CH_2-$, $-CH_2CH_2-$, $-CH_2CH_2CH_2-$, $-CH_2CH_2CH_2CH_2-$, $-CH_2CH_2CH_2CH_2CH_2-$, $-CH_2CH_2CH_2CH_2CH_2CH_2-$, $-(CH_2)_m-$, $-O(CH_2)_m-$, $-O(CH_2)_m-$, $-(CH_2)_m-$, or $-(OCH_2CH_2)_m-$; $R_2$ is $-CH_2-$, $-CH_2CH_2-$, $-CH_2CH_2CH_2-$, $-CH_2CH_2CH_2CH_2-$, $-CH_2CH_2CH_2CH_2CH_2-$, or $-(CH_2)_{x-1}$; $R_3$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; $R_4$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; and $R_5$ is $-CH_2-$, $-CH_2CH_2-$, $-CH_2CH_2CH_2-$, $-CH_2CH_2CH_2CH_2-$, $-CH_2CH_2CH_2CH_2CH_2-$, $-(CH_2)_y-$, or $-(CH_2)_yO(CH_2)_z-$; and m, n, x, y and z are each an integer from 1 to 20.

In some embodiments, the zwitterionic monomer of the present invention may have the formula:

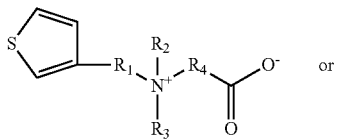

(LXVI)

or

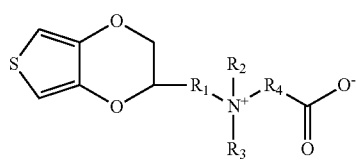

(LXVII)

wherein $R_1$ is $-CH_2-$, $-CH_2CH_2-$, $-CH_2CH_2CH_2-$, $-CH_2CH_2CH_2CH_2-$, $-CH_2CH_2CH_2CH_2CH_2-$, or $-(CH_2)_m-$; $R_2$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; $R_3$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; and $R_4$ is $-CH_2-$, $-CH_2CH_2-$, $-CH_2CH_2CH_2-$, $-CH_2CH_2CH_2CH_2-$, $-CH_2CH_2CH_2CH_2CH_2-$, $-(CH_2)_x-$, or $-(CH_2)_xO(CH_2)_y-$; and m, x and y are each an integer from 1 to 20.

In some embodiments, the zwitterionic monomer of the present invention may have the formula:

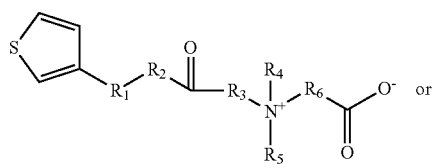

(LXVIII)

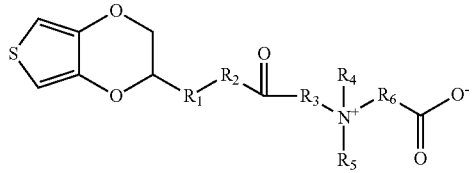

(LXIX)

wherein $R_1$ is $-CH_2-$, $-CH_2CH_2-$, $-CH_2CH_2CH_2-$, $-CH_2CH_2CH_2CH_2-$, $-CH_2CH_2CH_2CH_2CH_2-$ or $-(CH_2)_m-$; $R_2$ is O or NH; $R_3$ is $-CH_2CH_2-$, $-CH_2CH_2CH_2-$, $-CH_2CH_2CH_2CH_2-$, $-CH_2CH_2CH_2CH_2CH_2-$, or $-(CH_2)_m-$; $R_4$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; $R_5$ is $-H$, $-CH_3$, $-CH_2CH_3$, $-CH_2CH_2CH_3$, $-CH_2CH_2CH_2CH_3$, $-CH_2CH_2OH$, $-CH_2CH_2CH_2OH$, $-CH_2CH_2CH_2CH_2OH$, or $-CH_2CH_2CH_2CH_2CH_2OH$; and $R_6$ is $-CH_2-$, $-CH_2CH_2-$, $-CH_2CH_2CH_2-$, $-CH_2CH_2CH_2CH_2-$, $-CH_2CH_2CH_2CH_2CH_2-$ or $-(CH_2)_y-$, or $-(CH_2)_yO(CH_2)_z-$; and m, y and z are each an integer from 1 to 20.

In some embodiments, the zwitterionic monomer of the present invention may have the formula:

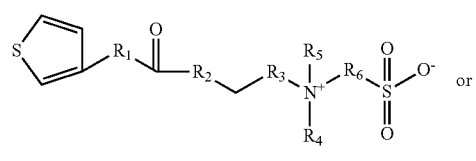

(LXX)

or

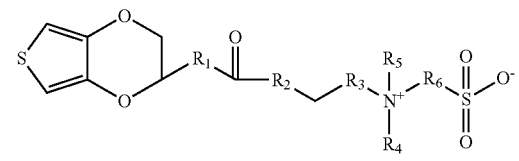

(LXXI)

wherein $R_1$ is $-O-$, $-NH-$, $-CH_2NH-$, $-CH_2CH_2NH-$, $-(CH_2)_mNH-$, $-NHC(O)CH_2-$, $-NHC(O)CH_2CH_2-$, $-NHC(O)(CH_2)_m-$, $-(CH_2)_mNHC(O)(CH_2)_n-$, $-(CH_2)_mNHC(O)O(CH_2)_n-$, $-(CH_2)_mOC(O)NH(CH_2)_n-$, $-(CH_2)_mC(O)NH(CH_2)_n-$, $-NHC(O)(CH_2)_mO-$, $-OC(O)CH_2-$, $-OC(O)CH_2CH_2-$, $-OC(O)(CH_2)_m-$, $-OC(O)(CH_2)_mO-$, $-(CH_2)_mOC(O)(CH_2)_n-$, $-(CH_2)_mC(O)O(CH_2)_n-$, $-CH_2O-$, $-CH_2CH_2O-$, $-CH_2CH_2CH_2O-$, $-CH_2CH_2CH_2CH_2O-$, $-CH_2CH_2CH_2CH_2CH_2O-$, $-CH_2CH_2CH_2CH_2CH_2CH_2O-$, $-(CH_2)_mO-$, $-O(CH_2)_mO-$, $-O(CH_2)_m-$, $-(CH_2)_m-$, $-O(CH_2CH_2O)_m-$, $-(OCH_2CH_2)_m-$ or $-(CH_2CH_2O)_m-$; $R_2$ is $-O-$, $-NH$, $-CH_2C(O)NH-$, $-CH_2CH_2C(O)NH-$, $-(CH_2)_xC(O)NH-$, $-NHC(O)-$, $-NHC(O)CH_2-$, $-NHC(O)CH_2CH_2-$, $-NHC(O)(CH_2)_x-$, $-(CH_2)_xNHC(O)(CH_2)_y-$, $-(CH_2)_xNHC(O)O(CH_2)_y-$, $-(CH_2)_xOC(O)NH(CH_2)_y-$, $-(CH_2)_xC(O)NH(CH_2)_y-$, $-NHC(O)(CH_2)_xC(O)NH-$, $-O(CH_2)_xC(O)NH-$, $-NHC(O)(CH_2)_xO-$, $-NHC(O)(CH_2)_xC(O)O-$, $-CH_2C(O)O-$, $-CH_2CH_2C(O)O-$, $-(CH_2)_mC(O)O-$, $-O(CH_2)_xC(O)O-$, $-(CH_2)_xOC(O)(CH_2)_y-$, $-(CH_2)_xC(O)O(CH_2)_y-$, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_x$O—, —O(CH$_2$)$_x$ O—, —O(CH$_2$)$_x$—, —(CH$_2$)$_x$—, —O(CH$_2$CH$_2$O)$_x$, —(OCH$_2$CH$_2$)$_x$— or —(CH$_2$CH$_2$O)$_x$—; R$_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_{z-1}$—; R$_4$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and R$_6$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_v$—, —(CH$_2$)$_v$O(CH$_2$)$_w$—; and m, n, x, y, z, v and w are each an integer from 1 to 20.

In some embodiments, the zwitterionic monomer of the present invention has the formula:

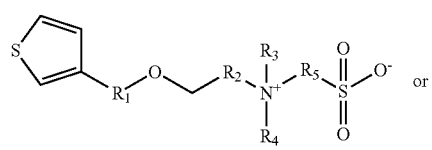

(LXXII)

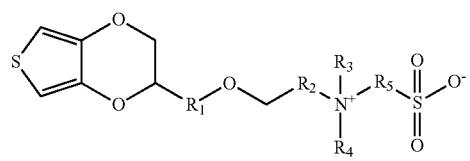

(LXXIII)

wherein R$_1$ is —C(O)—, —CH$_2$C(O)—, —CH$_2$CH$_2$C(O)—, —(CH$_2$)$_m$C(O)—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$—, —NHC(O)(CH$_2$)$_m$—, —C(O)O—, —OC(O)CH$_2$—, —OC(O)CH$_2$CH$_2$—, —OC(O)(CH$_2$)$_m$—, —OC(O)(CH$_2$)$_m$—, —OC(O)(CH$_2$)$_m$, —O(CH$_2$)$_m$—, —(CH$_2$)$_m$OC(O)(CH$_2$)$_n$—, —(CH$_2$)$_m$C(O)O(CH$_2$)$_n$—, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —(CH$_2$)$_m$—, —O(CH$_2$)$_m$—, —O(CH$_2$)$_m$—, —(CH$_2$)$_m$— or —(OCH$_2$CH$_2$)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_{x-1}$—; R$_3$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and R$_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$—, or —(CH$_2$)$_y$O(CH$_2$)$_z$—; and m, n, x, y and z are each an integer from 1 to 20.

In some embodiments, the zwitterionic monomer of the present invention may have the formula:

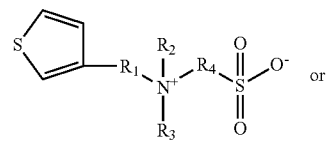

(LXXIV)

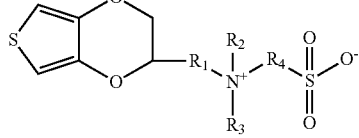

(LXXV)

wherein R$_1$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_m$—; R$_2$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and R$_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$— or —(CH$_2$)$_y$O(CH$_2$)$_x$—; and m, x and y are each an integer from 1 to 20.

In some embodiments, the zwitterionic monomer of the present invention may have the formula:

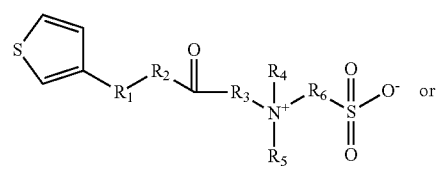

(LXXVI)

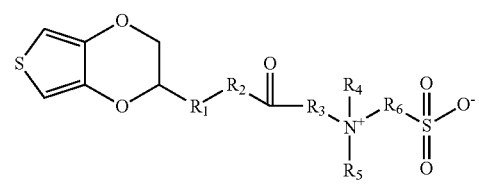

(LXXVII)

wherein R$_1$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_m$—; R$_2$ is O or NH; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_n$—; R$_4$ is —H, —CH$_3$, —CH$_2$CH$_3$, —CH$_2$CH$_2$CH$_3$, CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; and R$_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_x$—, or —(CH$_2$)$_x$O(CH$_2$)$_y$—; and m, n, x and y are each an integer from 1 to 20.

In another aspect, embodiments of the present invention are directed to a conjugated polymer platform comprising a conjugated polymer backbone and mixed positively and negatively charged side chains. These side chains improve the overall conductivity of the conjugated polymer platform and additional design flexibility. The ratio of positively to negatively charged side chains can easily be controlled in order to obtain desired properties. In some embodiments, the ration of positively to negatively charged side chains may be from 0 to 1. In some embodiments, the ration of positively to negatively charged side chains may be from 0.2 to 1. In some embodiments, the ration of positively to negatively charged side chains may be from 0.4 to 1. In some embodiments, the ration of positively to negatively charged side chains may be from 0.6 to 1. In some embodiments, the ration of positively to negatively charged side chains may be from 0.8 to 1.

The conjugated polymer backbone of embodiments of this aspect of the present invention may be the same as for the conjugated polymer backbones described above. In some embodiments, the conjugated polymer backbone may comprise poly(thiophene)s, poly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide)s, poly(acetylene)s, poly(p-phenylene vinylene)s, or any combinations thereof. In some embodiments, the conjugated polymer backbone of may comprise polythiophene or pEDOT.

The negatively charged side chains of embodiments of this aspect of the present invention may include carboxylate, sulfate or phosphate or any combinations thereof. The positively charged side chains of embodiments of this aspect of the present invention may include primary amine, secondary amine, tertiary amine, quaternary ammonium or phosphonium, or any combinations thereof. These positive and negatively charged side chains may be combined with the zwitterionic side chains or any of the other side chains discussed above.

In some embodiments, the conjugated polymer platform may have the formula:

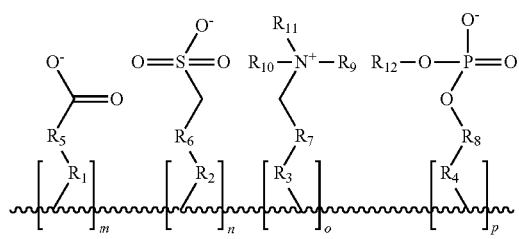

(I)

wherein $R_1$, $R_2$, $R_3$ and $R_4$ are —O—, —NH—, —C(O)NH—, —CH$_2$C(O)NH—, —CH$_2$CH$_2$C(O)NH—, —(CH$_2$)$_x$C(O)NH—, —NHC(O)—, —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$NHC(O)O(CH$_2$)$_y$—, —(CH$_2$)$_x$OC(O)NH(CH$_2$)$_y$—, —(CH$_2$)$_x$C(O)NH(CH$_2$)$_y$—, —NHC(O)(CH$_2$)$_x$C(O)NH—, OC(O)(CH$_2$)$_x$C(O)NH—, —O(CH$_2$)$_x$C(O)NH—, —NHC(O)(CH$_2$)$_x$O—, —NHC(O)(CH$_2$)$_x$C(O)O—, —C(O)O—, —CH$_2$C(O)O—, —CH$_2$CH$_2$C(O)O—, —(CH$_2$)$_x$C(O)O—, —OC(O)—, —OC(O)CH$_2$—, —OC(O)CH$_2$CH$_2$—, —OC(O)(CH$_2$)$_x$—, —OC(O)(CH$_2$)$_x$C(O)O—, —OC(O)(CH$_2$)$_x$O—, —O(CH$_2$)$_x$C(O)O—, —(CH$_2$)$_x$OC(O)(CH$_2$)$_y$—, —(CH$_2$)$_m$C(O)O(CH$_2$)$_x$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_x$O—, —O(CH$_2$)$_x$O—, —O(CH$_2$)$_x$—, —(CH$_2$)$_x$—, —O(CH$_2$H$_2$O)$_x$—, —(OCH$_2$CH$_2$)$_x$— or —(CH$_2$CH$_2$O)$_x$—; $R_5$, $R_6$, $R_7$ and $R_8$ are —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_z$—, —NHC(O)—, —NHC(O)CH$_2$—, —NHC(O)CH$_2$CH$_2$—, NHC(O)(CH$_2$)$_z$—, —OC(O)—, —OC(O)CH$_2$—, —OC(O)CH$_2$CH$_2$— or —OC(O))(CH$_2$)$_z$—; $R_9$, $R_{10}$ and, $R_{11}$ are —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_{12}$ is —H, —CH$_3$, —CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; x, y and z are each an integer from 1 to 20; ∿ is the conjugated polymer backbone; m, n and p are each an integer from 0 to 10,000,000; o is an integer from 0 to 10,000,000 and m, n, p and o are not zero at the same time.

In some embodiments, the conjugated polymer platform may have the formula:

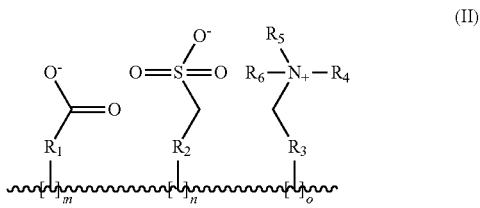

(II)

wherein $R_1$ is —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$ NHC(O)O(CH$_2$)$_y$—, —(CH$_2$)$_x$OC(O)NH (CH$_2$)$_y$—, —(CH$_2$)$_x$C(O)NH(CH$_2$)$_y$—, —OC(O)CH$_2$—, —OC(O)CH$_2$CH$_2$—, —OC(O)(CH$_2$)$_x$—, —(CH$_2$)$_x$OC(O)(CH$_2$)$_y$—, —(CH$_2$)$_x$C(O)O(CH$_2$)$_x$—, —O(CH$_2$)$_x$—, —(CH$_2$)$_x$— or —(OCH$_2$CH$_2$)$_x$—; $R_2$, and $R_3$ are —C(O)NH—, —CH$_2$C(O)NH—, —CH$_2$CH$_2$C(O)NH—, —(CH$_2$)$_z$C(O)NH—, —NHC(O)—, —NHC(O)CH$_2$—, —NHC(O)CH$_2$CH$_2$—, —NHC(O)(CH$_2$)$_y$—, —(CH$_2$)$_z$NHC(O)(CH$_2$)$_y$—, —(CH$_2$)$_z$NHC(O)O(CH$_2$)$_y$—, —(CH$_2$)$_z$OC(O)NH(CH$_2$)$_y$—, —(CH$_2$)$_z$C(O)NH(CH$_2$)$_y$—, —NHC(O)(CH$_2$)$_z$C(O)NH—, OC(O)(CH$_2$)$_z$C(O)NH—, —O(CH$_2$)$_z$C(O)NH—, —NHC(O)(CH$_2$)$_z$O—, —NHC(O)(CH$_2$)$_z$C(O)O—, —C(O)O—, —CH$_2$C(O)O—, —CH$_2$CH$_2$C(O)O—, —(CH$_2$)$_z$C(O)O—, OC(O)—, —OC(O)CH$_2$—, —OC(O)CH$_2$CH$_2$—, —OC(O)(CH$_2$)$_z$—, —OC(O)(CH$_2$)$_z$C(O)O—, —OC(O)(CH$_2$)$_z$O—, —O(CH$_2$)$_z$C(O)O—, —(CH$_2$)$_z$OC(O)(CH$_2$)$_y$—, —(CH$_2$)$_z$C(O)O(CH$_2$)$_y$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_z$O—, —O(CH$_2$)$_z$O—, —O(CH$_2$)$_z$—, —(CH$_2$)$_z$—, —O(CH$_2$CH$_2$O)$_z$, —(OCH$_2$CH$_2$)$_z$— or —(CH$_2$CH$_2$O)$_x$—; $R_4$, $R_5$ and $R_6$ are —H, —CH$_3$, —CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m and n are each an integer from 0 to 10,000,000; o is an integer from 0 to 10,000,000; m, n and o are not zero at the same time and ∿ is the conjugated polymer backbone.

In some embodiments, the conjugated polymer platform may have the formula:

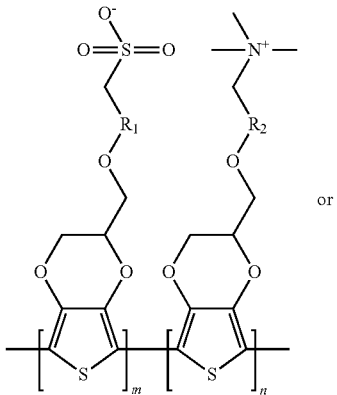
(LXXVIII)

or

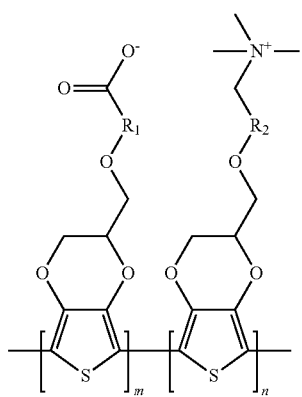
(LXXIX)

wherein R₁ and R₂ are —CH₂CH₂C(O)NH—, —(CH₂)$_z$C(O)NH—, —(CH₂)$_z$NHC(O)(CH₂)$_v$—, —(CH₂)$_z$NHC(O)O(CH₂)$_v$—, —(CH₂)$_z$OC(O)NH(CH₂)$_v$—, —(CH₂)$_z$C(O)NH(CH₂)$_v$—, —C(O)O—, —CH₂C(O)O—, —CH₂CH₂C(O)O—, —(CH₂)$_z$C(O)O—, OC(O)—, —OC(O)CH₂—, —OC(O)CH₂CH₂—, —OC(O)(CH₂)$_z$—, —OC(O)(CH₂)$_z$C(O)O—, —OC(O)(CH₂)$_z$O—, —O(CH₂)$_z$C(O)O—, —(CH₂)$_z$OC(O)(CH₂)$_v$—, —(CH₂)$_z$C(O)O(CH₂)$_v$—, —CH₂O—, —CH₂CH₂O—, —CH₂CH₂CH₂O—, —CH₂CH₂CH₂CH₂O—, —CH₂CH₂CH₂CH₂CH₂O—, —CH₂CH₂CH₂CH₂CH₂CH₂O—, —(CH₂)$_z$O—, —O(CH₂)$_z$O—, —O(CH₂)$_z$—, —(CH₂)$_z$—, —O(CH₂CH₂O)$_z$—, —(OCH₂CH₂)$_z$— or —(CH₂CH₂O)$_x$—, —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂—, —(CH₂)$_z$—, —C(O)(CH₂)$_z$, —CH₂CH₂CH₂CH₂CH₂CH₂CH₂CH₂CH₂CH₂—; z and v are each an integer from 1 to 20; m is an integer from 0 to 10,000,000 and n is an integer 0 to 10,000,000, m and n are not zero at the same time.

In some embodiments, the conjugated polymer platform may have the formula:

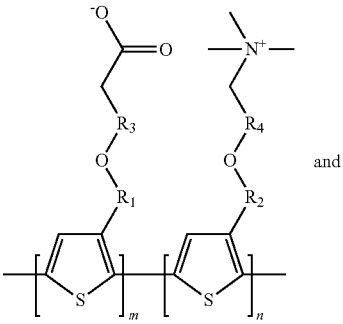
(LXXX)

and

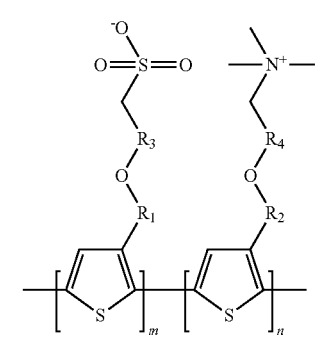
(LXXXI)

wherein R₁ is —(CH₂)$_x$NHC(O)(CH₂)$_y$—, —(CH₂)$_x$NHC(O)O(CH₂)$_y$—, —(CH₂)$_x$OC(O)NH(CH₂)$_y$—, —(CH₂)$_x$C(O)NH(CH₂)$_y$—, —C(O)—, —CH₂C(O)—, —CH₂CH₂C(O)—, —(CH₂)$_x$C(O)O—, —OC(O)—, —OC(O)CH₂—, —OC(O)CH₂CH₂—, —OC(O)(CH₂)$_x$—, —OC(O)(CH₂)$_x$, —OC(O)(CH₂)$_x$—, —O(CH₂)$_x$C(O)—, —(CH₂)$_x$OC(O)(CH₂)$_y$—, —(CH₂)$_x$C(O)O(CH₂)$_y$—, —CH₂—, —CH₂CH₂—, —CH₂CH₂CH₂—, —CH₂CH₂CH₂CH₂—, —CH₂CH₂CH₂CH₂CH₂—, —CH₂CH₂CH₂CH₂CH₂CH₂—, —(CH₂)$_x$—, —O(CH₂)$_x$—, —O(CH₂)$_x$—, —(CH₂)$_x$—, —(OCH₂CH₂)$_x$— or —(CH₂CH₂O)$_x$—, —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂—, —CH₂CH₂CH₂CH₂CH₂CH₂CH₂CH₂CH₂CH₂—, —(CH₂)$_x$—, —(CH₂)$_x$C(O)—; R₂ is —(CH₂)$_z$NHC(O)(CH₂)$_v$—, —(CH₂)$_z$NHC(O)O(CH₂)$_v$—, —(CH₂)$_z$OC(O)NH(CH₂)$_v$—, —(CH₂)$_z$C(O)NH(CH₂)$_v$—, —C(O)—, —CH₂C(O)—, —CH₂CH₂C(O)—, —(CH₂)$_z$C(O)O—, —OC(O)—, —OC(O)CH₂—, —OC(O)CH₂CH₂—, —OC(O)(CH₂)$_z$—, —OC(O)(CH₂)$_z$C(O)—, —OC(O)(CH₂)$_z$—, —O(CH₂)$_z$C(O)—, —(CH₂)$_z$OC(O)(CH₂)$_v$—, —(CH₂)$_z$C(O)O(CH₂)$_v$—, —CH₂—, —CH₂CH₂—, —CH₂CH₂CH₂—, —CH₂CH₂CH₂CH₂—, —CH₂CH₂CH₂CH₂CH₂—, —CH₂CH₂CH₂CH₂CH₂—, —(CH₂)$_z$—, —O(CH₂)$_z$—, —O(CH₂)$_z$—, —(CH₂)$_z$—, —(OCH₂CH₂)$_z$— or —(CH₂CH₂O)$_z$—, —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂—, —CH₂CH₂CH₂CH₂CH₂CH₂CH₂CH₂CH₂CH₂—, —(CH₂)$_z$—, —(CH₂)$_z$C(O)—; R₃ is —(CH₂)$_u$NHC(O)(CH₂)$_w$—, —(CH₂)$_u$NHC(O)O(CH₂)$_w$—, —(CH₂)$_u$OC(O)NH(CH₂)$_w$—, —(CH₂)$_u$C(O)NH(CH₂)$_w$—, —OC(O)CH₂—, —OC(O)CH₂CH₂—, —OC(O)(CH$_2$)$_u$—, —(CH$_2$)$_z$OC(O)(CH$_2$)$_u$—, —(CH$_2$)$_u$C(O)O(CH$_2$)$_w$—, —(CH$_2$)$_u$—, —(CH$_2$CH$_2$O)$_u$(CH$_2$)$_w$—, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—; —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$— or —CH$_2$CH$_2$CH$_2$CH$_2$CH$_2$CH$_2$CH$_2$CH$_2$CH$_2$CH$_2$—; R$_4$ is —(CH$_2$)$_a$NHC(O)(CH$_2$)$_b$—, (CH$_2$)$_a$NHC(O)O(CH$_2$)$_b$—, —(CH$_2$)$_a$OC(O)NH(CH$_2$)$_b$—, —(CH$_2$)$_a$C(O)NH(CH$_2$)$_b$—, OC(O)CH$_2$—, —OC(O)CH$_2$CH$_2$—, —OC(O)(CH$_2$)$_a$—, —(CH$_2$)$_a$OC(O)(CH$_2$)$_b$—, —(CH$_2$)$_a$C(O)O(CH$_2$)$_b$—, —(CH$_2$)$_a$—, —(CH$_2$CH$_2$O)$_a$(CH$_2$)$_b$—, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—; —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$— or —CH$_2$CH$_2$CH$_2$CH$_2$CH$_2$CH$_2$CH$_2$CH$_2$CH$_2$CH$_2$—; a, b, x, y, z, v, u and w are each an integer from 1 to 20; m is an integer from 1 to 10,000,000; n is an integer from 1 to 10,000,000; and m and n are not zero at the same time.

In yet another aspect, embodiments of the present invention are directed to various methods of making the conjugated polymer platform described above. In some embodiments, the conjugated polymer platforms described above may be made from any of the zwitterionic monomers discussed above. In some embodiments, the conjugated polymer platform may be made from a zwitterionic monomer having a polymerizable thiophene or 3,4-ethylenedioxythiophene (EDOT) group and a zwitterionic betaine group. In some embodiments, the zwitterionic monomer may be made as set forth below.

In some embodiments, once the zwitterionic monomer is selected, it is dissolved in a suitable solvent and polymerized to produce the conjugated polymer platform. The specific mechanism for polymerization may depend upon the particular polymerizable components of the zwitterionic monomer being chosen. In some embodiments, the polymerizable components of the zwitterionic monomer are a thiophene or EDOT and the monomers are polymerized using a suitable radical initiator such as FeCl$_3$, ammonium persulfate, or hydrogen peroxide.

While the fully formed zwitterionic monomer may be used to form the polymer as set forth above, the method is not so limited. In some embodiments, the polymer is formed first and the betaine groups are added to the polymer later. One such embodiment is shown in Scheme 1 below.

Scheme 1

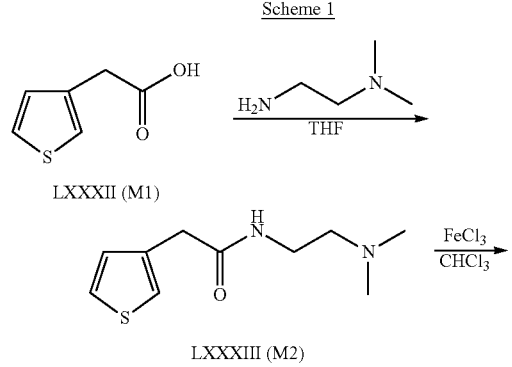

LXXXII (M1)

LXXXIII (M2)

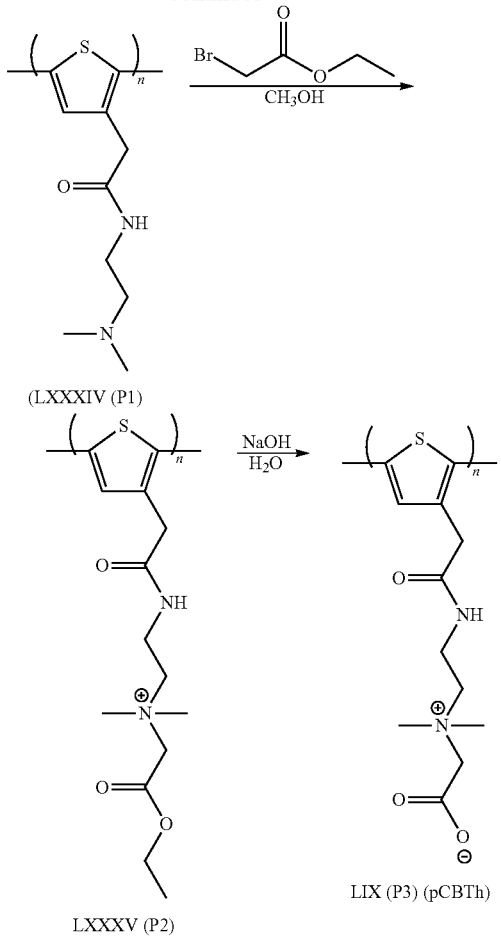

(LXXXIV (P1))

LXXXV (P2)

LIX (P3) (pCBTh)

In these embodiments, a polymerizable monomer with an reactive group for side chain conjugation may be used as the starting material. Suitable starting materials may include, without limitation, 2-(thiophen-3-yl)acetic acid, thiophen-3-ylmethanol, thiophen-3-ylmethanamine, 2-(2,3-dihydrothieno[3,4-b][1,4]dioxin-2-yl)acetic acid, or (2,3-dihydrothieno[3,4-b][1,4]dioxin-2-yl)methanol. In some embodiments, the starting materials may be 2-(thiophen-3-yl)acetic acid (LXXXII) (M1). The starting material is dissolved in a suitable solvent and reacted with a molecule with one hydroxyl group or primary amine group at one end and tertiary amine on the other end to form a polymerizable conjugated monomer having a tertiary amine end group (LXXXIII)(M2). In some embodiments, the starting material may be dissolved in THF and reacted with N,N'-dimethylethylenediamine to form N-(2-(dimethylamino)ethyl)-2-(thiophen-3-yl) acetamide (LXXXIII)(M2). The 2-(thiophen-3-yl)acetic acid is then polymerized by reacting it with a suitable radical initiator such as FeCl$_3$, ammonium persulfate, or hydrogen peroxide, to form a polymer having side chains comprising having a functional group. In some embodiments, monomers are polymerized by the addition of FeCl$_3$ in anhydrous chloroform and the side chains have terminal tertiary amine groups (LXXXIV)(P1).

The polymer may then be reacted with an ethyl bromoacetate to add a carboxylate group to one or more of the side chains. In some embodiments, poly(2-ethoxy-N,N-dimethyl-2-oxo-N-(2-(2-(thiophen-3-yl)acetamido)ethyl) ethan-1-aminium bromide) (LXXXV) (P2) may be used. The polymer is then reacted with a base to convert the carboxylate ester group to a carboxylate group forming compound LIX (P3).

As set forth above, the conjugated polymer platform may also have one or more crosslinking groups. These groups may be added by including a crosslinking monomer having a compatible polymerizable component and a crosslinking group when forming the polymer or by adding crosslinking groups to the side chain or backbone of the polymer. Any of the crosslinking groups discussed above may be used. Crosslinking groups may include, without limitation, acrylate, methacrylate, ethylacrylate, acrylamide, methacrylamide, alkene, alkyne, epoxide, azide, aldehyde or ethylacrylamide group.

As set forth above, the conjugated polymer platform may also have one or more securing groups. These groups may be added by including a monomers having a securing group and a compatible polymerizable component (a securing monomer) when forming the polymer or by adding securing groups to the side chain or backbone of the polymer. Any of the securing groups discussed above may be used. The attachment moiety may include, without limitation, cystamine, cysteine, 1-ethanol-2-thiol, (3-aminopropyl)triethoxysilane, (3-aminopropyl)trimethoxysilane, 3,4-dihydroxyphenethylamine, 12-hydroxy dodecyl phosphate, 2-aminoethylphosphonic acid, 3-aminopropylphosphonic acid, 4-aminobutylphosphonic acid, 2-hydrxylethylphosphonic acid, 3-hydrxylpropylphosphonic acid, 4-hydrxylbutylphosphonic acid, and combinations thereof.

In some embodiments, the method may comprise: dissolving 3-thiopheneacetic acid in a suitable solvent; adding 1,1'-carbonyldiimidazole (CDI) to the solution and reducing the temperature; adding N,N'-dimethylethylenediamine diluted with anhydrous THF to the product to form N-(2-(dimethylamino)ethyl)-2-(thiophen-3-yl)acetamide; suspending FeCl$_3$ in anhydrous chloroform under a positive nitrogen atmosphere and reducing the temperature; dissolving the N-(2-(dimethylamino)ethyl)-2-(thiophen-3-yl)acetamide in anhydrous chloroform and adding it to the product to produce a polymer having the formula:

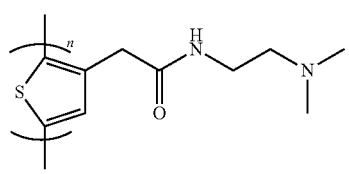

(LXXXIV)

wherein n is an integer from 1 to 1,000,000; dissolving polymer LXXXIV in a suitable solvent and reacting it with ethyl bromoacetate to form a polymer having the formula:

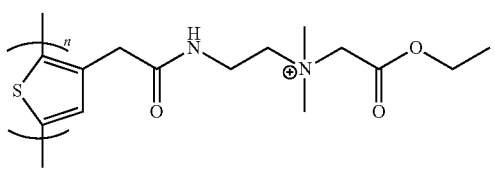

(LXXXV)

wherein n is an integer from 1 to 1,000,000; and dissolving the resulting polymer (LXXXV) in deionized water and passing it through an ion exchange resin filled column to hydrolyze the ethyl ester into a zwitterionic form to produce a polymer having the formula:

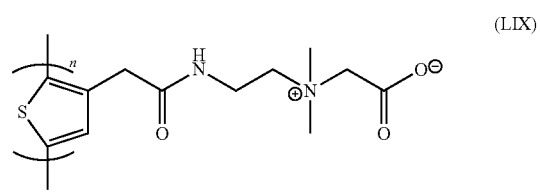

(LIX)

wherein n is an integer from 1 to 1,000,000.

In some embodiments, the method may comprise: dissolving 3-thiopheneacetic acid in a suitable solvent and reacting it with H$_2$SO$_4$ to produce methyl thiophene-3-acetate; combining the polymer and the methyl thiophene-3-acetate in a predetermined ratio; polymerizing the mixture using FeCl$_3$ to form a polymer having the formula:

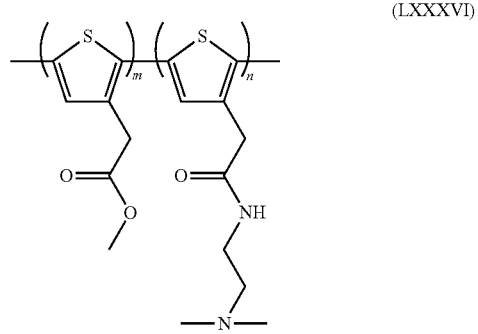

(LXXXVI)

wherein m is an integer from 1 to 1,000,000 and n is an integer from 1 to 1,000,000; dissolving the resulting polymer in a suitable solvent and reacting it with ethyl bromoacetate to form a polymer having the formula:

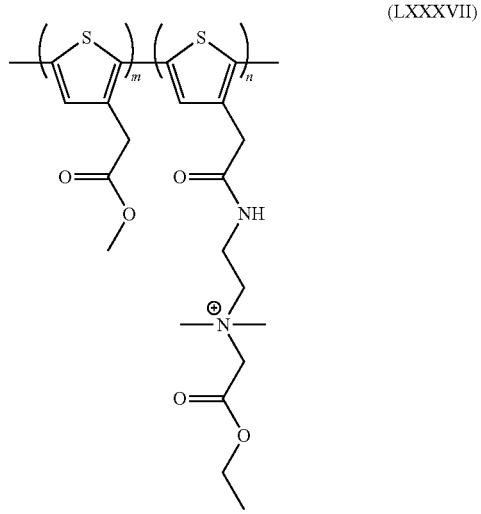

(LXXXVII)

wherein m is an integer from 1 to 1,000,000 and n is an integer from 1 to 1,000,000; dissolving that polymer in deionized water and passing it through an ion exchange resin filled column to produce a polymer having the formula:

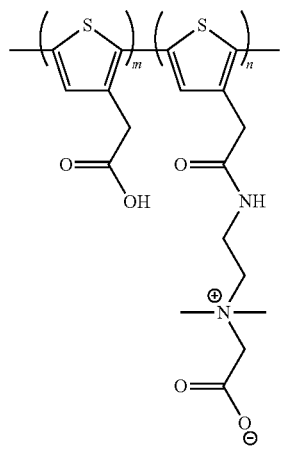
(LXXXVIII)

wherein m is an integer from 1 to 1,000,000 and n is an integer from 1 to 1,000,000; and reacting that polymer with 2-aminoethyl methacrylamide hydrochloride in the presence of N-hydroxysuccinimide (EDC) to provide a polymer having the formula:

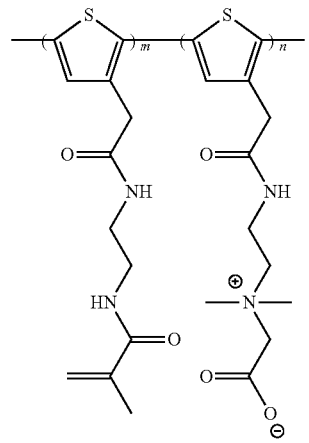
(LXI)

wherein m is an integer from 1 to 1,000,000 and n is an integer from 1 to 1,000,000.

In some embodiments, the method may comprise: reacting the above polymer with cystamine dihydrochloride to produce a polymer having the formula:

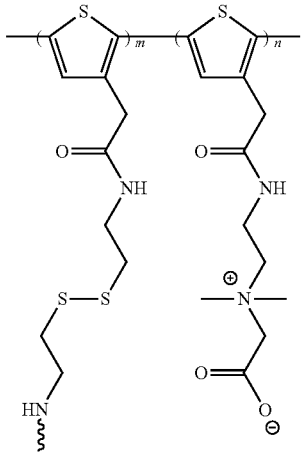
(LXXXIX)

wherein m is an integer from 1 to 1,000,000 and n is an integer from 1 to 1,000,000; and reacting the that polymer with tris(2-carboxyethyl)phosphine hydrochloride (TCEP) to obtain a polymer having the formula:

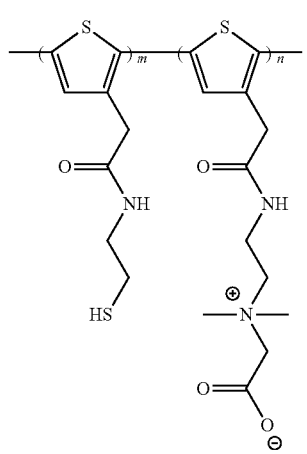
(LX)

wherein m is an integer from 1 to 1,000,000 and n is an integer from 1 to 1,000,000.

In some embodiments, the method may comprise: dissolving 3,4-ethylenedioxythiophene derivatives in a suitable solvent; adding a bifunctional linker to the solution at the presence of suitable catalyst(s); adding carboxybetaine, its derivatives or the combination thereof to the resulting product in a suitable solvent to form carboxybetaine 3,4-ethylenedioxythiophene or its derivatives; and polymerizing the product to produce a polymer having a formula selected from:

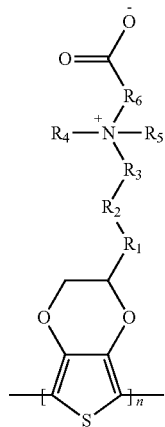

(XC)

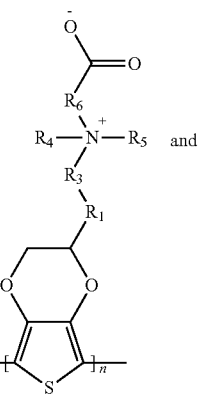

(XCI)

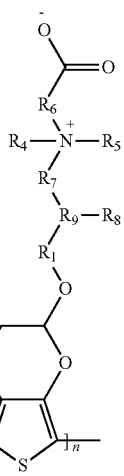

(XCII)

wherein R₁ is —CH₂—, —CH₂CH₂—, —CH₂CH₂CH₂—, —CH₂CH₂CH₂CH₂—, —CH₂CH₂CH₂CH₂CH₂—, —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂— or —CH₂CH₂CH₂CH₂CH₂CH₂CH₂CH₂CH₂CH₂—; R₂ is O, —OC(=O)—, —NHC(=O)—, —C(=O)O—, —C(=O)NH—, —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂— or —CH₂CH₂CH₂CH₂CH₂CH₂CH₂CH₂CH₂CH₂—; and R₃ are —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂— or —CH₂CH₂CH₂CH₂CH₂CH₂CH₂CH₂CH₂CH₂—; R₄, and R₅ are —H, —CH₃, —CH₂CH₃, —CH₂CH₂CH₃, —CH₂CH₂CH₂CH₃, CH₂CH₂OH, —CH₂CH₂CH₂OH, —CH₂CH₂CH₂CH₂OH, or —CH₂CH₂CH₂CH₂CH₂OH; R₆ is —CH₂—, —CH₂CH₂—, —CH₂CH₂CH₂—, —CH₂CH₂CH₂CH₂—, —CH₂CH₂CH₂CH₂CH₂—, —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂— or —CH₂CH₂CH₂CH₂CH₂CH₂CH₂CH₂CH₂CH₂—; R₇, is —CH₂—, —CH₂CH₂—, —CH₂CH₂CH₂—, —CH₂CH₂CH₂CH₂—, —CH₂CH₂CH₂CH₂CH₂—; —CH₂CH₂CH₂CH₂CH₂CH₂—, —CH₂CH₂CH₂CH₂CH₂CH₂CH₂—, —CH₂CH₂CH₂CH₂CH₂CH₂CH₂CH₂—, —CH₂CH₂CH₂CH₂CH₂CH₂CH₂CH₂CH₂— or —CH₂CH₂CH₂CH₂CH₂CH₂CH₂CH₂CH₂CH₂—; R₈, is —H or —OH; R₉, is —CH₂— or —CH—; and n are an each integer from 1 to 10,000,000.

In some embodiments, the method for making the conjugated polymer platform described above may comprise: dissolving equal mole of (2,3-dihydrothieno[3,4-b][1,4]dioxin-2-yl)methanol and sodium hydride in a suitable solvent; adding excessive amount of 1-bromo-3-chloropropane to the solution; adding dimethylglycinate ester to the resulting product in a suitable solvent to form 2-((3-((2,3-dihydrothieno[3,4-b][1,4]dioxin-2-yl)oxy)propyl)dimethylammonio)acetate ester; dissolving that polymer in a suitable solvent containing the suitable chemical reagent(s) to remove ester to produce 2-((3-((2,3-dihydrothieno[3,4-b][1,4]dioxin-2-yl)oxy)propyl)dimethylammonio)acetate; and polymerizing the resulting product under a suitable condition to produce a polymer having the formula:

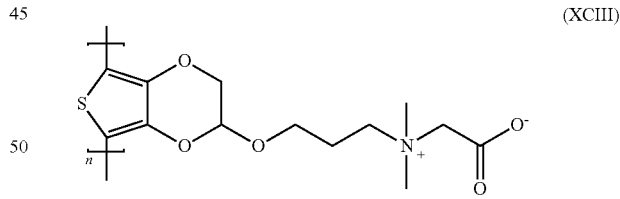

(XCIII)

wherein n is an integer from 1 to 10,000,000. In some embodiments, the above referenced method may also comprise: polymerizing the above monomer under a suitable condition to produce poly(2-((3-((2,3-dihydrothieno[3,4-b][1,4]dioxin-2-yl)oxy)propyl)dimethylammonio)acetate ester) dissolving the polymer in a suitable solvent containing the suitable chemical reagent(s) to remove ester to produce poly(2-((3-((2,3-dihydrothieno[3,4-b][1,4]dioxin-2-yl)oxy)propyl)dimethylammonio)acetate).

In some embodiments, the method for making the conjugated polymer platform described above may comprise: dissolving equal mole of (2,3-dihydrothieno[3,4-b][1,4]dioxin-2-yl)methanol and sodium hydride in a suitable solvent; adding 1-bromo-3-chloropropane to the solution of;

adding dimethylglycinate to the product in a suitable solvent to form 2-((3-((2,3-dihydrothieno[3,4-b][1,4]dioxin-2-yl)oxy)propyl)dimethylammonio)acetate; polymerizing the resulting product under suitable conditions to produce poly (2-((3-((2,3-dihydrothieno[3,4-b][1,4]dioxin-2-yl)oxy)propyl)dimethylammonio)acetate). In some embodiments, the method may comprise: dissolving equal mole of (2,3-dihydrothieno[3,4-b][1,4]dioxin-2-yl)methanol and sodium hydride in a suitable solvent; adding 1-bromo-3-chloropropane to the solution; polymerizing the product under suitable conditions; and adding dimethylglycinate in a suitable solvent to produce poly(2-((3-((2,3-dihydrothieno[3,4-b][1,4]dioxin-2-yl)oxy)propyl)dimethylammonio)acetate).

In some embodiments, the method for making the conjugated polymer platform described above may comprise: dissolving (2,3-dihydrothieno[3,4-b][1,4]dioxin-2-yl) methanol in a suitable solvent; adding equal mole of bromoacetyl bromide to the solution at the presence of organic or inorganic base(s); adding dimethylglycinate to the product in a suitable solvent to form 2-((3-((2,3-dihydrothieno[3,4-b][1,4]dioxin-2-yl)oxy)-3-oxopropyl)dimethylammonio)acetate; polymerizing the resulting product under a suitable condition to produce a polymer having the formula:

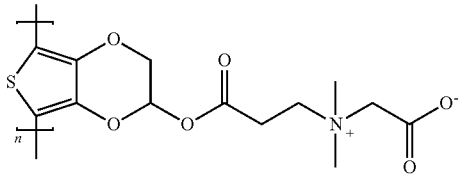

(XCIV)

wherein n is an integer from 1 to 10,000,000.

In some embodiments, the method for making the conjugated polymer platform described above may comprise: dissolving (2,3-dihydrothieno[3,4-b][1,4]dioxin-2-yl) methanol in a suitable solvent; adding equal mole of bromoacetyl bromide to the solution in the presence of organic or inorganic base(s); polymerizing the resulting product under suitable conditions to produce a polymer having the formula:

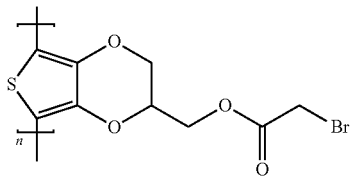

(XCV)

wherein n is an integer from 1 to 10,000,000; and adding dimethylglycinate to the resulting product in a suitable solvent to form poly(2-((3-((2,3-dihydrothieno[3,4-b][1,4]dioxin-2-yl)oxy)-3-oxopropyl)dimethylammonio)acetate). In some embodiments, the method may comprise: dissolving 2-(chloromethyl)-2,3-dihydrothieno[3,4-b][1,4]dioxine in a suitable solvent; adding dimethylglycinate to the solution in a suitable solvent to form 2-(((2,3-dihydrothieno[3,4-b][1,4]dioxin-2-yl)methyl)dimethylammonio)acetate; polymerizing the resulting product under a suitable condition to produce a polymer having the formula:

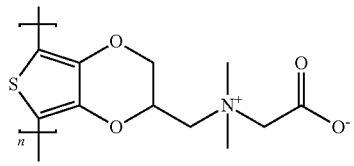

(XCVI)

wherein n is an integer from 1 to 10,000,000.

In some embodiments, the method for making the conjugated polymer platform described above may comprise: dissolving 2-(chloromethyl)-2,3-dihydrothieno[3,4-b][1,4]dioxine in a suitable solvent; adding dimethylglycinate ester to the solution in a suitable solvent to form 2-(((2,3-dihydrothieno[3,4-b][1,4]dioxin-2-yl)methyl)dimethylammonio)acetate ester; polymerizing the resulting under a suitable condition to produce a polymer having the formula:

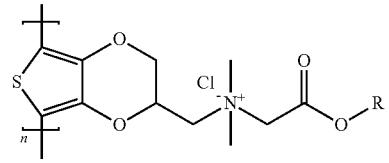

(XCVII)

wherein n is an integer from 1 to 10,000,000; and dissolving the polymer in a suitable solvent containing the suitable chemical reagent(s) to remove ester to produce poly(2-(((2,3-dihydrothieno[3,4-b][1,4]dioxin-2-yl)methyl)dimethylammonio)acetate).

In some embodiments, the method for making the conjugated polymer platform described above may comprise: polymerizing 2-(chloromethyl)-2,3-dihydrothieno[3,4-b][1,4]dioxine under a suitable condition to produce a poly(2-(chloromethyl)-2,3-dihydrothieno[3,4-b][1,4]dioxine); adding dimethylglycinate ester to the solution in a suitable solvent to form poly(2-(((2,3-dihydrothieno[3,4-b][1,4]dioxin-2-yl)methyl)dimethylammonio)acetate ester); dissolving the resulting polymer of in a suitable solvent containing the suitable chemical reagent(s) to remove the ester and produce poly(2-(((2,3-dihydrothieno[3,4-b][1,4]dioxin-2-yl)methyl)dimethylammonio)acetate). In some embodiments, the method may comprise: polymerizing 2-(chloromethyl)-2,3-dihydrothieno[3,4-b][1,4]dioxine under a suitable condition to produce a poly(2-(chloromethyl)-2,3-dihydrothieno[3,4-b][1,4]dioxine); and adding dimethylglycinate to the solution in a suitable solvent to form poly(2-(((2,3-dihydrothieno[3,4-b][1,4]dioxin-2-yl)methyl)dimethylammonio)acetate). In some embodiments, the method may comprise: polymerizing 2-(chloromethyl)-2,3-dihydrothieno[3,4-b][1,4]dioxine under a suitable condition to produce a poly(2-(chloromethyl)-2,3-dihydrothieno[3,4-b][1,4]dioxine) and adding dimethylglycinate in a suitable solvent to the solution to form poly(2-(((2,3-dihydrothieno[3,4-b][1,4]dioxin-2-yl)methyl)dimethylammonio)acetate).

In yet another aspect, embodiments of the present invention are directed to a method of crosslinking the zwitterionic polymer platform discussed above to form polymer networks, particularly hydrogels. As set forth above, CP hydrogels are of great interest for biomedical and biotech applications, since they provide not only a favorable electrical conducting environments but also a highest level of hydration and similarity to tissues. In some embodiments, pendant methacrylamide (MAA) groups on pCBTh-co-ThMAA polymers described above function as crosslinkers to form the hydrogel. In some embodiments, a pCBTh-co-ThMAA conducting hydrogel according to the present invention may be synthesized using a thermal free radical initiator, VA-044. In some other embodiments, the pCBTh-co-ThMAA hydrogel may be synthesized using photoinitiators or multi-thiol crosslinkers via the Michael type reaction in aqueous solution. Both methods have been widely used to encapsulate cells, enzymes or other labile biomacromolecules into hydrogel networks. The gelation process of macromonomers can be more accurately controlled at a clinically acceptable rate and timescale.

Any of the crosslinking groups discussed above may be used. Crosslinking groups may include, without limitation, acrylate, methacrylate, ethylacrylate, acrylamide or methacrylamide. Conjugated polymers with crosslinking groups can be dissolved in a suitable solution and form the hydrogel initiated by a suitable free radical initiator such as thermal, photo or redox free radical initiator. Conjugated polymers with crosslinking groups can be dissolved in a suitable solution and form the hydrogel initiated by a suitable free radical initiator such as thermal, photo or redox free radical initiator. The conjugated polymer can also crosslinked by multi-arm thiols at the presence of suitable catalysts.

In some embodiments, these crosslinking groups may be added by including a crosslinking monomer having a compatible polymerizable component and a crosslinking group when forming the polymer or by adding crosslinking groups to the side chain or backbone of the polymer. Any of the crosslinking groups discussed above may be used. Crosslinking groups may include, without limitation, acrylate, methacrylate, ethylacrylate, acrylamide or methacrylamide, thiol, alkene, alkyne, epoxide, azide, aldehyde or ethylacrylamide group. Conjugated polymers with crosslinking groups can be dissolved in a suitable solution and crosslinked by suitable crosslinkers, such as molecules having more than one acrylate, methacrylate, ethylacrylate, acrylamide or methacrylamide hydroxyl, azide, thiol, amine, thiol, alkene, alkyne, epoxide, azide, aldehyde, ethylacrylamide groups or the combination of thereof at the presence of suitable catalysts or initiators to form the hydrogel.

In yet another aspect, embodiments of the present invention are directed to a method of making the zwitterionic monomers discussed above. In one or more embodiments, the zwitterionic monomers according to the present invention may be synthesized by first dissolving polymerizable component of a conjugated polymer in a suitable solvent. One of ordinary skill in the art will be able to select a suitable solvent without undue experimentation. Suitable solvents may include, without limitation, tetrahydrofuran, acetonitrile, or chloroform. The polymerizable component may include, without limitation, thiophene, EDOT, pyrole, aniline, fluorene, phenylene, pyrene, azulene, naphthalene, pyrrole, carbazole, indole, azepine, aniline, 3,4-ethylenedioxythiophene, p-phenylene sulfide, acetylene, p-phenylene vinylene. It should be appreciated that in addition to function sites necessary to form a polymer, these components will also have at least one other functional group or other binding site available. Next, a bifunctional linker is added to the solution at the presence of suitable catalyst(s. The bifunctional linker links the polymerizable component of the monomer to the betaine group and, accordingly, will have a first linking group configured to bond with a functional group or other binding site on the polymerizable component and a second linking group configured to bond to the a suitable site on the betaine group. The specific linking groups on the bifunctional linker will, of course, depend upon the specific polymerizable component and betaine group being used. Further, it should be apparent that, in addition to linking the polymerizable component and betaine group, the bifunctional linker may constitute a significant portion of the zwitterionic side chains one the polymer is formed and in some embodiments may be used to introduce desired structures into the zwitterionic side chains. In some embodiments, the bifunctional linker may be any molecule with more than one terminal groups substituted by halogen, thiol, epoxide, amine, alkene, alkyne, carboxylate, carboxylate esters, azide, or the combination of thereof.

At this stage, at catalyst may be used to bind the bifunctional linker to the polymerizable component. One of ordinary skill will be able to select a suitable catalyst without undue experimentation. Suitable catalysts may include, without limitation, an organic or inorganic base or an organic or inorganic acid.

Last, a desired betaine group and/or derivative thereof is dissolved in a suitable solvent and added to the solution containing the bifunctional linker/polymerizable component, where it bonds to the available linking group on the bifunctional linker to produce the zwitterionic monomer described above. The desired betaine group and/or derivative thereof may be any of those discussed above.

In one or more embodiments, the method of making the zwitterionic monomer may comprise: dissolving 3-thiopheneacetic acid in a suitable solvent; adding 1,1'-carbonyldiimidazole (CDI) to the solution and reducing the temperature; adding N,N'-dimethylethylenediamine diluted with anhydrous THF to form N-(2-(dimethylamino)ethyl)-2-(thiophen-3-yl)acetamide; dissolving the N-(2-(dimethylamino)ethyl)-2-(thiophen-3-yl)acetamide in a suitable solvent and reacting it with ethyl bromoacetate to form 2-ethoxy-N,N-dimethyl-2-oxo-N-(2-(2-(thiophen-3-yl)acetamido)ethyl)ethan-1-aminium bromide; dissolving the resulting polymer in deionized water and passing it through an ion exchange resin filled column to hydrolyze the ethyl ester into a zwitterionic form to produce 2-(dimethyl(2-(2-(thiophen-3-yl)acetamido)ethyl)ammonio)acetate having the formula:

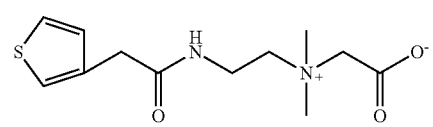

(XCVIII)

In one or more embodiments, the method of making the zwitterionic monomer may comprise: dissolving (2,3-dihydrothieno[3,4-b][1,4]dioxin-2-yl)methanol and sodium hydride in a suitable solvent; adding 1-bromo-3-chloropropane to the solution; adding dimethylglycinate ester in a suitable solvent to form 2-((3-((2,3-dihydrothieno[3,4-b][1,4]dioxin-2-yl)oxy)propyl)dimethylammonio)acetate ester; and dissolving the resulting product in a suitable solvent containing the suitable chemical reagent(s) to remove ester to produce 2-((3-((2,3-dihydrothieno[3,4-b][1,4]dioxin-2-yl)oxy)propyl)dimethylammonio)acetate (carboxybetaine EDOT) having the formula:

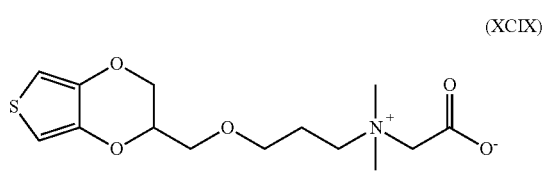

(XCIX)

FIG. 23 is a $^1$H NMR of molecule XCIX.

In another aspect, the present invention provides a method of making the redox sensitive hydrogel described above. The redox sensitive hydrogel may be prepared much in the same way as the hydrogels described above and may have the same conjugated polymer backbone and any of the various zwitterionic side chains, crosslinking side chains, securing side chains and/or positively/negatively charged side chains discussed above. In the redox sensitive hydrogels, however, at least some of the side chains will redox sensitive side chains containing a thiol or other redox sensitive functional group. It is not of any particular importance, however, which type of side chain contains the thiol or other redox sensitive functional group. It should be noted that the thiol groups on the securing side chains discussed above with respect to the polymer, may act as a crosslinking group when forming a redox sensitive hydrogel according to embodiments of the present invention. Once the conjugated polymer having redox sensitive side chains containing thiol or other redox sensitive functional groups has been synthesized and dissolved in a suitable solvent, an oxidizer is added to form disulfide bonds between the side chains or between the side chains and the conjugated polymer backbone, forming a redox sensitive hydrogel. Suitable oxidizers may include, without limitation ammonium peroxide, hydrogen peroxide, $FeCl_3$, Suitable oxidizers may include, without limitation $FeCl_3$, iodine, hypochlorite, and permangonite.

Figure 6:
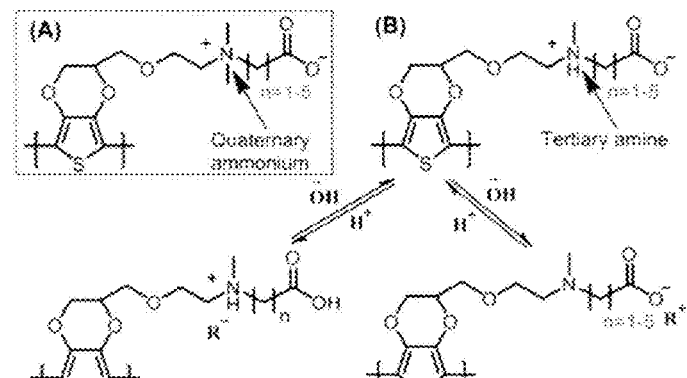
FIG. 6 is a schematic showing pCBEDOT with quaternary ammonium (A) and tertiary amine as the cation.

In carboxybetaine (CB) molecules, the length of the spacer between amine and carboxylate affects the charge distribution of side chains. The increase of the spacer length reduces the acidity of carboxylate, which can be protonated at a higher pH. pKa of carboxylate increases from ~2 to 4 if a 1-methylene spacer is changed to a 3-methylene spacer. With the protonation of carboxylate, the neutral side chain switches to the positively charged state. The net charge of side chains affects the band gap, redox potential and antifouling properties of the conjugated polymer backbone. poly(carboxybetaine EDOT) (PCBEDOT) (See FIG. 6) with 1 to 5-methylene spacers will have different antifouling and conducting properties. Zwitterionic side chain can switch to different charge states in response to pH changes and affect the overall planarization, solubility and assembly behavior of conjugated backbone, which determine their optical properties.

In another aspect, the present invention provides a biomaterial platform comprising the conjugated polymer platform and/or redox sensitive hydrogels described above. In some embodiments, the conjugated polymer platform and/or redox sensitive hydrogels of the present invention may be used as a semiconductor to fabricate bioelectronic devices or as an electron or ion collector in bioelectronic devices.

In some embodiments, the conjugated polymer platforms and/or redox sensitive hydrogels of the present invention may be used in wide variety of implantable medical devices. In some embodiments, the conjugated polymer platforms and/or redox sensitive hydrogels of the present invention may be used to fabricate electrodes that deliver or detect electrical signal in medical devices. In some embodiments, the conjugated polymer platforms and/or redox sensitive hydrogels of the present invention may be to fabricate optical sensors in medical devices. In some embodiments, the conjugated polymer platforms and/or redox sensitive hydrogels of the present invention may be used as an antifouling and/or antimicrobial coating for implanted medical devices to prevent biofouling and infection. In some embodiments, the conjugated polymer platforms and/or redox sensitive hydrogels of the present invention may also be used to fabricate transistor, transducer or supercapacitor in such medical devices.

Figure 7:
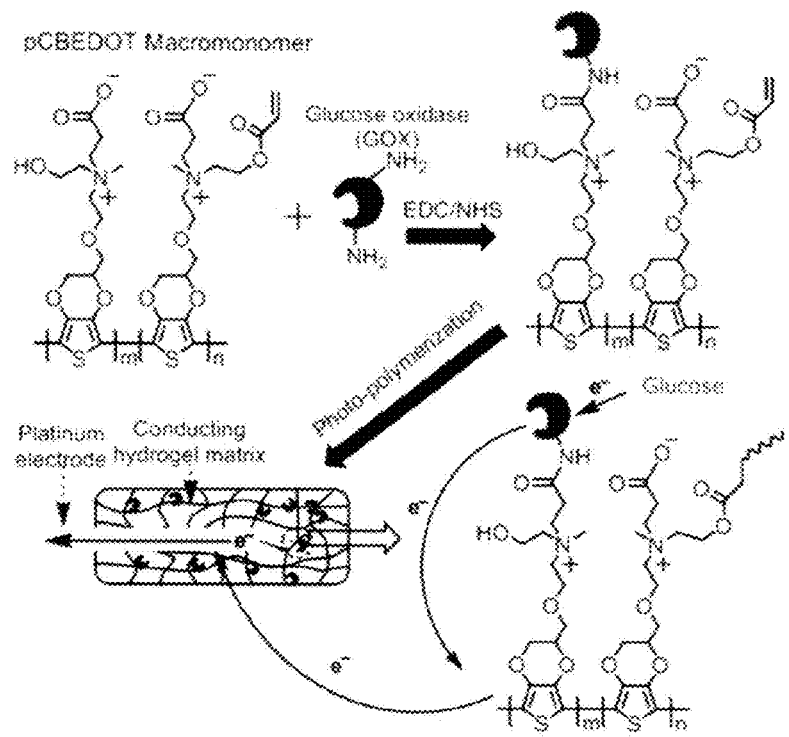
FIG. 7 is a schematic showing of the working principle of a pCBEDOT-based glucose sensor.

In particular, the conjugated polymer platforms and/or redox sensitive hydrogels of one or more embodiments of the present invention may be used to fabricate or operate bio or chemical sensors in medical devices. In some embodiments, the conjugated polymer platforms and/or redox sensitive hydrogels of the present invention may be used to fabricate electrodes that deliver or detect electrical signal in a biosensor. In some embodiments, the conjugated polymer platforms and/or redox sensitive hydrogels of the present invention may be used as a semiconductor to fabricate biosensors. In some embodiments, the conjugated polymer platforms and/or redox sensitive hydrogels of the present invention may be used to fabricate a transistor, transducer or supercapacitor in a biosensor. In some embodiments, the conjugated polymer platforms and/or redox sensitive hydrogels of the present invention may be used as electron or ion collectors in biosensors. In some embodiments, the conjugated polymer platforms and/or redox sensitive hydrogels of the present invention may be used as an antifouling and/or antimicrobial coating for biosensors to prevent biofouling and infection. FIG. 7 depicts a potential mechanism for using the conjugated polymer platforms and/or redox sensitive hydrogels of the present invention as a glucose sensor.

In some other embodiments, the conjugated polymer platforms and/or redox sensitive hydrogels of the present invention can be used to fabricate the tissue engineering scaffold for tissue regeneration.

In yet another aspect, the conjugated polymer platforms and/or redox sensitive hydrogels of the present invention may be used in a solar cell. In some of these embodiments, the conjugated polymer platforms and/or redox sensitive hydrogels of the present invention may be used as electron donor and electron acceptor materials in fabricating the solar cell. In some of these embodiments, conjugated polymer platforms and/or redox sensitive hydrogels of the present invention may be used as electron or ion collectors for the solar cell. In some of these embodiments, the conjugated polymer platforms and/or redox sensitive hydrogels of the present invention may be to fabricate electrodes that deliver or detect electrical signal in medical devices.

In yet another aspect, embodiments of the present invention are directed to a battery comprising conjugated polymer platforms and/or redox sensitive hydrogels described above. In some of these embodiments, the conjugated polymer platforms and/or redox sensitive hydrogels may be used as electron donor and electron acceptor materials in fabrication of the battery. In some of these embodiments, the conjugated polymer platforms and/or redox sensitive hydrogels may be used as electron or ion collectors in the battery.

In yet another aspect, embodiments of the present invention are directed to a supercapacitor comprising the conjugated polymer platforms and/or redox sensitive hydrogels described above. In some of these embodiments, the conjugated polymer platforms and/or redox sensitive hydrogels may be used as electron donor and electron acceptor materials in fabricating the supercapacitor. In some of these embodiments, the conjugated polymer platforms and/or redox sensitive hydrogels may be used as electron or ion collectors in the supercapacitor.

Figure 8:
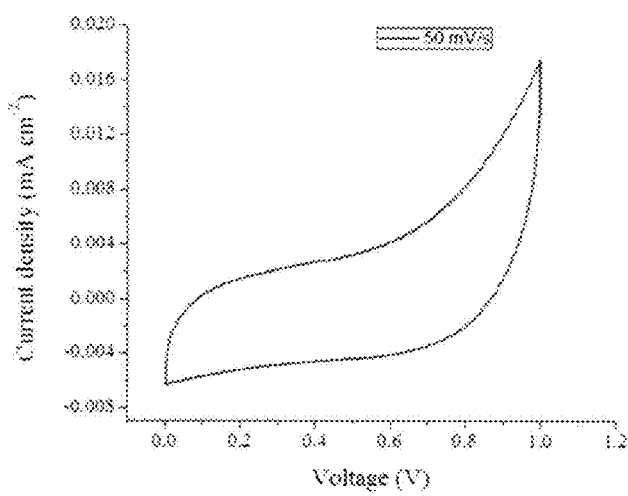
FIG. 8 is a cyclic voltammogram curve of the pCBTh hydrogel electrode at a scan rate of 50 mV·s$^{-1}$.

By way of example, electrochemical properties of pCBTh-co-ThMAA hydrogels according to embodiments of the present invention were studied in water using the alternating current (AC) electrochemical impedance spectroscopy (EIS) and cyclic voltammetry (CV). These pCBTh-co-ThMAA hydrogels showed high overall electrical conductivity, which were contributed by both ionic (3.67 mS cm$^{-1}$) and electronic (2.73×10$^{-4}$ mS cm$^{-1}$) transport. It has been found that electronic conductivity of the undoped pCBTh-co-ThMAA hydrogel of at least one embodiment of the present invention is comparable to that of a known doped polyaniline (PANi)/polyethylene glycol (PEG) hydrogel, but the ionic conductivity undoped pCBTh-co-ThMAA hydrogel is much higher due than the doped polyaniline (PANi)/PEG hydrogel due, it is believed, to the carboxybetaine side chains. Further, since these pCBTh-co-ThMAA hydrogels are chemically crosslinked, there are no concerns about the toxicity and deterioration of conductivity caused by the leakage of conducting polymer or dopant. Moreover, these pCBTh-co-ThMAA hydrogels have also been found to be stable and to show good cyclicability, which means that cyclic voltametry curve (See FIG. 8) remains same after many cycles. In some embodiments, the cyclic voltametry curve remains the same after 10 cycles.

As will be appreciated by those of skill in the art, the body responds to any foreign object by launching a series of physicochemical reactions, which are triggered by nonspecifically adsorbed proteins and eventually causes the formation of thick and non-conductive fibrous tissues. This foreign body response can be minimized, however, if the surface of implanted materials can effectively resist protein adsorption and cell attachment. Implanted electrochemical devices can be modified with antifouling materials to reduce nonspecific protein adsorption from complex medium, but in prior systems, these antifouling materials have been non-conductive. Non-conducting antifouling materials have been known to compromise the conducting performance of the electrode.

Figure 9:
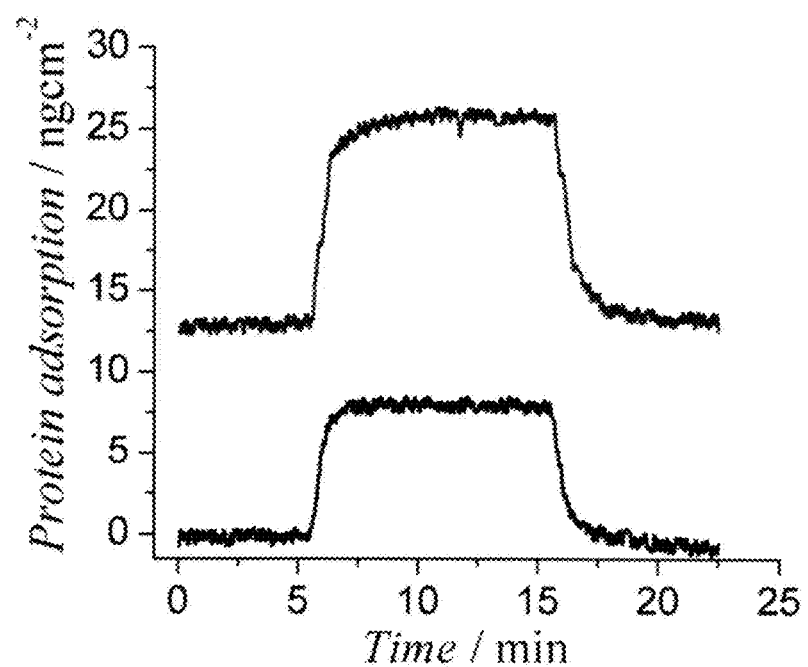
FIG. 9 are representative SPR sensorgrams showing the adsorption of 1 mgmL-1 bovine serum albumin (BSA) (upper) and fibrinogen (Fg) (lower) in PBS buffer on pCBTh-co-ThSH modified SPR substrates.

As set forth above, the zwitterionic side chains of CPs according to embodiments of the present invention may endow the conducting materials with superior antifouling properties and can resist protein adsorption on their surfaces without compromising electrical conductivity. To demonstrate these properties, a four channel SPR sensor was used to evaluate the protein adsorption on pCBTh coated SPR sensor chips. Cysteamine was conjugated to pCBTh-co-ThAA through Carbodiimides (EDC)/N-hydroxysuccinimide (NHS) chemistry to obtain pCBTh-co-ThSH. Incorporated thiol groups function as anchoring sites to immobilize the pCBTh-co-ThSH copolymer to the gold-coated SPR chips. It should be appreciated that in some embodiments free thiol groups can also function as reversible crosslinkers to form a redox sensitive hydrogel. Two commonly used proteins, bovine serum albumin (BSA) and human fibrinogen (Fg) that are most abundant in blood plasma, were applied to evaluate the antifouling property of pCBTh-co-ThSH coated surfaces at a concentration of 1 mg mL$^{-1}$. FIG. 9 shows representative SPR sensorgrams for fibrinogen adsorption on pCBTh over time. The amount of adsorbed proteins on pCBTh surface is less than 0.3 ng cm$^{-2}$ (the detection limit of the SPR sensor) for BSA and 0.45 ng cm$^{-2}$ for Fg. Fg adsorption on unmodified gold surface is around 225 ng cm$^{-2}$. Blood-contacting materials with less than 5 ng cm$^{-2}$ adsorbed protein [Fg] on their surface are referred to as "ultra-low fouling" materials and it is known that these materials do not trigger the platelet adhesion on the surface and subsequently delay the blood coagulation through contact activation pathway. Given their low levels protein adhesion, pCBTh-co-ThSH material of embodiments of the present invention qualify as "ultra-low fouling" materials.

Moreover, in some embodiments, pCBTh-co-ThMAA hydrogels according to the present invention also prevent or significantly reduce adhesion of cells. To demonstrate this, cell attachment studies were performed using bovine aorta endothelial cells (BAECs) on a pCBTh-co-ThMAA hydrogel according to at least some embodiments of the present invention and on control surfaces. pThAA hydrogel and tissue culture polystyrene (TCPS) were used as positive fouling control surfaces while a pCBMA hydrogel according to at least some embodiments of the present invention was used as a positive antifouling control surface. After 24 hours' incubation, pThAA hydrogel and TCPS surfaces were almost fully covered with BAEC cells. However, there was only a small amount of cells on the antifouling pCBTh-co-ThMAA and pCBMA hydrogel surfaces (See, FIGS. 10, 11). The amount of the attached BAEC cells on pCBTh-co-ThMAA hydrogel surfaces was found to be only 1.5% of that found on pThAA hydrogels (See Table 1) These results demonstrate that pCBTh-co-ThMAA hydrogels of the present invention are highly resistant to nonspecific cell attachment.

TABLE 1

Equilibrium water content and BAEC cell density on different surfaces and the percentage of the attached cells relative to pThAA hydrogel surfaces. (n = 3)

|  | pCBTh-co-ThMAA | pCBTh-co-RGD | pCBMA | pThAA | TCPS |
|---|---|---|---|---|---|
| % of water content | 96.3 | 98.8 | 93.7 | 80.4 | — |
| % of cell attachment | 1.5 ± 0.5 | 51.7 ± 5.6 | 2.2 ± 1.6 | 100 ± 10.2 | 82.9 ± 5.0 |

Figure 10:
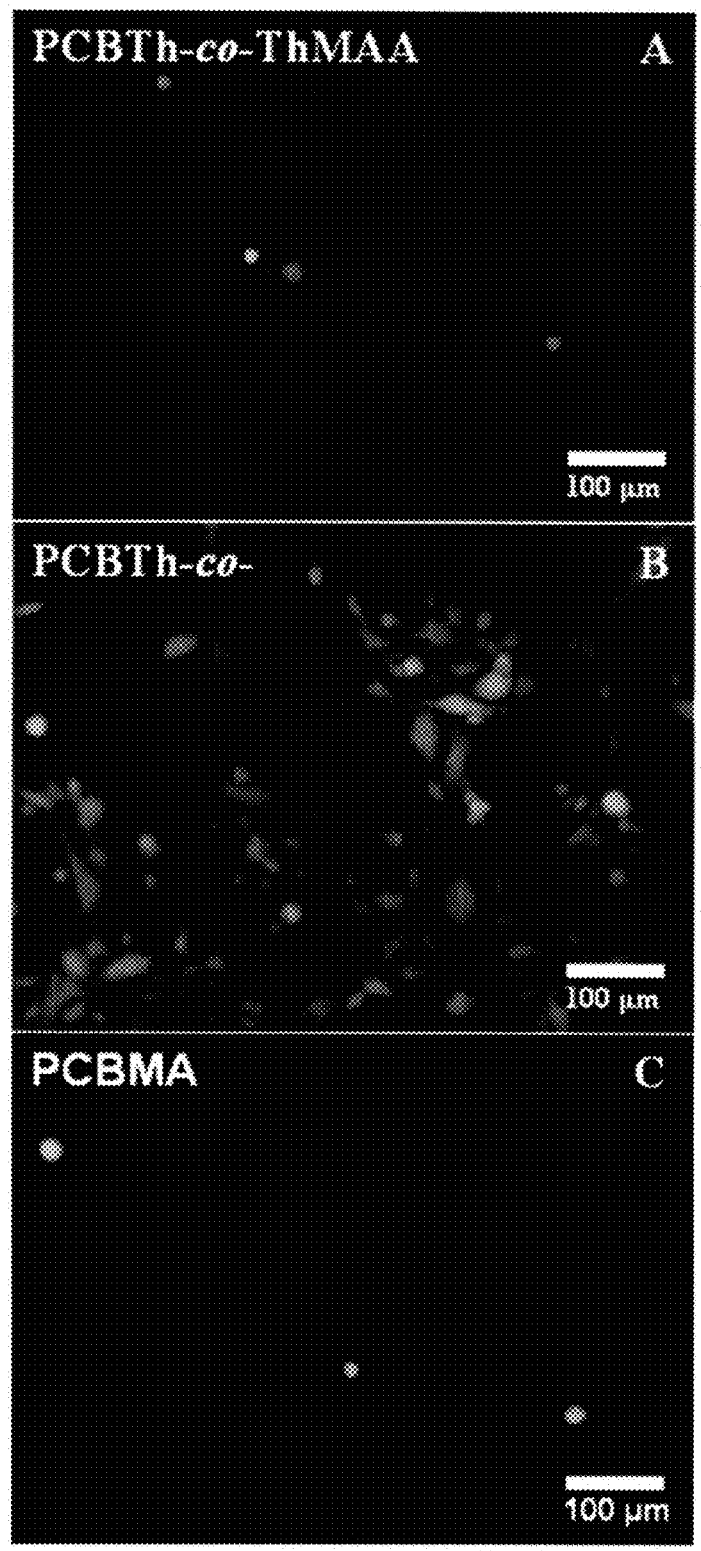
FIGS. 10A-E are representative fluorescence microscopy images of attached bovine aortic endothelial cells (BAEC) on pCBTh-co-ThMAA hydrogel (A), pCBTh-co-ThRGD hydrogel (B), pCBMA hydrogel (C), pThAA hydrogel (D), and TCPS (E) surfaces.
Figure 10:
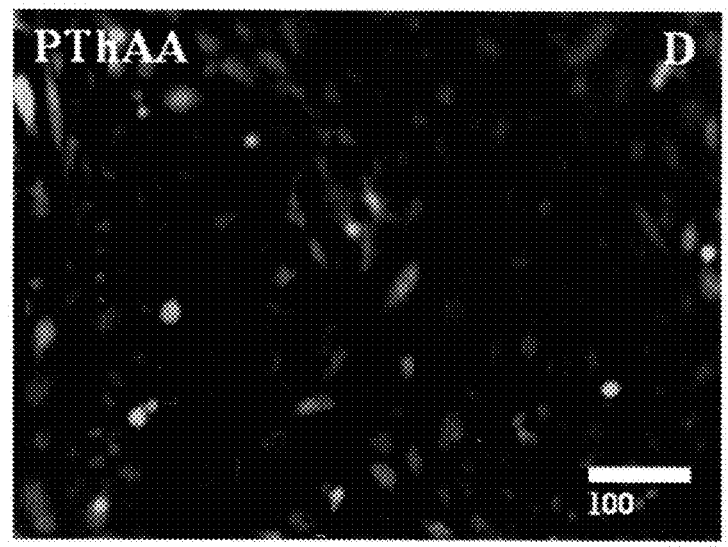
Figure 10:
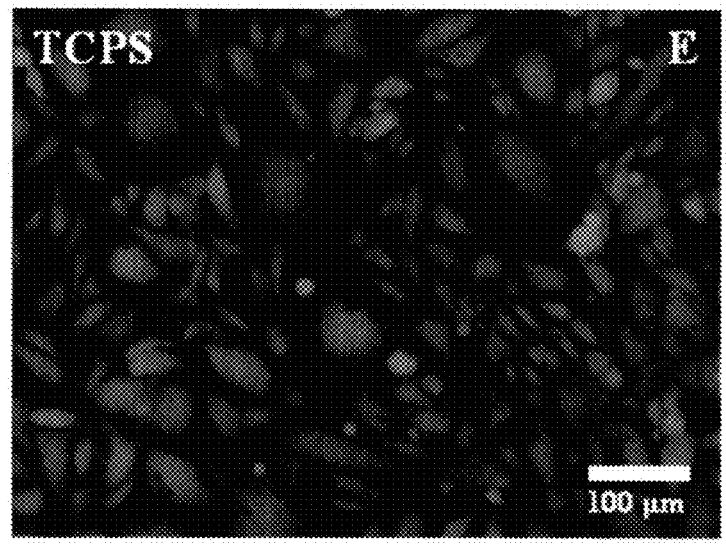
Figure 11:
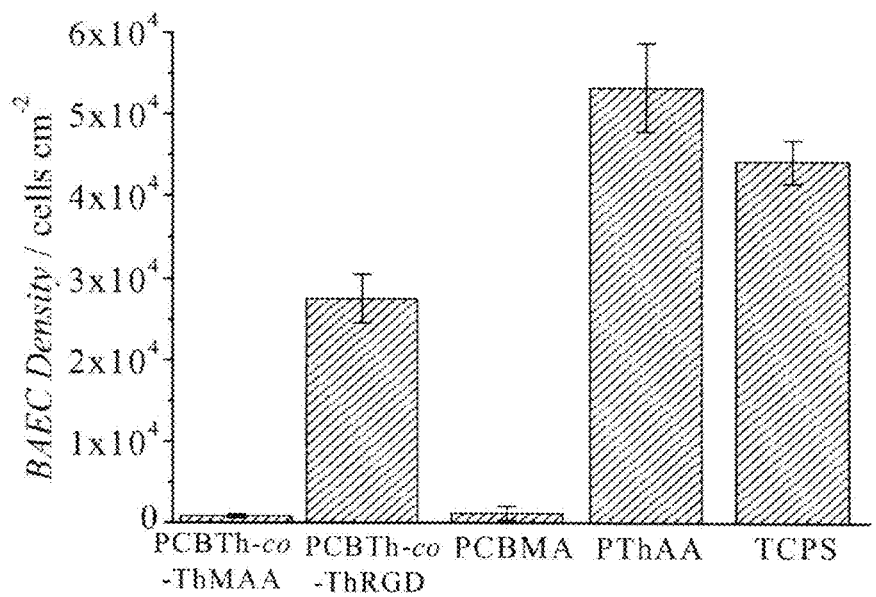

In some embodiments, it has been found that to improve the performance and the integration of implants with a biological system, those implants should not only resist the nonspecific attachment of unwanted cells, but should also allow and/or promote the attachment and proliferation of desired cells, such as endothelial cells, neural cells, etc. In some embodiments, hydrogels and polymers of the present invention provide functional groups at the biointerface to conjugate cell adhesion of molecules or other desired moieties in a controllable manner. To demonstrate this, a cell adhesion peptide, cysteine-arginine-glycine-asparagine-serine (CRGDS), was incorporated into a pCBTh-co-ThMAA hydrogel via the thiol-methacrylamide (MAA) by a Michael type reaction. As shown in FIGS. 10, 11 and Table 1, BAEC cells attach to the RGD-functionalized copolymer (pCBTh-co-ThRGD) hydrogel and the cell density on pCBTh-co-ThRGD hydrogels was 51.7% of that on pThAA hydrogels.

In some embodiments, the functional groups at the biointerface for conjugating cell adhesion of molecules or other desired moieties in a controllable manner include, without limitation, azides, alkynes, alkenes, amine, carboxylate, acrylates, thiol, 2-mercaptopyridine, ketones and aldehydes. The functional groups can be linked to the side chains and/or the conjugated backbones of conjugated polymers.

In some embodiments, CPs according to various embodiments of the present invention also exhibit interesting optical properties in response to environmental stimuli such as ionic strength, pH, temperature etc., which are very attractive for biosensing. The side chains of these CPs determines their overall planarization, solubility in a solvent and assembly behavior, which subsequently affects their optical properties. It should be appreciated that, based on the zwitterionic structure of pCBTh, the fluorescent properties of pCBTh will vary with changes in the pH. To demonstrate this, fluorescence spectra of a pCBTh prepared according to at least one embodiment of the present invention was measured in response to pH changes in 20 mM phosphate solution. It was found that the fluorescence property of pCBTh is very sensitive to pH. As shown in FIG. 12, the maximal emission signal occurred at the similar wavelength (around 548 nm) under different pH values, but fluorescence intensity changed dramatically. As the pH value of the solution changed from 12 to 2, the emission intensity of pCBTh at 548 nm gradually decreased and eventually dropped to about 30% of the original intensity.

Recently, CPs have been used to prepare optical pH sensors, since this technique eliminates the need for organic dyes. Optical pH sensors based on polypyrrole (pPy) and pANI have also been reported. The spectrum of polypyrrole obtained by chemical oxidation is pH dependent between pH 6 and 12, with a pKa around 8.6. Optical pANI pH sensors are suitable for pH measurement in the range of pH 2-12. These pCBTh have advantages for optical biosensing due to their high water-solubility, since they can provide a faster response to the environmental change and a stronger signal due to the homogeneity of the system. Fluorescence spectra of CPs are determined by both conducting polymer backbone and ionic side chains.

Implantable electrochemical devices have likewise drawn huge attention in recent years, since they can monitor biological responses continuously or deliver the electrical signal conveniently. For example, an implantable glucose sensor would be highly desired for diabetic people ((a) Wilson, G. S.; Zhang, Y.; Reach, G.; Moattisirat, D.; Poitout, V.; Thevenot, D. R.; Lemonnier, F.; Klein, J. C., Progress toward the Development of an Implantable Sensor for Glucose. *Clin Chem* 1992, 38 (9), 1613-1617; (b) Reach, G.; Wilson, G. S., Can Continuous Glucose Monitoring Be Used for the Treatment of Diabetes. *Anal Chem* 1992, 64 (6), A381-A386.). Implantable devices were used have been used to monitor electrical signals (See Hu, Y. B.; Wilson, G. S., A temporary local energy pool coupled to neuronal activity: Fluctuations of extracellular lactate levels in rat brain monitored with rapid-response enzyme-based sensor. *J Neurochem* 1997, 69 (4), 1484-1490 and Hu, Y. B.; Wilson, G. S., Rapid changes in local extracellular rat brain glucose observed with an in vivo glucose sensor. *J Neurochem* 1997, 68 (4), 1745-1752., the disclosure of which are incorporated by reference in their entirety) and bio-analytes (See O'Neill, R. D., Microvoltammetric techniques and sensors for monitoring neurochemical dynamics in vivo. A review. *The Analyst* 1994, 119 (5), 767-79, the disclosure of which are incorporated by reference in their entirety) in brain and they can be coupled with implantable drug delivery system for controlled release of drugs. In these devices, bioelectrodes are a core component for the delivery of charge and recording of electrical signal. As will be appreciated by those of skill in the art, the performance and lifetime of electrochemical devices are significantly influenced by interfacial mechanisms occurring at the device/biological environment interface, including biofouling, foreign body response, loss of structural integrity and infection.

The zwitterionic conducting materials of the present invention meet these challenges. Carboxybetaine (CB) materials have demonstrated superior antifouling properties of resisting proteins, mammalian cells, and microbes, excellent biocompatibility, as well as the capability of further functionalization for applications in biosensing and drug delivery. It has been found that CB polymers can stabilize conjugated proteins and significantly prolong protein's activity. This property is highly desired in biosensing, since the activity of enzymes/biomolecules is another limiting factor for the function of devices. Moreover, carboxylate groups of carboxybetaine polymers can also react with amine group via carbodiimides (EDC) EDC/N-hydroxysuccinimide (NHS) chemistry for bioconjugation. These properties make CB polymers very useful materials to fabricating biomedical devices to prevent protein adsorption, prolong the activity of biomolecules, provide functional groups for conjugation and increase the lifetime of the device.

In light of the foregoing, it should be appreciated that the present invention significantly advances the art by providing a zwitterionic conjugated polymer and hydrogel that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Thiophene-3-acetic acid (ThAA) was purchased from Matrix Scientific (Columbia, S.C., USA). 1,1'-Carbonyldiimidazole (CDI), 1-ethyl-3-(3-dimethylaminopropyl) carbodiimide (EDC), N-hydroxysuccinimide (NHS) and tris(2-carboxyethyl)phosphine hydrochloride (TCEP) were purchased from Chem-Impex International (Wood Dale, Ill., USA). Thermo initiator 2,2'-Azobis[2-(2-imidazolin-2-yl) propane]dihydrochloride (VA-044) was purchased from Wako Chemicals USA, Inc. (Richmond, Va., USA). Anhydrous tetrahydrofuran (THF), anhydrous chloroform, methanol, dichloromethane, ethyl acetate, acetonitrile, cystaminedihydrochloride, N,N'-dimethylethylenediamine, ethyl bromoacetate, anhydrous $FeCl_3$, sodium hydroxide, phosphate-buffered saline (PBS), human fibrinogen (Fg), bovine serum albumin (BSA), fetal bovine serum (FBS), 100× penicillin-streptomycin solution and fluorescein diacetate used as a cell viability stain were purchased from Sigma-Aldrich (St. Louis, Mo., USA). All chemicals were used as received without further purification. Bovine aorta endothelial cell (BAEC) was purchased from American Type Culture Collection (Manassas, Md., USA). Dulbecco's Modified Eagle's Medium (DMEM) was purchased from Life Technologies (Carlsbad, Calif., USA). Water used in all experiments was purified using a Millipore Milli-Q Direct 8 Ultrapure Water system (Billerica, Mass., USA). Cellulose dialysis membrane (1 k cut-off) was purchased from Spectrum Labs (Rancho Dominguez, Calif., USA). The AC impedance spectrum was measured by a Solartron Model 1260 Impedance/Gain-phase Analyzer with a Model 1287 potentiostat/galvanostat (UK). The UV-vis absorption spectra of polymers were collected on a Hewlett Packard 8453 UV-vis spectrophotometer (Palo Alto, Calif., USA). The fluorescence emission spectra of polymers were collected on a PerkinElmer LS 55 fluorescence spectrometer (Waltham, Mass., USA).

Example 1

Synthesis of N-(2-(dimethylamino)ethyl)-2-(thiophen-3-yl)acetamide (LXXXIII)(M2)

3-Thiopheneacetic acid (4.26 g, 30 mmol) was dissolved in 100 mL of anhydrous THF in a three-necked round bottom flask, followed by the addition of 5.88 g (36 mmol) of 1,1'-Carbonyldiimidazole (CDI). The mixture was cooled in an ice-bath (0° C.) and kept stirring for 20 minutes under a positive nitrogen flow. 3.28 mL of N,N'-dimethylethylenediamine (30 mmol) diluted in 10 mL of anhydrous THF was added drop wise with a dropping funnel. After the complete of addition, the mixture was warmed up to room temperature and kept stirring overnight. THF was removed with a rotary evaporator, and the product was purified with silica gel column chromatography (MeOH/CH$_2$Cl$_2$/ethyl acetate, 1/10/10 (v/v/v)). Pure product was obtained as a light yellowish liquid at 67% yield. $^1$H NMR (300 MHz, CDCl3) δ7.31 (m, 1H), 7.15 (s, 1H), 7.02 (d, 1H, J=4.8 Hz), 6.14 (s, 1H), 3.58 (s, 2H), 3.30 (m, 2H), 2.37 (t, 2H, J=6.0 Hz), 2.18 (s, 6H) (FIG. 13). $^{13}$C NMR (300 MHz, CDCl3) δ170.72, 135.26, 128.62, 126.38, 123.15, 57.89, 45.23, 38.29, 37.18 (FIG. 14).

Example 2

Synthesis of methyl thiophene-3-acetate (LXXXIV) (M3)

Methyl thiophene-3-acetate LXXXTV (M3) was synthesized following the method reported by Kim, L. Chen, Gong, Y. Osada, *Macromolecules* 1999, 32, 3964-3969, the disclosure of which is incorporated herein by reference in its entirety. Briefly, 3-Thiopheneacetic acid (8.52 g, 60 mmol) was dissolved in 50 mL of methanol with 2 drops of concentrated H$_2$SO$_4$. The mixture was heated in an oil bath and refluxed for 24 hours. After the removal of methanol, the crude product was re-dissolved in diethylether, washed with DI water and dried with anhydrous magnesium sulfate. Pure product was obtained after filtration and evaporation of solvent. The structure was analyzed and confirmed with $^1$H NMR spectroscopy.

Example 3

Synthesis of Homo-Polymer LXXXIV (P1)

6.11 g (37.7 mmole) of anhydrous FeCl$_3$ was suspended in 60 ml of anhydrous chloroform under a positive nitrogen flow. The mixture was cooled in an ice-bath (0° C.) and kept agitated for 30 minutes. 2.0 g (9.42 mmol) of compound 2 dissolved in 30 mL of dry chloroform was slowly added into the mixture during a period of one hour. Then the reaction was stirred for 24 hours at room temperature under nitrogen. After the reaction, the product was washed with chloroform and dried with rotary evaporator. Then it was re-dissolved in DI-water and purified through dialysis with cellulose dialysis membrane (1 k cut off). Water was changed daily for a week, and the solution was lyophilized to obtain compound LXXXIV (P1) at 20% yield. $^1$H NMR (300 MHz, D$_2$O) δ 6.6-7.6 (m, thiophene ring proton, 1H), 3.0-4.3 (m, thiophene ring —CH$_2$— and —NH—CH$_2$—, 4H), 2.7-3.0 (m, —CH$_2$—N(CH$_3$)$_2$, 2H), 2.0-2.7 (s, —CH$_3$, 6H) (FIG. 15).

Example 4

Synthesis of Homo-Polymer LXXXV (P2)

130 mg of the polymer (LXXXIV) (P1) of Example 3 was dissolved in 15 mL of methanol, followed by the addition of 0.2 mL of ethyl bromoacetate. The mixture was heated at 60° C. for 2 days under nitrogen. After concentrated with rotary evaporator, the product was precipitated in diethylether and dried under vacuum to obtain P2. $^1$H NMR (300 MHz, D$_2$O) δ 6.9-7.7 (m, thiophene ring proton, 1H), 4.2-4.6 (m, N(CH$_3$)$_2$—CH$_2$—C=O and —CH$_2$—CH$_3$, 4H), 3.6-4.1 (m, thiophene ring —CH$_2$— and —NH—CH$_2$—, 4H), 3.2-3.6 (s, —N(CH$_3$)$_2$, 6H), 2.9-3.1 (m, —CH$_2$—CH$_2$—N(CH$_3$)$_2$, 2H), 1.1-1.5 (s, —CH$_2$—CH$_3$, 3H) (FIG. 16).

Example 5

Synthesis of Homo-Polymer LIX (P3) (pCBTh)

The polymer LXXXV (P2) of Exhibit 4 was dissolved in DI water and passed through an ion exchange resin (Amberlite IRA-400 OH form) filled column to hydrolyze ethyl ester into the final zwitterionic form. Pure pCBTh (LIX) (P3) was obtained as a red powder after freeze-drying with 95% yield. $^1$H NMR (300 MHz, D$_2$O) δ 6.5-8.0 (m, thiophene ring proton, 1H), 3.5-4.5 (m, N(CH$_3$)$_2$—CH$_2$—C=O, thiophene ring —CH$_2$— and —NH—CH$_2$—, 6H), 3.0-3.5 (s, —N(CH$_3$)$_2$, 6H), 2.2-2.6 (s, —CH$_2$—CH$_2$—N(CH$_3$)$_2$, 2H) (FIG. 17).

Example 6

Synthesis of Copolymer LXI (P7) (pCBTh-co-ThMAA) and LX (P8) (pCBTh-co-ThSH)

Copolymer LXI (P7) (pCBTh-co-ThMAA) and LX (P8) (pCBTh-co-ThSH) were synthesized according to Scheme 1, below.

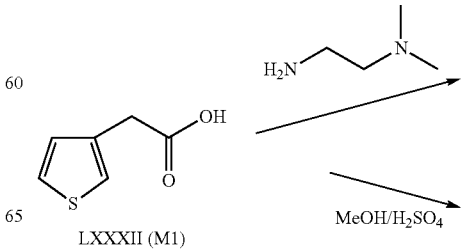

Scheme 2

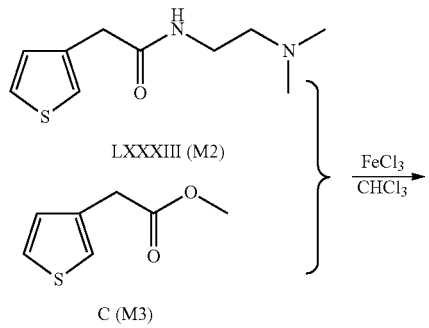
LXXXIII (M2)
C (M3)
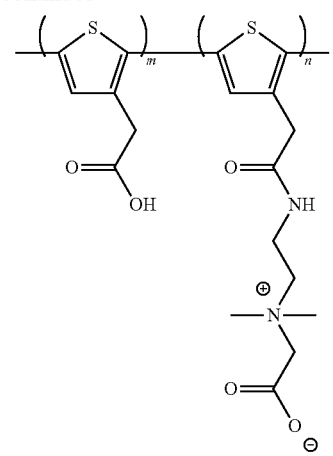
LXXXVIII (P6) (pCBTh-co-ThAA)
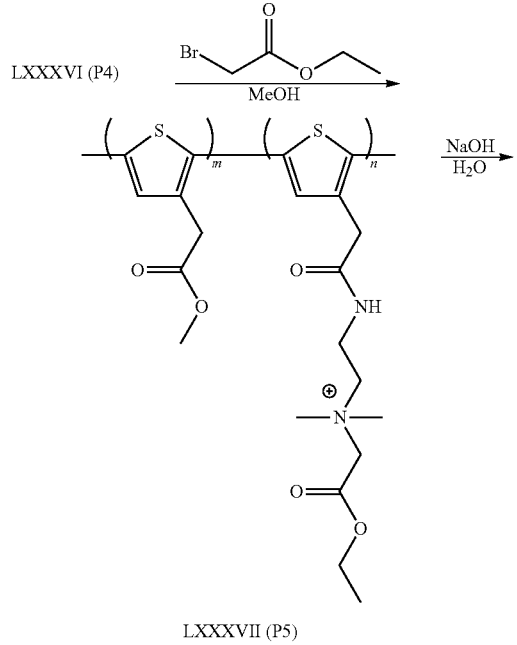
LXXXVI (P4)
LXXXVII (P5)
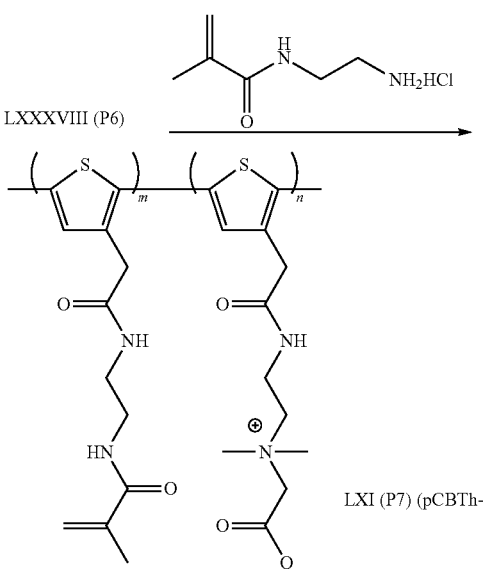
LXI (P7) (pCBTh-co-ThMAA)
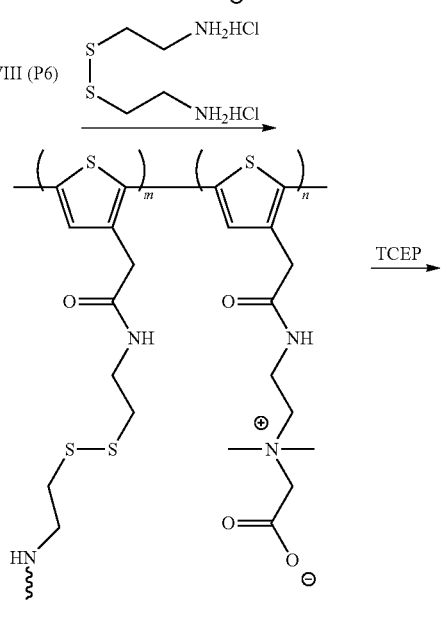
LXXXIX

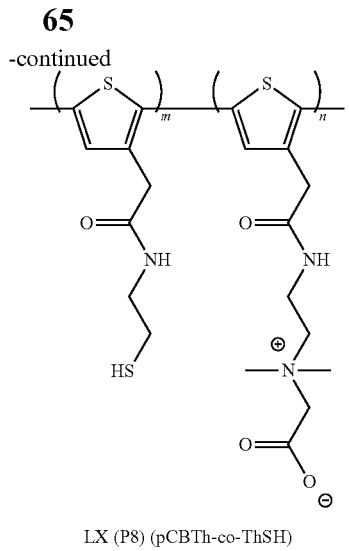

LX (P8) (pCBTh-co-ThSH)

Monomers LXXXIII (M2) and LXXXIV (M3) were pre-mixed at a feeding ratio of 80:20 for the oxidative polymerization with anhydrous $FeCl_3$ to form copolymer LXXXVI (P4). The procedures for synthesis of copolymer LXXXVIII P6 from copolymer LXXXVI (P4) followed similar to that for the synthesis of homopolymer LIX (P3) described above. (See Scheme 1, above). After purification by dialysis with cellulose dialysis membrane (1 k cut off), compound LXXXVIII (P6) (pCBTh-co-ThAA) was separated into two portions and submitted to two separate reactions to synthesize compound LXI (P7) (pCBTh-co-ThMAA) and compound LX (P8) (pCBTh-co-ThSH).

In the first reaction, compound LXXXVIII (P6) was reacted with 2-aminoethyl methacrylamide hydrochloride (See as described in X. Jiang, M. Ahmed, Z. Deng, R. Narain, *Bioconjugate Chem.* 2009, 20, 994-1001 the disclosure of which is incorporated herein by reference in its entirety) in the presence of EDC to obtain self-crosslinkable copolymer compound LXI (P7) (pCBTh-co-ThMAA). After dialysis, the substitution ratio of methacrylamide double bond to thiophene unit was about 10% based on $^1$HNMR integral values. $^1$H NMR (300 MHz, $D_2O$) δ 6.6-8.0 (m, 1H), 5.5-5.8 (m, 1H), 5.2-5.5 (m, 1H), 3.5-4.5 (m, 8H), 3.0-3.5 (s, —$N(CH_3)_2$, 6H), 2.5-3.0 (m, 4H), 1.7-2.0 (s, 3H) (See FIG. 18).

In the second reaction, LXXXVIII (P6) was reacted with cystamine dihydrochloride using EDC/NHS chemistry as described in X. Jiang, M. Ahmed, Z. Deng, R. Narain, *Bioconjugate Chem.* 2009, 20, 994-1001 the disclosure of which is incorporated herein by reference in its entirety, followed by the reduction of disulfide with tris(2-carboxyethyl)phosphine hydrochloride (TCEP) to obtain copolymer LX (P8) (pCBTh-co-ThSH). The incorporation of free thiol groups were designed for the immobilization of copolymers LX (P8) (pCBTh-co-ThSH) on gold-coated SPR sensor chips. Since the resonance from thiol (SH) containing side chain was not resolved from the overlapping signals, the actual substitution ratio of thiol groups cannot be calculated from $^1$H NMR. $^1$H NMR (300 MHz, $D_2O$) δ 6.6-8.0 (m, 1H), 3.5-4.5 (m, 8H), 2.8-3.5 (s, —$N(CH_3)_2$, 6H), 2.6-2.8 (m, 2H), 2.2-2.4 (m, 2H) (See FIG. 19).

Example 7

Synthesis of pCBTh-co-ThRGD Copolymer

A cysteine containing cell adhesion peptide, cysteine-arginine-glycine-asparagine-serine (CRGDS), was conjugated to the double bond on LXI (P7) (pCBTh-co-ThMAA) via the thiol-methacrylamide (MAA) Michael type reaction in $D_2O$ solution. $^1$H NMR was used to monitor the reaction in real time. The ratio of double bonds to thiophene units changed from 10-12% (before conjugation) to 9% (after conjugation). So the RGDs substitution ratio is estimated to be about 1-2%. $^1$H NMR (300 MHz, $D_2O$) δ 6.6-8.0 (m, 1H), 5.4-5.6 (m, 1H), 5.1-5.4 (m, 1H), 3.4-4.2 (m, 8H), 2.9-3.3 (s, —$N(CH_3)_2$, 6H), 2.5-3.0 (m, 4H), 1.6-2.2 (s, 7H) (See FIG. 20).

Example 8

Hydrogel Preparation pCBTh-co-ThMAA hydrogels were prepared via thermo-initiated polymerization as follows. 100 mg of copolymer LXI (P7) was dissolved in 400 µL aqueous solution with 0.5 wt % of thermo-initiator (VA-044). Then the solution was transferred into a mold made of two quartz slides separated by a 1 mm thick PTFE spacer and polymerized at 50° C. for overnight. The gel was equilibrated in DI water and water was changed daily for 7 days. The wet weight of the hydrogel sample was measured after the removal of excess water. pThAA hydrogel was prepared according to the method reported in D. Mawad, E. Stewart, D. L. Officer, T. Romeo, P. Wagner, K. Wagner, G. G. Wallace, *Adv. Funct. Mater.* 2012, 22, 2692-2699, the disclosure of which is incorporated herein by reference in its entirety, and used as a control in this study.

Example 9

Polymer Film Preparation

Polymer thin films were prepared with a graft-to method. Copolymer LX (P8) (pCBTh-co-ThSH) with free thiol end group was prepared at the concentration of 10 mg/mL in a mixed solvent of 90% DI-water and 10% methanol by volume. 400 µL of polymer solution was drop-casted on a gold-coated SPR chip. It was put in a petri-dish and left undisturbed until solvent evaporated at room temperature. Sample was washed with PBS and dried with filtered air before the SPR measurement.

Example 10

Electrochemical Study

The AC impedance spectrum of the hydrogel of Example 7, above was measured by a Solartron Model 1260 Impedance/Gain-phase Analyzer with a Model 1287 potentiostat/galvanostat in the frequency range from 0.1 mHz to 100 kHz at low amplitude voltage (~10 mV). The hydrogel sample were cut into a disc with a diameter of 6.8 mm and put between to stainless steel electrodes. The ionic and electronic conductivities of hydrogels were calculated with using the method reported in A. E. Javier, S. N. Patel, D. T. Hallinan, V. Srinivasan, N. P. Balsara, *Angew. Chem., Int. Ed.* 2011, 50, 9848-9851, the disclosure of which is incorporated herein by reference in its entirety. The ionic resistance, Ri, can be determined from the relationship $1/R1=1/Ri+1/Re$, where R1 is the high-frequency semi-circle resistance from impedance data and Re is the electrical resistance measured under small applied DC potentials (−30 mV-+30 mV) using the potentiostat. Cyclic voltammetry (CV) can provide potentiodynamic electrochemical measurements and stability measurement. (See, W. S. Huang, B. D. Humphrey, A. G. Macdiarmid, *J. Chem. Soc., Faraday Trans.* 1986, 82, 2385-2400, the disclosure of which is incorporated herein by reference in its entirety). FIG. 21 shows CV curves and the impedance curve and of pCBTh-co-ThMAA hydrogel based electrodes using a two electrode system. Rate-dependent CVs with the potential window of 0 to 1 V at scan rates of 5, 10, 20, 30 and 50 mV/s. CV were recorded in the potential range of 0-1 V using the potentiostat. The complex diagram shows a lineal behavior at low frequencies, which indicates that the mass transport is the dominant mechanism. The capacitive response at medium frequencies denotes the current carries within the material.

Example 11

Protein Adsorption Study

A four-channel SPR sensor was used to measure protein adsorption on pCBTh-co-ThSH coated surface. Firstly, PBS solution at 50 µL min$^{-1}$ flow rate was used to obtain a baseline signal. 1 mg mL$^{-1}$ of fibrinogen solution and 1 mg mL$^{-1}$ of BSA were then injected into different channels for 10 minutes followed by a PBS wash to remove any loosely bound proteins. The amount of adsorbed proteins was calculated as the change in wavelength before and after protein injection.

Example 12

Cell Adhesion Study

BAECs were chosen to study cell adhesion on hydrogel surfaces, following a similar procedure set forth in B. Cao, L. Li, H. Wu, Q. Tang, B. Sun, H. Dong, J. Zhe, G. Cheng, *Chem. Commun.* 2014, 50, 3234-3237, the disclosure of which is incorporated herein by reference in its entirety. Hydrogel samples were equilibrated in DI-water and then transferred to sterilized PBS, exposed under UV for half an hour before the experiment. BAECs were seeded on different hydrogel and control surfaces at a concentration of $10^5$ cells mL$^{-1}$ in DMEM containing 10% FBS and 1% penicillin-streptomycin, and kept in an incubator with 5% $CO_2$ at 37° C. for 24 hours. After the incubation, medium was removed from the wells and changed to the staining solution that prepared in sterilized PBS as follows. Fluorescein diacetate was dissolved at a concentration of 10 mg mL$^{-1}$ in acetone, then 50 µL of the solution was diluted in 10 mL sterilized PBS and used for staining the cells. After incubated for 5 min with the staining solution, surface cell coverage and cell morphology was visualized and imaged with an Olympus IX70 fluorescence microscope equipped with a FITC filter at ×10 magnification.

Example 13

Water Content Measurement

The water content is a basic property of hydrogel materials for biomedical applications. The wet weight of the hydrogel sample was measured after the removal of excess water. Dry weight was recorded after the samples had been freeze-dried for 48 hours. The water contents of hydrogels (See Table 1, above) are calculated by (Wet weight−Dry weight)/Wet weight×100%.

Example 14

Cytotoxicity Study

The cytotoxicity of the zwitterionic polymer was studied with various concentrations of pCBTh. 100 µL of BAEC cells solution, at a concentration of $10^5$ cells mL$^{-1}$, were incubated in a 96 well plate for 24 hours with different concentrations (0.5, $5 \times 10^{-2}$, $5 \times 10^{-3}$, $5 \times 10^{-4}$ and $5 \times 10^{-5}$ mgmL$^{-1}$) of pCBTh. Six replicates were used for each concentration. As a control, the same cells were also incubated at the same conditions without adding pCBTh. After 24 hours incubation, cells were stained with the same method as discussed in cell adhesion study of Example 11 above. Representative fluorescence images of surviving cells were taken for each condition with an Olympus IX70 fluorescence microscope equipped with a FITC filter at ×10 magnification. The number of cells was counted by three replicates and relative viability was calculated and summarized in FIG. 5.

Example 15

Optical Properties Study

The UV-vis absorption spectra of pCBTh were collected on a Hewlett Packard 8453 UV-vis spectrophotometer. Samples were prepared in 20 mM PBS buffer solution at different pH, from pH 2 to pH 12. Fluorescence emission spectra were collected on a PerkinElmer LS 55 fluorescence spectrometer, excited at 411 nm.

What is claimed is:

1. A conjugated polymer platform for use with bioelectronics, biosensing, regenerative medicine, or energy applications comprising a conjugated polymer backbone having one or more zwitterionic side chains and one or more other side chains selected from the group consisting of crosslinking side chains, side chains for securing said conjugated polymer platform to a surface, redox sensitive side chains, both positively and negatively charged side chains, and combinations thereof, wherein said zwitterionic side chains further comprise a carboxybetaine group, a sulfobetaine group, a phosphobetaine group or combinations thereof.

2. The conjugated polymer platform of claim 1 wherein said other side chain comprises one or more crosslinking side chains.

3. The conjugated polymer platform of claim 1 wherein said other side chain comprises one or more side chains for securing said conjugated polymer platform to a surface.

4. The conjugated polymer platform of claim 1 wherein said other side chain comprises one or more redox sensitive side chains.

5. The conjugated polymer platform of claim 1 wherein said other side chain comprises positively and negatively charged side chains.

6. The conjugated polymer platform of claim 1 wherein said conjugated polymer backbone is selected from the group consisting of poly(thiophene)s, poly(fluorene)s, poly(phenylene)s, poly(pyrene)s, poly(azulene)s, poly(naphthalene)s, poly(pyrrole)s, poly(carbazole)s, poly(indole)s, poly(azepine)s, poly(aniline)s, poly(3,4-ethylenedioxythiophene)s, poly(p-phenylene sulfide) s, poly(acetylene)s, poly(p-phenylene vinylene)s, and combinations thereof.

7. The conjugated polymer platform of claim 1 wherein said zwitterionic side chains have a formula selected from the group consisting of:

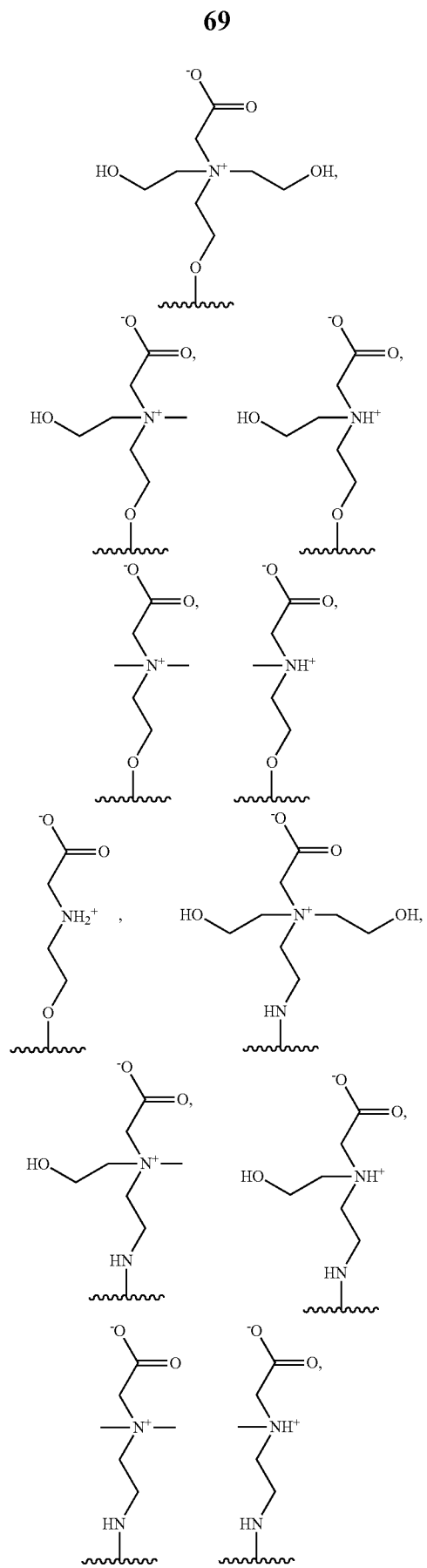
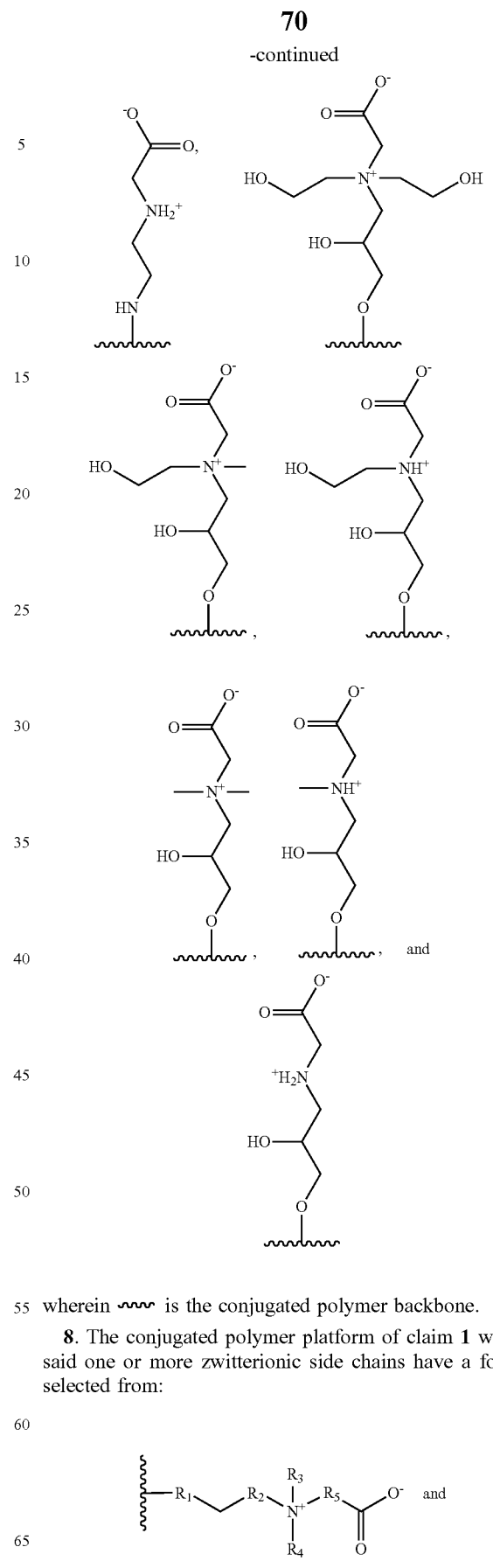
wherein ∿ is the conjugated polymer backbone.
8. The conjugated polymer platform of claim 1 wherein said one or more zwitterionic side chains have a formula selected from:

-continued

[Structure: backbone-R₁-C(O)-CH₂-R₂-N⁺(R₃)(R₄)-R₅-C(O)-O⁻]

wherein R₁ is —O—, —NH—, —C(O)NH—, —CH₂C(O)NH—, —CH₂CH₂C(O)NH—, —(CH₂)$_m$C(O)NH—, —NHC(O)—, —NHC(O)CH₂—, —NHC(O)CH₂CH₂—, —NHC(O)(CH₂)$_m$—, —(CH₂)$_m$NHC(O)(CH₂)$_n$—, —(CH₂)$_m$NHC(O)O(CH₂)$_n$—, —(CH₂)$_m$OC(O)NH(CH₂)$_n$—, —(CH₂)$_m$C(O)NH(CH₂)$_n$—, —NHC(O)(CH₂)$_m$C(O)NH—, —OC(O)(CH₂)$_m$C(O)NH—, —O(CH₂)$_m$C(O)NH—, —NHC(O)(CH₂)$_m$O—, —NHC(O)(CH₂)$_m$C(O)O—, —C(O)O—, —CH₂C(O)O—, —CH₂CH₂C(O)O—, —(CH₂)$_m$C(O)O—, OC(O)—, —OC(O)CH₂—, —OC(O)CH₂CH₂—, —OC(O)(CH₂)$_m$—, —OC(O)(CH₂)$_m$C(O)O—, —OC(O)(CH₂)$_m$O—, —O(CH₂)$_m$C(O)O—, —(CH₂)$_m$OC(O)(CH₂)$_n$—, —(CH₂)$_m$C(O)O(CH₂)$_n$—, —CH₂O—, —CH₂CH₂O—, —CH₂CH₂CH₂O—, —CH₂CH₂CH₂CH₂O—, —CH₂CH₂CH₂CH₂CH₂O—, —CH₂CH₂CH₂CH₂CH₂CH₂O—, —(CH₂)$_m$O—, —O(CH₂)$_m$O—, —O(CH₂)$_m$—, —(CH₂)$_m$—, —O(CH₂CH₂O)$_m$, —(OCH₂CH₂)$_m$— or —(CH₂CH₂O)$_m$—; R₂ is —CH₂—, —CH₂CH₂—, —CH₂CH₂CH₂—, —CH₂CH₂CH₂CH₂—, —CH₂CH₂CH₂CH₂CH₂—, or —(CH₂)$_x$—; R₃ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; R₄ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; R₅ is —CH₂—, —CH₂CH₂—, —CH₂CH₂CH₂—, —CH₂CH₂CH₂CH₂—, —CH₂CH₂CH₂CH₂CH₂—, or —(CH₂)$_y$—; m, n, x and y are each an integer from 1 to 20; and ∼∼∼ is the conjugated polymer backbone.

9. The conjugated polymer platform of claim 1 wherein said one or more zwitterionic side chains have the formula:

[Structure: backbone-R₁-R₂-CH₂CH₂-S-R₃-N⁺(R₄)(R₅)-R₆-C(O)-O⁻]

wherein R₁ is —O—, —NH—, —C(O)NH—, —CH₂C(O)NH—, —CH₂CH₂C(O)NH—, —(CH₂)$_m$C(O)NH—, —NHC(O)—, —NHC(O)CH₂—, —NHC(O)CH₂CH₂—, —NHC(O)(CH₂)$_m$—, —(CH₂)$_m$NHC(O)(CH₂)$_n$—, —(CH₂)$_m$NHC(O)O(CH₂)$_n$—, —(CH₂)$_m$C(O)NH(CH₂)$_n$—, —(CH₂)$_m$C(O)NH(CH)$_n$—, —NHC(O)(CH₂)$_m$C(O)NH—, —OC(O)(CH₂)$_m$C(O)NH—, —O(CH₂)$_m$C(O)NH—, —NHC(O)(CH₂)$_m$O—, —NHC(O)(CH₂)$_m$C(O)O—, —C(O)O—, —CH₂C(O)O—, —CH₂CH₂C(O)O—, —(CH₂)$_m$C(O)O—, OC(O)—, —OC(O)CH₂—, —OC(O)CH₂CH₂—, —OC(O)(CH₂)$_m$—, —OC(O)(CH₂)$_m$C(O)O—, —OC(O)(CH₂)$_m$O—, —O(CH₂)$_m$C(O)O—, —(CH₂)$_m$OC(O)(CH₂)$_n$—, —(CH₂)$_m$C(O)O(CH₂)$_n$—, —CH₂O—, —CH₂CH₂O—, —CH₂CH₂CH₂O—, —CH₂CH₂CH₂CH₂O—, —CH₂CH₂CH₂CH₂CH₂O—, —CH₂CH₂CH₂CH₂CH₂CH₂O—, —(CH₂)$_m$O—, —O(CH₂)$_m$O—, —O(CH₂)$_m$—, —(CH₂)$_m$—, —O(CH₂CH₂O)$_m$, —(OCH₂CH₂)$_m$— or —(CH₂CH₂O)$_m$—; R₂ is —CH₂—, —CH₂CH₂—, —CH₂CH₂CH₂—, —CH₂CH₂CH₂CH₂—, —CH₂CH₂CH₂CH₂CH₂—, —(CH₂)$_x$—, —NHC(O)—, —NHC(O)CH₂—, —NHC(O)CH₂CH₂—, NHC(O)(CH₂)$_x$—, NHC(O)O(CH₂)$_x$—, OC(O)NH(CH₂)$_x$—, OC(O)NH(CH₂)$_x$—, —OC(O)—, —OC(O)CH₂—, —OC(O)CH₂CH₂— or —OC(O)(CH₂)$_x$—; R₃ is —CH₂CH₂—, —CH₂CH₂CH₂—, —CH₂CH₂CH₂CH₂—, —CH₂CH₂CH₂CH₂CH₂—, or —(CH₂)$_y$—; R₄ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; R₅ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; R₆ is —CH₂—, —CH₂CH₂—, —CH₂CH₂CH₂—, —CH₂CH₂CH₂CH₂—, —CH₂CH₂CH₂CH₂CH₂— or —(CH₂)$_z$—; m, n, x, y and z are each an integer from 1 to 20; and ∼∼∼ is the conjugated polymer backbone.

10. The conjugated polymer platform of claim 1 wherein said one or more zwitterionic side chains have the formula:

[Structure: backbone-R₁-R₂-CH₂CH₂-S-R₃-C(N⁺(R₄)(R₅)(R₆))-C(O)-O⁻]

wherein R₁ is —O—, —NH—, —C(O)NH—, —CH₂C(O)NH—, —CH₂CH₂C(O)NH—, —(CH₂)$_m$C(O)NH—, —NHC(O)—, —NHC(O)CH₂—, —NHC(O)CH₂CH₂—, —NHC(O)(CH₂)$_m$—, —(CH₂)$_m$NHC(O)(CH₂)$_n$—, —(CH₂)$_m$NHC(O)O(CH₂)$_n$—, —(CH₂)$_m$C(O)NH(CH₂)$_n$—, —(CH₂)$_m$C(O)NH(CH₂)$_n$—, —NHC(O)(CH₂)$_m$C(O)NH—, —OC(O)(CH₂)$_m$C(O)NH—, —O(CH₂)$_m$C(O)NH—, —NHC(O)(CH₂)$_m$O—, —NHC(O)(CH₂)$_m$C(O)O—, —C(O)O—, —CH₂C(O)O—, —CH₂CH₂C(O)O—, —(CH₂)$_m$C(O)O—, OC(O)—, —OC(O)CH₂—, —OC(O)CH₂CH₂—, —OC(O)(CH₂)$_m$—, —OC(O)(CH₂)$_m$C(O)O—, —OC(O)(CH₂)$_m$O—, —O(CH₂)$_m$C(O)O—, —(CH₂)$_m$OC(O)(CH₂)$_n$—, —(CH₂)$_m$C(O)O(CH₂)$_n$—, —CH₂O—, —CH₂CH₂O—, —CH₂CH₂CH₂O—, —CH₂CH₂CH₂CH₂O—, —CH₂CH₂CH₂CH₂CH₂O—, —CH₂CH₂CH₂CH₂CH₂CH₂O—, —(CH₂)$_m$O—, —O(CH₂)$_m$O—, —O(CH₂)$_m$—, —(CH₂)$_m$—, —O(CH₂CH₂O)$_m$, —(OCH₂CH₂)$_m$— or —(CH₂CH₂O)$_m$—; R₂ is —CH₂—, —CH₂CH₂—, —CH₂CH₂CH₂—, —CH₂CH₂CH₂CH₂—, —CH₂CH₂CH₂CH₂CH₂—, —(CH₂)$_x$—, —NHC(O)—, —NHC(O)CH₂—, —NHC(O)CH₂CH₂—, NHC(O)(CH₂)$_x$—, —OC(O)—, —OC(O)CH₂—, —OC(O)CH₂CH₂— or —OC(O))(CH₂)$_x$—; R₃ is —CH₂CH₂—, —CH₂CH₂CH₂—, —CH₂CH₂CH₂CH₂—, —CH₂CH₂CH₂CH₂CH₂— or —(CH₂)$_y$—; R₄ is —H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; R₅ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, —CH₂CH₂CH₂CH₂CH₂OH; R₆ is H, —CH₃, CH₂CH₃, —CH₂CH₂CH₃, —CH₂CH₂CH₂CH₃, —CH₂CH₂OH, —CH₂CH₂CH₂OH, —CH₂CH₂CH₂CH₂OH, or —CH₂CH₂CH₂CH₂CH₂OH; m, n, x and y are each an integer from 1 to 20; and ∼∼∼ is the conjugated polymer backbone.

11. The conjugated polymer platform of claim 1 wherein said one or more zwitterionic side chains have a formula:

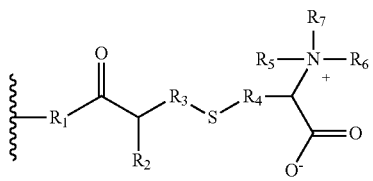

wherein $R_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —C(O)NH(CH$_2$)$_n$—, —NHC(O)(CH$_2$)$_n$—, —(CH$_2$)$_m$C(O)NH(CH$_2$)$_n$—, —NHC(O)(CH$_2$)$_m$C(O)NH—, OC(O)(CH$_2$)$_m$C(O)NH—, —O(CH$_2$)$_m$C(O)NH—, —NHC(O)(CH$_2$)$_m$O—, —CH$_2$C(O)O—, —OC(O)CH$_2$—, —OC(O)CH$_2$CH$_2$—, —OC(O)(CH$_2$)$_m$—, —OC(O)(CH$_2$)$_m$O—, —(CH$_2$)$_m$OC(O)(CH$_2$)$_n$—, —(CH$_2$)$_m$C(O)O(CH$_2$)$_n$—, —C(O)O(CH$_2$)$_n$—, —OC(O)(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; $R_2$ is —CH$_2$—CH$_2$CH$_3$, or —CH$_2$CH$_2$CH$_3$; $R_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_x$—; $R_4$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_y$—; $R_5$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_6$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_7$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m, n, x and y are each an integer from 1 to 20; and ⌇⌇ is the conjugated polymer backbone.

12. The conjugated polymer platform of claim 1 wherein said one or more zwitterionic side chains have a formula selected from:

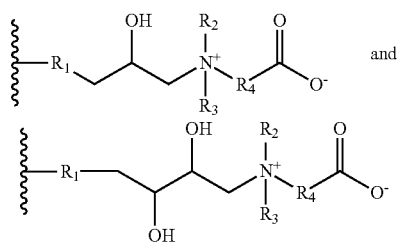

wherein $R_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH)—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; $R_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH, $R_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_x$—; m, n and x are each an integer from 1 to 20; and ⌇⌇ is the conjugated polymer backbone.

13. The conjugated polymer platform of claim 1 wherein said one or more zwitterionic side chains have the formula:

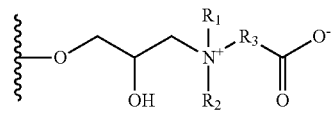

wherein $R_1$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_2$ are H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_n$—; n is an integer from 1 to 20; and ⌇⌇ is the conjugated polymer backbone.

14. The conjugated polymer platform of claim 1 wherein said one or more zwitterionic side chains have the formula:

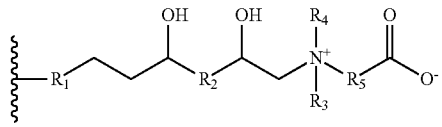

wherein $R_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$C(O)NH (CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$ O)$_m$—; R$_2$ is —CH$_2$, CH$_2$CH$_2$—, —CH$_2$CH$_2$CH$_2$—, —CH$_2$CH$_2$CH$_2$CH$_2$—, or —(CH$_2$)$_x$—, R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_y$—; m, n, x and y are each an integer from 1 to 20; and ∼∼∼ is the conjugated polymer backbone.

15. The conjugated polymer platform of claim 1 wherein said one or more zwitterionic side chains have a formula selected from:

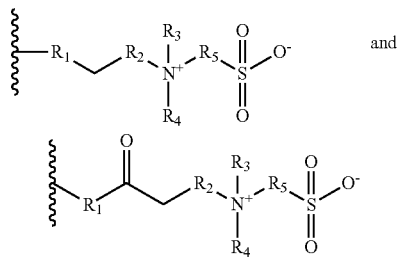

and wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH)$_m$O—, —O(CH$_2$)$_m$C(O)O—, —(CH$_2$)$_m$OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$—, —(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_x$—; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_y$—; m, n, x and y are each an integer from 1 to 20; and ∼∼∼ is the conjugated polymer backbone.

16. The conjugated polymer platform of claim 1 wherein said one or more zwitterionic side chains have the formula:

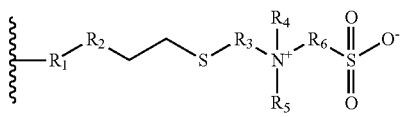

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$C(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$—, —(OCH$_2$CH$_2$)$_m$— or —(CH$_2$CH$_2$O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—, —NHC(O)—, —NHC(O)CH$_2$—, —NHC(O)CH$_2$CH$_2$—, NHC(O)(CH$_2$)$_x$—, —OC(O)—, —OC(O)CH$_2$—, —OC(O)CH$_2$CH$_2$— or —OC(O))(CH$_2$)$_x$—; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$—; R$_4$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_6$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_z$—; m, n, x, y and z are each an integer from 1 to 20; and ∼∼∼ is the conjugated polymer backbone.

17. The conjugated polymer platform of claim 1 wherein said one or more zwitterionic side chains have a formula selected from:

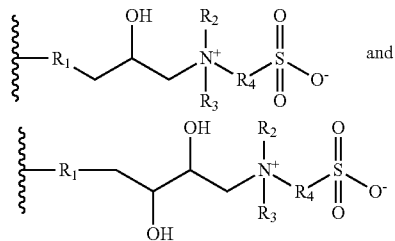

and wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH)$_n$—, —(CH$_2$)$_m$C(O)O(CH)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$—, —(OCH$_2$CH$_2$)$_m$— or —(CH$_2$CH$_2$O)$_m$—; R$_2$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH, R$_4$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, or —(CH$_2$)$_x$—; m, n and x are each an integer from 1 to 20 and ⁓ is the conjugated polymer backbone.

18. The conjugated polymer platform of claim 1 wherein said one or more zwitterionic side chains have the formula:

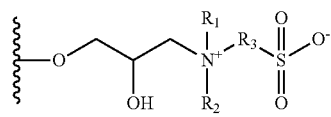

wherein R$_1$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_2$ are H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_3$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_n$—; n is an integer from 1 to 20; and ⁓ is the conjugated polymer backbone.

19. The conjugated polymer platform of claim 1 wherein said one or more zwitterionic side chains have the formula:

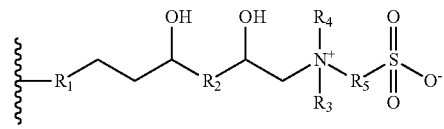

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH(CH$_2$)$_n$—, —(CH$_2$)$_m$C(O)NH(CH$_2$)$_n$—, —NHC(O)(CH$_2$)$_m$C(O)NH—, —OC(O)(CH$_2$)$_m$C(O)NH—, —O(CH$_2$)$_m$C(O)NH—, —NHC(O)(CH$_2$)$_m$O—, —NHC(O)(CH$_2$)$_m$C(O)O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O)CH$_2$CH$_2$—, —OC(O)(CH$_2$)$_m$—, —OC(O)(CH$_2$)$_m$C(O)O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$O)$_m$—; R$_2$ is —CH$_2$, CH$_2$CH$_2$—, —CH$_2$CH$_2$CH$_2$—, or —CH$_2$CH$_2$CH$_2$CH$_2$—, —(CH$_2$)$_x$—, R$_3$ is H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_4$ are H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; R$_5$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— or —(CH$_2$)$_y$—; m, n, x and y are each an integer from 1 to 20; and ⁓ is the conjugated polymer backbone.

20. The conjugated polymer platform of claim 1 wherein said one or more zwitterionic side chains have the formula:

wherein R$_1$ is —O—, —NH—, —C(O)NH—, —CH$_2$C(O)NH—, —CH$_2$CH$_2$C(O)NH—, —(CH$_2$)$_m$C(O)NH—, —NHC(O)—, —NHC(O)CH$_2$—, —NHC(O)CH$_2$CH$_2$—, —NHC(O)(CH$_2$)$_m$—, —(CH$_2$)$_m$NHC(O)(CH$_2$)$_n$—, —(CH$_2$)$_m$NHC(O)O(CH$_2$)$_n$—, —(CH$_2$)$_m$OC(O)NH (CH$_2$)$_n$—, —(CH$_2$)$_m$C(O)NH(CH$_2$)$_n$—, —NHC(O)(CH$_2$)$_m$ C(O)NH—, —OC(O)(CH$_2$)$_m$C(O)NH—, —O(CH$_2$)$_m$C(O) NH—, —NHC(O)(CH$_2$)$_m$O—, —NHC(O)(CH$_2$)$_m$C(O) O—, —C(O)O—, —CH$_2$C(O)O—, —CH$_2$CH$_2$C(O)O—, —(CH$_2$)$_m$C(O)O—, OC(O)—, —OC(O)CH$_2$—, —OC(O) CH$_2$CH$_2$—, —OC(O)(CH$_2$)$_m$—, —OC(O)(CH$_2$)$_m$C(O) O—, —OC(O)(CH$_2$)$_m$O—, —O(CH$_2$)$_m$C(O)O—, —(CH$_2$)$_m$ OC(O)(CH$_2$)$_n$—, —(CH$_2$)$_m$C(O)O(CH$_2$)$_n$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_m$O—, —O(CH$_2$)$_m$—, —(CH$_2$)$_m$—, —O(CH$_2$CH$_2$O)$_m$, —(OCH$_2$CH$_2$)$_m$— or —(CH$_2$CH$_2$ O)$_m$—; R$_2$ is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_x$—; R$_3$ is —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_y$—; R$_4$, R$_5$ and R$_6$ are H, —CH$_3$, CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m, n, x and y are each an integer from 1 to 20, and ⁓ is the conjugated polymer backbone.

21. The conjugated polymer platform of claim 1 comprising having the formula:

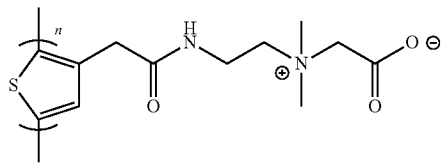

wherein n is an integer from 1 to 10,000,000.

22. The conjugated polymer platform of claim 1 having a formula selected from:

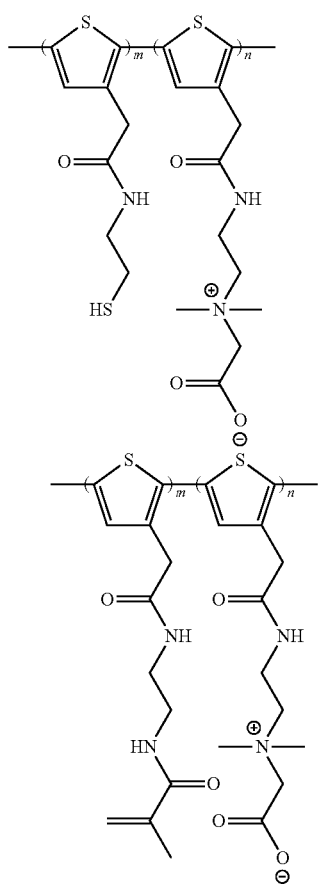

wherein m is an integer from 1 to 10,000,000 and n is an integer from 1 to 10,000,000.

23. The conjugated polymer platform of claim 1 having the formula:

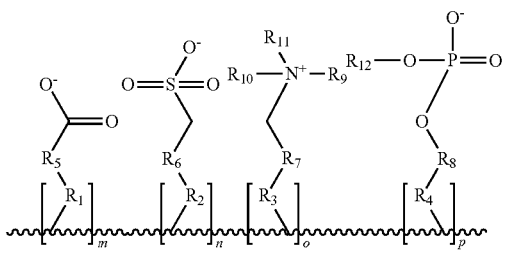

wherein $R_1$, $R_2$, $R_3$ and $R_4$ are —O—, —NH—, —C(O)NH—, —CH$_2$C(O)NH—, —CH$_2$CH$_2$C(O)NH—, —(CH$_2$)$_x$C(O)NH—, —NHC(O)—, —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$OC(O)NH(CH$_2$)$_y$—, —(CH$_2$)$_x$C(O)NH(CH$_2$)$_y$—, —NHC(O)(CH$_2$)$_x$C(O)NH—, —OC(O)(CH$_2$)$_x$C(O)NH—, —O(CH$_2$)$_x$C(O)NH—, —NHC(O)(CH$_2$)$_x$O—, —NHC(O)(CH$_2$)$_x$C(O)O—, —C(O)O—, —CH$_2$C(O)O—, —CH$_2$CH$_2$C(O)O—, —(CH$_2$)$_x$C(O)O—, OC(O)—, —OC(O)CH$_2$—, —OC(O)CH$_2$CH$_2$—, —OC(O)(CH$_2$)$_x$—, —OC(O)(CH$_2$)$_x$C(O)O—, —OC(O)(CH$_2$)$_x$O—, —O(CH$_2$)$_x$C(O)O—, —(CH$_2$)$_x$OC(O)(CH$_2$)$_y$—, —(CH$_2$)$_m$C(O)O(CH$_2$)$_x$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_m$O—, —O(CH$_2$)$_x$O—, —O(CH$_2$)$_x$—, —(CH$_2$)$_x$—, —O(CH$_2$CH$_2$O)$_x$, —(OCH$_2$CH$_2$)$_x$ or —(CH$_2$CH$_2$O)$_x$—; $R_5$, $R_6$, $R_7$ and $R_8$ are —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —(CH$_2$)$_z$—, —NHC(O)—, —NHC(O)CH$_2$—, —NHC(O)CH$_2$CH$_2$—, NHC(O)(CH$_2$)$_z$—, —OC(O)—, —OC(O)CH$_2$—, —OC(O)CH$_2$CH$_2$— or —OC(O))(CH$_2$)$_z$—; $R_9$, $R_{10}$ and $R_{11}$ are —H, —CH$_3$, —CH$_2$CH$_3$, —CH$_2$CH$_2$CH$_3$, —CH$_2$CH$_2$CH$_2$CH$_3$, —CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; $R_{12}$ is —H, —CH$_3$, —CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; x, y and z are an integer from 1 to 20; ⌇ is the conjugated polymer backbone; m, n and p are each an integer from 0 to 10,000,000; and o is an integer from 1 to 10,000,000.

24. The conjugated polymer platform of claim 1 having the formula:

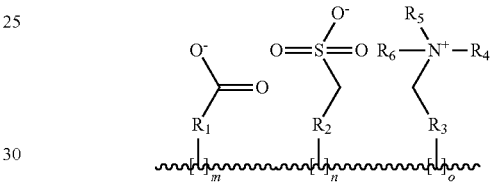

wherein $R_1$ is —NHC(O)CH$_2$—, —NHC(O)CH$_2$CH$_2$—, —NHC(O)(CH$_2$)$_x$—, —(CH$_2$)$_x$NHC(O)(CH$_2$)$_y$—, —(CH$_2$)$_x$NHC(O)O(CH$_2$)$_y$—, —(CH$_2$)$_x$OC(O)NH(CH$_2$)$_y$—, —(CH$_2$)$_x$C(O)NH(CH$_2$)$_y$—, —OC(O)CH$_2$—, —OC(O)CH$_2$CH$_2$—, —OC(O)(CH$_2$)$_x$—, —(CH$_2$)$_x$OC(O)(CH$_2$)$_y$—, —(CH$_2$)$_m$C(O)O(CH$_2$)$_x$—, —O(CH$_2$)$_x$—, —(CH$_2$)$_x$— or —(OCH$_2$CH$_2$)$_x$—; $R_2$, and $R_3$ are —C(O)NH—, —CH$_2$C(O)NH—, —CH$_2$CH$_2$C(O)NH—, —(CH$_2$)$_z$C(O)NH—, —NHC(O)—, —NHC(O)CH$_2$—, —NHC(O)CH$_2$CH$_2$—, —NHC(O)(CH$_2$)$_v$—, —(CH$_2$)$_z$NHC(O)(CH$_2$)$_v$—, —(CH$_2$)$_z$NHC(O)O(CH$_2$)$_v$—, —(CH$_2$)$_z$OC(O)NH(CH$_2$)$_v$—, —(CH$_2$)$_z$C(O)NH(CH$_2$)$_v$—, —NHC(O)(CH$_2$)$_z$C(O)NH—, —OC(O)(CH$_2$)$_z$C(O)NH—, —O(CH$_2$)$_z$C(O)NH—, —NHC(O)(CH$_2$)$_z$O—, —NHC(O)(CH$_2$)$_z$C(O)O—, —C(O)O—, —CH$_2$C(O)O—, —CH$_2$CH$_2$C(O)O—, —(CH$_2$)$_z$C(O)O—, OC(O)—, —OC(O)CH$_2$—, —OC(O)CH$_2$CH$_2$—, —OC(O)(CH$_2$)$_z$—, —OC(O)(CH$_2$)$_z$C(O)O—, —OC(O)(CH$_2$)$_z$O—, —O(CH$_2$)$_z$C(O)O—, —(CH$_2$)$_z$OC(O)(CH$_2$)$_v$—, —(CH$_2$)$_z$C(O)O(CH$_2$)$_v$—, —CH$_2$O—, —CH$_2$CH$_2$O—, —CH$_2$CH$_2$CH$_2$O—, —CH$_2$CH$_2$CH$_2$CH$_2$O—, —CH$_2$CH$_2$CH$_2$CH$_2$CH$_2$O—, —CH$_2$CH$_2$CH$_2$CH$_2$CH$_2$CH$_2$O—, —(CH$_2$)$_z$O—, —O(CH$_2$)O—, —O(CH$_2$)$_z$—, —(CH$_2$)$_z$—, —O(CH$_2$CH$_2$O)$_z$, —(OCH$_2$CH$_2$)— or —(CH$_2$CH$_2$O)$_x$—; $R_4$, $R_5$ and $R_6$ are —H, —CH$_3$, —CH$_2$CH$_3$, —CH$_2$CH$_2$CH$_3$, —CH$_2$CH$_2$CH$_2$CH$_3$, CH$_2$CH$_2$OH, —CH$_2$CH$_2$CH$_2$OH, —CH$_2$CH$_2$CH$_2$CH$_2$OH, or —CH$_2$CH$_2$CH$_2$CH$_2$CH$_2$OH; m and n are each an integer from 0 to 10,000,000; and o is an integer from 1 to 10,000,000.

25. The conjugated polymer platform of claim 2 wherein said one or more crosslinking side chains further comprises a crosslinking moiety selected from the group comprising acrylates, or acrylamides, and combinations thereof.

26. The conjugated polymer platform of claim 5 wherein said positively and negatively charged side chains have a formula selected from the group consisting of:

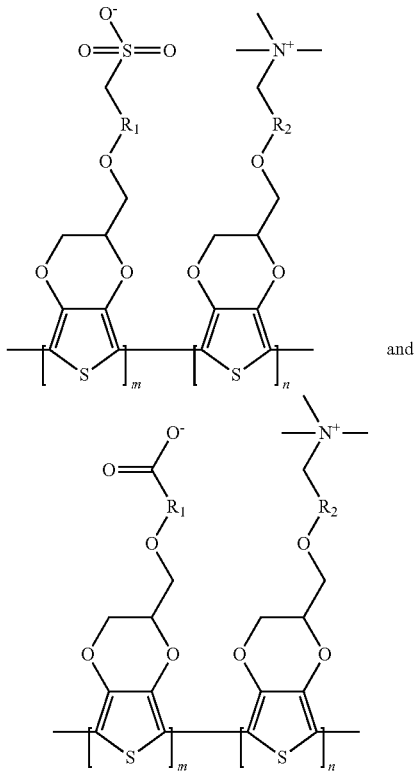

wherein $R_1$ and $R_2$ are —$CH_2CH_2C(O)NH$—, —$(CH)_zC(O)NH$—, —$(CH_2)_zNHC(O)(CH_2)_v$—, —$(CH_2)_zNHC(O)O(CH_2)_v$—, —$(CH_2)$ $OC(O)NH(CH)_v$—, —$(CH_2)_zC(O)NH(CH_2)_v$—, —$C(O)O$—, —$CH_2C(O)O$—, —$CH_2CH_2C(O)O$—, —$(CH_2)_zC(O)O$—, $OC(O)$—, —$OC(O)CH_2$—, —$OC(O)CH_2CH_2$—, —$OC(O)(CH_2)_z$—, —$OC(O)(CH_2)_zC(O)O$—, —$OC(O)(CH_2)_zO$—, —$O(CH_2)_zC(O)O$—, —$(CH_2)_z OC(O)(CH_2)_v$—, —$(CH_2)_zC(O)O(CH_2)_v$—, —$CH_2O$—, —$CH_2CH_2O$—, —$CH_2CH_2CH_2O$—, —$CH_2CH_2CH_2CH_2O$—, —$CH_2CH_2CH_2CH_2CH_2O$—, —$CH_2CH_2CH_2CH_2CH_2CH_2O$—, —$(CH_2)_zO$—, —$O(CH_2)_z$ $O$—, —$O(CH_2)_z$—, —$(CH_2)_z$—, —$O(CH_2CH_2O)_z$, —$(OCH_2CH_2)_z$—, —$(CH_2CH_2O)_z$—, —$CH_2$—, $CH_2CH_2$—, —$CH_2CH_2CH_2$—, —$CH_2CH_2CH_2CH_2$—, —$CH_2CH_2CH_2CH_2CH_2$—; —$CH_2CH_2CH_2CH_2CH_2CH_2$—, —$CH_2CH_2CH_2CH_2CH_2CH_2CH_2$—, $CH_2CH_2CH_2CH_2CH_2CH_2CH_2CH_2$—, —$CH_2CH_2CH_2CH_2CH_2CH_2CH_2CH_2CH_2$—, —$(CH)_z$—, —$C(O)(CH_2)$, —$CH_2CH_2CH_2CH_2CH_2CH_2CH_2CH_2CH_2CH_2$—; z and v are each an integer from 1 to 20; m is an integer from 1 to 10,000,000; and n is an integer 1 to 10,000,000.

27. The conjugated polymer platform of claim 5, wherein said positively and negatively charged side chains have a formula selected from the group consisting of:

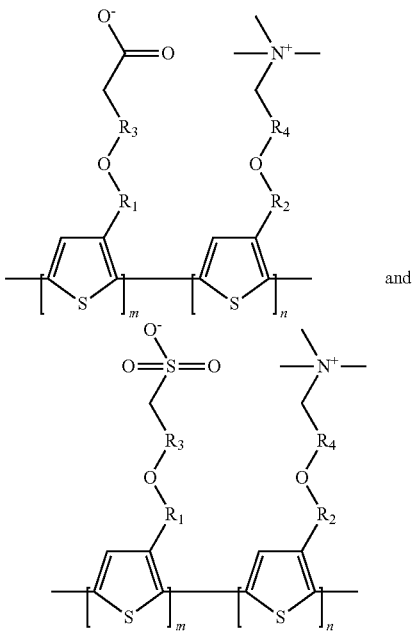

wherein $R_1$ and $R_2$ are —$(CH_2)_xNHC(O)(CH_2)_y$—, —$(CH_2)_x$ $NHC(O)O(CH_2)_y$—, —$(CH_2)_xOC(O)NH(CH_2)_y$—, —$(CH_2)_xC(O)NH(CH_2)_y$—, —$C(O)$—, —$CH_2C(O)$—, —$CH_2CH_2C(O)$—, —$(CH_2)_xC(O)O$—, —$OC(O)$—, —$OC(O)CH_2$—, —$OC(O)CH_2CH_2$—, —$OC(O)(CH_2)_x$—, —$OC(O)(CH_2)_xC(O)$—, —$OC(O)(CH_2)_x$—, —$O(CH_2)_xC(O)$—, —$(CH_2)_xOC(O)(CH_2)_y$—, —$(CH_2)_xC(O)O(CH_2)_y$—, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2$—, —$(CH_2)$—, —$O(CH_2)_x$—, —$O(CH_2)_x$—, —$(CH_2)_x$—, —$(OCH_2CH_2)$— or —$(CH_2CH_2O)_x$—, —$CH_2$—, —$CH_2CH_2$—, —$CH_2CH_2CH_2$—, —$CH_2CH_2CH_2CH_2$—, —$CH_2CH_2CH_2CH_2CH_2$—; —$CH_2CH_2CH_2CH_2$ $CH_2CH_2$—, —$CH_2CH_2CH_2CH_2CH_2CH_2CH_2$—, —$CH_2CH_2CH_2CH_2CH_2CH_2CH_2CH_2$—, —$CH_2CH_2$ $CH_2CH_2CH_2CH_2CH_2$—$CH_2CH_2$ $CH_2CH_2CH_2CH_2CH_2CH_2CH_2CH_2$—, —$(CH_2)_x$—, —$(CH_2)_xC(O)$—; $R_3$ and $R_4$ are —$(CH_2)_xNHC(O)(CH_2)_y$—, —$(CH_2)_xNHC(O)O(CH_2)_y$—, —$(CH_2)_xOC(O)NH(CH_2)_y$—, —$(CH_2)_xC(O)NH(CH_2)_y$—, —$OC(O)CH_2$—, —$OC(O)CH_2CH_2$—, —$OC(O)(CH_2)_x$—, —$(CH_2)_xOC(O)(CH_2)_y$—, —$(CH_2)_xC(O)O(CH_2)_y$—, —$(CH_2)_x$—, —$(CH_2CH_2O)_z(CH_2)_y$—, —$CH_2$—, —$CH_2CH_2$—, —$CH_2CH_2CH_2$—, —$CH_2CH_2CH_2CH_2$—, —$CH_2CH_2CH_2CH_2CH_2$—; —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2CH_2CH_2CH_2CH_2CH_2CH_2CH_2CH_2$— or —$CH_2CH_2CH_2CH_2CH_2CH_2CH_2CH_2CH_2CH_2$—; x, y, z and v are each an integer from 1 to 20; m is an integer from 1 to 10,000,000; and n is an integer from 1 to 10,000,000.

28. An implantable medical device comprising the conjugated polymer platform of claim 1.

* * * * *